(12) United States Patent
Rosen et al.

(10) Patent No.: US 7,375,192 B2
(45) Date of Patent: May 20, 2008

(54) ANTIBODIES THAT SPECIFICALLY BIND TO CHEMOKINE BETA-4

(75) Inventors: Craig A. Rosen, Laytonsville, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 191 days.

(21) Appl. No.: 10/513,705

(22) PCT Filed: Apr. 30, 2003

(86) PCT No.: PCT/US03/13414

§ 371 (c)(1),
(2), (4) Date: Sep. 6, 2005

(87) PCT Pub. No.: WO03/092597

PCT Pub. Date: Nov. 13, 2003

(65) Prior Publication Data

US 2006/0275210 A1    Dec. 7, 2006

Related U.S. Application Data

(60) Provisional application No. 60/376,561, filed on May 1, 2002.

(51) Int. Cl.
  *C07K 16/00* (2006.01)
(52) U.S. Cl. ............................. 530/387.1; 424/130.1; 424/178.1
(58) Field of Classification Search ............... None
See application file for complete search history.

(56) References Cited

U.S. PATENT DOCUMENTS

| | | | |
|---|---|---|---|
| 4,897,348 A | 1/1990 | Johnson et al. |
| 5,011,912 A | 4/1991 | Hopp et al. |
| 5,278,287 A | 1/1994 | Rollins et al. |
| 5,306,709 A | 4/1994 | Gewirtz |
| 5,346,686 A | 9/1994 | Lyle et al. |
| 5,413,778 A | 5/1995 | Kunkel et al. |
| 5,474,983 A | 12/1995 | Kuna et al. |
| 5,602,008 A | 2/1997 | Wilde et al. |
| 5,936,068 A | 8/1999 | Wilde et al. |
| 6,001,649 A | 12/1999 | Caput et al. |
| 6,096,300 A | 8/2000 | Hromas |
| 6,174,995 B1 | 1/2001 | Li et al. |
| 6,673,344 B1 | 1/2004 | Li et al. |

FOREIGN PATENT DOCUMENTS

| EP | 0538 030 2 | 4/1993 |
|---|---|---|
| WO | WO-90/06321 | 6/1990 |
| WO | WO-91/04274 | 4/1991 |
| WO | WO-91/12815 | 9/1991 |
| WO | WO-92/05198 | 4/1992 |
| WO | WO-92/20372 | 11/1992 |
| WO | WO-95/17092 | 6/1995 |
| WO | WO-95/31467 | 11/1995 |
| WO | WO-95/31468 | 11/1995 |
| WO | WO-96/05856 | 2/1996 |
| WO | WO-96/06169 | 2/1996 |
| WO | WO-96/09062 | 3/1996 |
| WO | WO-96/16979 | 6/1996 |
| WO | WO-96/39520 | 12/1996 |
| WO | WO-96/39521 | 12/1996 |
| WO | WO-96/39522 | 12/1996 |
| WO | WO-97/15594 | 5/1997 |
| WO | WO-97/15595 | 5/1997 |
| WO | WO-97/31098 | 8/1997 |
| WO | WO-97/35982 | 10/1997 |
| WO | WO-98/01557 | 1/1998 |
| WO | WO-98/09171 | 3/1998 |
| WO | WO-98/11226 | 3/1998 |
| WO | WO-98/14573 | 4/1998 |
| WO | WO-98/17800 | 4/1998 |
| WO | WO-98/21330 | 5/1998 |
| WO | WO-99/47674 | 9/1999 |

(Continued)

OTHER PUBLICATIONS

PCT/GB90/02017*

(Continued)

*Primary Examiner*—Christopher Yaen
*Assistant Examiner*—Hong Sang
(74) *Attorney, Agent, or Firm*—Human Genome Sciences, Inc.

(57) ABSTRACT

The present invention relates to antibodies and related molecules that specifically bind to CK-B4. Such antibodies have uses, for example, in the prevention and treatment of cancer as well as immune system diseases and disorders including cancers, as well as immune system diseases and disorders including autoimmune diseases, inflammatory disorders, immunodeficiencies, infections, HIV, arthritis, allergy, psoriasis, dermatitis, and inflammatory bowel disease. The invention also relates to nucleic acid molecules encoding anti-CK-B4 antibodies, vectors and host cells containing these nucleic acids, and methods for producing the same. The present invention relates to methods and compositions for preventing, detecting, diagnosing, treating or ameliorating a disease or disorder, especially cancers, as well as immune system diseases and disorders including autoimmune disease, inflammatory disorders, immunodeficiencies, infections, HIV, arthritis, allergy, psoriasis, dermatitis, and inflammatory bowel disease, comprising administering to an animal, preferably a human, an effective amount of one or more antibodies or fragments or variants thereof, or related molecules, that specifically bind to CK-B4.

29 Claims, No Drawings

FOREIGN PATENT DOCUMENTS

WO          WO 0046248 A1 *   8/2000

OTHER PUBLICATIONS

Rich et al., J. Managed Care Pharmacy, Aug. 2004, 10(4): 318-325.*
Curse et al., Illustrated Dictionary of Immunology, 1995 by CRC press, page 241.*
Amit et al., Science, 1986, vol. 233, 747-753.*
Panka et al., Proc. Natl. Acad. Sci. USA, 1988, vol. 85, 3080-3084.*
Rudikoff et al., Proc. Natl. Acad. Sci. USA, 1982, vol. 79, 1979-1983.*
Bowie, et al., Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed), Birkhauser, Boston, MA, pp. 433, and 492-495.*
Skolnick et al., From genes to protein structure an function: novel applications of computational apporaches in the genomic era, Trends in Biotech. 18:34-39, 2000.*
GenBank Accession No. AA297433 (Apr. 18, 1997).
GenBank Accession No. AA403048 (May 16, 1997).
GenBank Accession No. AA404346 (May 16, 1997).
GenBank Accession No. AA426245 (Oct. 16, 1997).
GenBank Accession No. AA739063 (Jan. 14, 1998).
GenBank Accession No. AAB38703 (Dec. 16, 1996).
GenBank Accession No. AAB61534.1 (Aug. 6, 1996).
GenBank Accession No. AAC50943.1 (Aug. 6, 1996).
GenBank Accession No. AC002482 (Aug. 21, 1997).
GenBank Accession No. AI735669 (Jun. 14, 1999).
GenBank Accession No. AI925360 (Sep. 2, 1999).
GenBank Accession No. AJ000979 (Jun. 30, 1997).
GenBank Accession No. AJ001634 (Sep. 10, 1997).
GenBank Accession No. AAW56690 (Jun. 3, 1997).
GenBank Accession No. CAA04888 (Sep. 10, 1996).
GenBank Accession No. CAA66950 (Dec. 16, 1997).
GenBank Accession No. CAB01111 (Jul. 30, 1996).
GenBank Accession No. CAB01112 (Jul. 30, 1996).
GenBank Accession No. D17181 (Jun. 21, 1993).
GenBank Accession No. D31065 (Feb. 8, 1995).
GenBank Accession No. D86955 (Mar. 6, 1997).
GenBank Accession No. I35613 (Feb. 22, 1997).
GenBank Accession No. AAR29479 (Apr. 25, 1995).
GenBank Accession No. T27336 (Dec. 6, 1994).
GenBank Accession No. T27433 (Dec. 6, 1994).
GenBank Accession No. T64134 (Feb. 17, 1995).
GenBank Accession No. T64262 (Feb. 17, 1995).
GenBank Accession No. U46767 (Dec. 14, 1996).
GenBank Accession No. U64197 (Jun. 25, 1997).
GenBank Accession No. U77035 (Jan. 23, 1997).
GenBank Accession No. W44398 (Jun. 11, 1998).
GenBank Accession No. AAW57475 (Sep. 7, 1998).
GenBank Accession No. W61279 (Sep. 24, 1998).
GenBank Accession No. X98306 (Jul. 20, 1998).
GenBank Accession No. Z77650 (Jul. 30, 1996).
GenBank Accession No. Z77651 (Jul. 30, 1996).
Geneseq Accession No. AAR95690 (Dec. 20, 1996).
Geneseq Accession No. AAW17660 (Dec. 16, 1997).
Geneseq Accession No. AAT90880 (May 21, 1998).
Geneseq Accession No. AAT90883 (May 21, 1998).
Geneseq Accession No. AAV28591 (Aug. 17, 1998).
Geneseq Accession No. AAW30191 (May 21, 1998).
Geneseq Accession No. AAW44398 (Jun. 11, 1998).
Geneseq Accession No. AAW56087 (Aug. 17, 1998).
Genseq Accession No. AAR93087 (Aug. 27, 1996).
Geneseq Accession No. AAW22670 (Mar. 19, 1998).
Geneseq Accession No. AAR29479 (Apr. 22, 1993).
Abiko, et al., "Expression of MIP-3alpha/CCL20, a macrophage inflammatory protein in oral squamous cell carcinoma," *Arch. Oral Biol.*, 48(2):171-175 (Feb. 2003).

Adema et al., "A dendritic-cell-derived C-C chemokine that preferentially attracts naive T cell," *Nature*, 387:713-717 (Jun. 1997).
Akahoshi, et al., "Production of macrophage inflammatory protein 3 (MIP-3) (CCL20) and MIP-3 (CCL19) by human peripheral blood neurtophils in response to microbial pathogens," *Infect. Immun.*, 71(1):524-526 (Jan. 2003).
Ambrosini, et al., "Astrocytes are the major intracerebral source of macrophage inflammatory protein-3slaph/CCL20 in relapsing experimental autoimmune encephalomyelitis and in vitro," *Glia*, 41(3):290-300 (Feb. 2003).
Bennouna, et al., "Cross-talk in the innate innume system: neutrophils instruct recruitment and activation of dendritic cells during microbial infection," *J. Immunol.*, 171:6052-6058 (Dec. 2003).
Berger, M.S., "Isolation of Monocyte Chemotactic Protein-4," *Clinical Res.*, 42(2):305A (1994).
Bischoff et al., "Monocyte Chemotactic Protein 1 Is a Potent Activator of Human Basophils," *J. Exp. Med.*, 175:1271-1275 (May 1992).
Blum et al., "Three Human Homologs of a Murine Gene Encoding an Inhibitor of Stem Cell Proliferation," *DNA and Cell Biol.*, 9(8)589-602 (1990).
Brown et al., "A Family of Small Inducible Proteins Secreted by Leukocytes are Members of a New Superfamily that Includes Leukocyte and Fibroblast-Derived Inflammatory Agents, Growth Factors, and Indicators of Various Activation Processes," *J. Immunol.*, 142(2):679-687 (Jan. 15, 1989).
Clements et al., "Biological and Structural Properties of MIP-la Expressed in Yeast," *Cytokine*, 4(1):76-82 (Jan. 1992).
Craddock et al., "Antibodies to VLA4 integrin mobilize long-term repopulating cells and augment cytokine-induced mobilization in primates and mice," *Blood*, 90(12):4779-4788 (Dec. 15, 1997).
Crittenden, et al., "Expression of inflammatory chemokines combined with local tumor destruction enhances tumor regression and long-term immunity," *Cancer Res.*, 63:5505-5512 (Sep. 1, 2003).
Derynck et al., "Recombinant Expression, Biochemical Characterization, and Biological Activities of the Human MGSA/gro Protein," *Biochem.*, 29(44):10225-10233 (1990).
Dieu-Nosjean, et al., "Macrophage inflammatory protein 3 is expresses at inflamed epithelial surfaces and is the most potent chemokine known in attracting langerhans cell precursors," *J. Exp. Med.*, 192(5):705-717 (Sep. 2000).
Furuta et al., "Production and Characterization of Recombinant Human Neutrophil Chemotactic Factor," *J. Biochem.*, 106:436-441 (1989).
Fushimi, et al., "Macrophage inflammatory protein 3 alpha transgene attracts dendritic cells to established murine tumors and supresses tumor growth," *J. Clin. Invest.*, 105(10):1383-1393 (May 2000).
Garcia-Zepeda et al., "Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3," *J. Immunol.*, 157(12):5613-5626 (Dec. 15, 1996).
George et al., "Current Methods in Sequence Comparison and Analysis, Macromolecular Sequencing & Synthesis," Alan R. Liss Inc. Ch. 12:127-149 (1988).
Glover, David M., "Gene Cloning: The Mechanics of DNA Manipulation," Chapman and Hall, London and New York, Ch. 1-3, pp. 1-84 (1984).
Glover, David M., "Gene Cloning: The Mechanics of DNA Manipulation," Chapman and Hall, London and New York, Ch.4-6, pp. 85-157 (1984).
Glover, David M., "Gene Cloning: The Mechanics of DNA Manipulation," Chapman and Hall, London and New York, Ch. 7-8, pp. 158-218 (1984).
Graham et al., "SCI/MIP-la: A Potent Stem Cell Inhibitor with Potential Roles in Development," *Develop. Biol.*, 151:377-381 (1992).
Hieshima et al., "A Novel Human CC Chemokine P A R C That Is Most Homologous to Macrophage-Inflammatory Protein-1a/LD78a and Chemotactic for T Lymphocytes, but Not for Monocytes," *J. Immunol.*, 159:1140-1149 (1977).

Hieshima et al. "Molecular Cloning of a Novel Human CC Chemokine Liver and Activation-regulated Chemokine (LARC) Expressed in Liver," *J. Biol. Chem.* 272(9):5846-5853 (Feb. 28, 1997).

Homey, et al., "Up-regulation of macrophage inflammatory protein-3CCL20 and CC chemokine receptor 6 in psoriasis," *J. Immunol.*, 164:6621-6632 (2000).

Hoover, et al., "The structure of human macrophage inflammatory protein-3alpha/CCL20—linking antimicrobial and CC chemokine receptor-6-binding activities with human beta- defensins," *J. Biol. Chem.*, 277(40):37647-37654 (Oct. 4, 2002).

Hosokawa, et al., "Macrophage inflammatory protein 3 alpha-CC chemokine receptor 6 interactions play an important role in CD4+ t-cell accumulation in periodontal diseased tissue," *Clin. Exp. Immunol.*, 128(3):548-554 (Jun. 2002).

Hromas et al., "Cloning and Characterization of Exodus, a Novel β-Chemokine," *Blood*, 89(9):3315-3322 (1997).

Jose et al., "Eotaxin: A Potent Eosinophil Chemoattractant Cytokine Detected in a Guinea Pig Model of Allergic Airways Inflammation," *J. Exp. Med.*, 179: 881-887 (Mar. 1994).

Kleeff, et al., "Detection and localization of Mip-3alpha/LARC/exodus, a macrophage proinflammatory chemokine, and its CCR6 receptor in human pancreatic cancer," *Int. J. Cancer*, 81(4):650-657 (May 17, 1999).

Kodelja et al., "Alternative Macrophage Activation-Associated CC-Chemokine-1, a Novel Structural Homologue of Macrophage Inflammatory Protein-1a with a TH2-Associated Expression Pattern," *J. Immunol.*, 160(3):1411-1418 (Feb. 1, 1998).

Kohler, et al., "A role for macrophage inflammatory protein-3alpha/CC chemokine ligand 20 in immune priming during T cell-mediated inflammation of the central nervous system," *J. Immunol.*, 170:6298-6303 (Jun. 2003).

Kuna et al., "Monocyte Chemotactic and Activating Factor Is a Potent Histamine-releasing Factor for Human Basophils," *J. Exp. Med.*, 175:489-493 (Feb. 1992).

Kurdowska et al., "Biological and Kinetic Characterization of Recombinant Human Macrophage Inflammatory Peptides 2 Alpha and Beta and Comparison with Neutrophil Activating Peptide 2 and Interleukin 8," *Cytokine*, 6(2):124-134 (Mar. 1994).

Kwon et al., "cDNA sequences of two inducible t-cell genes," *PNAS USA*, 86:1963-1967 (1989).

Kwon, et al., "Colonic epithelial cells are a major site of macrophage inflammatory protein 3alpha (MIP-3alpha) production in normal colon and inflammatory bowel disease," *Gut*, 51(6):818-826 (Dec. 2002).

Lamkhioued, et al., "Monocyte chemoattractant protein (MCP)-4 expression in the airways of patients with asthma," *J Respir Crit Care Med.*, 162:723:732 (2000).

Laterveer et al., "Rapid mobilization of hematopoietic progenitor cells in rhesus monkeys by a single intravenous injection of interleukin-8," *Blood*, 87(2):781-788 (Jan. 15, 1996).

Laterveer, L., et al., "Improved survival of lethally irradiated recipient mice transplanted with circulating progenitor cells mobilized by IL-8after pretreatment with stem cell factor," *Exp. Hemat.*, 24:1387-1393 (1996).

Lerner, Richard A., "Tapping the immunological repertoire to produce antibodies of predetermined specifically," *Nature*, 299:592-593 (Oct. 1982).

Lin, et al., "Selective early production of CCL20, or macrophage inflammatory protein 3alpha, by human mast cells in response to *Pseudomonas aeruginosa*," *Infect. Immun.*, 71(1):365-373 (Jan. 2003).

Liu et al., "The granulocyte colony-stimulating factor receptor is required for the mobilization of murine hematopoietic progenitors into peripheral blood by cyclophosphamide or interleukin-8 but not flt-3 ligand," *Blood*, 90(7):2522-2528 (Oct. 1, 1997).

Lukacs et al., "The Role of Macrophage Inflammatory Protein 1 a in *Schistosoma mansoni*," J. of Exp. Med. 177:1551-1559 (June 1993).

Matsui, et al., "Selective recruitment of CCR6-expressing cells by increased production fo MIP-3 alpha in rheumatoid arthritis," *Clin. Exp. Immunol.*, 125(1):155-161 (Jul. 2001).

Matsushima et al., "Purification and Characterization of a Novel Monocyte Chemotactic and Activating Factor Produced by a Human Myelomonocytic Cell Line," *J. Exp. Med.* 169:1485-1490 (Apr. 1989).

Nakao et al., "Structures of Human Genes Coding for Cytokine LD78 and Their Expression," *Molec. Cell Biol.* 10(7):3646-3658 (Jul. 1990).

Nishi, et al., "Involvement of myeloid dendritic cells in the development of gastric secondary lymphoid follicles in helicobacter pylori-infected neonatally thymectomized BALB/c mice," *Infect. Immun.*, 71(4):2153-2162 (Apr. 2003).

Obaru et al., "A cDNA Clone Used to Study mRNA Inducible in Human Tonsillar Lymphocytes by a Tumor Promoter," *J. Biochem.* 99(3):885-894 (1986).

Opdennaker et al., "Human monocyte chemotactic protein-3 (MCP-3): molecular cloning of the cDNA and comparison with other chemokines," *Biochem. Biophys. Res. Commun.* 191(2)535-542 (Mar. 15, 1993).

Patel et al., "Molecular and functional characterization of two novel human C-C chemokines as inhibitors of two distinct classes of myeloid progenitors," *J. Exp. Med.* 185(7):1163-1172 (Apr. 7, 1997).

Ruth et al., "Role of macrophage inflammatory protein-3alpha and its ligand CCR6 in rheumatoid arthritis," *Lab. Invest.*, 83(4):579-588 (Apr. 2003).

Sandhu, JS., "Protein Engineering of Antibodies," *Critical Rev. in Biotechnol.* 12:437-445 (1992).

Schall, Thomas J., "Biology of the RANTES/SIS Cytokine Family," *Cytokine* 3(3):165-183 (May 1991).

Schall et al., "Molecular cloning and expression of the murine RANTES cytokine: structural and functional conservation between mouse and man," *Eur. J. Immunol.* 22:1477-1481 (Jun. 1992).

Seffernick, et al., *J. Bacteriology,* 183:2405-2410 (2001).

Sierro, et al., "Flagellin stimulation of intestinal epithelial cells triggers CCL20-mediated migration of dendritic cells," *PNAS*, 98(24):13722-13727 (Nov. 20, 2001).

Skolnick, et al., "Structural genomics and its importance for gene function analysis," *Nature Biotechnol.*, 18:283-287 (Mar. 2000).

Sudo et al., "2058 Expressed Sequence Tags (ESTs) from a Human Fetal Lung cDNA Library," *Genomics* 24:276-279 (1994).

Taha, et al., "Eotaxin and monocyte chemotactic protein-4 mRNA expression in small airways of asthmatic and nonasthmatic individuals," *J Allergy Clin Immonol.*, 103(3, part 1):476-483 (1999).

Taha, et al., "Increased expression of the chemoattractant cytokines eotaxin, monocyte chemotactic protein-4, and interleukin-16 in induced sputum in asthmatic patients," *Chest*, 120:595-601 (Aug. 2001).

Taub et al., "Chemokines, inflammation and the immune system," *Ther. Immunol.* 1(4):229-246 (Aug. 1994).

Uguccioni et al., "Monocyte Chemotactic Protein 4 (MCP-4), a Novel Structural and Functional Analogue of MCP-3 and Eotaxin," *J. Exp. Med.* 183:2379-2384 (May 1996).

Wells, *Biochemistry*, 29:8509-8517 (1990).

Wolpe et al., "Macrophage inflammatory proteins 1 and 2: members of a novel superfamily of cytokines," *FASEB J.* 3:2565-2573 (1989).

Wolpe et al., "Identification and characterization of macrophage inflammatory protein 2," *Proc. Natl. Acad. Sci. USA*, 86:612-616 (1989).

Wolpe et al., "Macrophages secrete a novel heparin-binding protein with infammatory and neutrophil chemokinetic properties," *J. Exp. Med.*, 167:570-581 (1998).

Widmer, Urs, et al., Genomic Cloning and Promoter Analysis of Macrophage Inflammatory Protein (MIP)-2, MIP-la, and MIP-1β, Members of the Chemokine Superfamily of Proinflammatory Cytokines, *J. Immunol.* 150(11):4996-5012 (Jun. 1, 1993).

Yang et al., "Many chemokines including CCL20/MIP-3alpha display antimicrobial activity," *J. Leukoc. Biol.*, 74(3):448-455 (Sep. 2003).

Yoshimura et al., "Production and characterization of mouse monoclonal antibodies against human monocyte chemoattractant protein-1," *J Immunol.* 147:2229-2233 (1991).

Zipfel et al., "Mitogenic Activation of Human T Cells Induces Two Closely Related Genes Which Share Structural Similarities with a New Family of Secreted Factors," *J. Immunol.*, 142(5):1582-1590 (Mar. 1, 1989).

International Search Report, EP 97 30 3204 (Jan. 23, 1998).

Partial European Search Report, Application No. EP 99 12 6093.6, dated Apr. 14, 2000.

* cited by examiner

ANTIBODIES THAT SPECIFICALLY BIND TO CHEMOKINE BETA-4

FIELD OF THE INVENTION

The present invention relates to antibodies and related molecules that specifically bind to chemokine beta-4. Such antibodies have uses, for example, in wound healing and in the diagnosis, prevention, and treatment of cancers, as well as immune system diseases and disorders including autoimmune disease, inflammatory disorders, immunodeficiencies, infections, HIV, arthritis, allergy, psoriasis, dermatitis, and inflammatory bowel disease. The invention also relates to nucleic acid molecules encoding anti-chemokine beta-4 antibodies, vectors and host cells containing these nucleic acids, and methods for producing the same. The present invention relates to methods and compositions for preventing, detecting, diagnosing, treating or ameliorating a disease or disorder including cancers, as well as immune system diseases and disorders including autoimmune disease, inflammatory disorders, immunodeficiencies, infections, HIV, arthritis, allergy, psoriasis, dermatitis, and inflammatory bowel disease, comprising administering to an animal, preferably a human, an effective amount of one or more antibodies or fragments or variants thereof, or related molecules, that specifically bind to chemokine beta-4.

BACKGROUND OF THE INVENTION

Chemokines, also referred to as intercrine cytokines, are a subfamily of structurally and functionally related cytokines. These molecules are 8-14 kd in size. In general chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "CXC" subfamily. In the beta subfamily, the two cysteines are in an adjacent position and are, therefore, referred to as the "CC" subfamily. Recently, a new chemokine-like molecule, lymphotactin/SCM-1, which lacks the first and the third conserved cysteine residues, has been isolated and may represent a third subfamily (Kelner et al., *Science* 266:1395-1399 (1994)).

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein I (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

Chemokine beta-4 (CK-β4; also known as CCL20, MIP-3α, and LARC) represents a novel, divergent beta-chemokine. CK-β4 contains the four cysteine residues characteristic of CC chemokines and shows sequence similarity with other human CC chemokines. The highest homology (28%) is with chemoline MIP-1β (Hieshima, et al. *J. Biol. Chem.* 272:5846-5853 (1997)). CK-β4 is expressed preferentially in lymphocytes and monocytes, and its expression is markedly upregulated by mediators of inflammation such as tumor necrosis factor (TNF) and lipopolysaccharide. The CK-β4 gene has been mapped between the bands of q33 and q37 of chromosome 2 (Ibid.). The only receptor identified for CK-β4, thus far, is CCR6 (Greaves, et al., *J. Exp. Med* 186:837-844).

The immune cells that are responsive to the chemokines have a vast number of in vivo functions and therefore their regulation by such chemokines is an important area in the treatment of disease. For example, eosinophils destroy parasites to lessen parasitic infection. Eosinophils are also responsible for chronic inflammation in the airways of the respiratory system. Macrophages are responsible for suppressing tumor formation in vertebrates. Further, basophils release histamine, which may play an important role in allergic inflammation.

Accordingly, promoting and inhibiting such cells, has wide therapeutic application. There is a clear need, therefore, for identification and characterization of compositions, such as antibodies, that influence the biological activity of chemokines, both normally and in disease states. In particular, there is a need to isolate and characterize antibodies that modulate the biological activities of chemokine beta-4 for the treatment of proliferative disorders, as well as immune system diseases and disorders including autoimmune disease, inflammatory disorders, immunodeficiencies, infections, HIV, arthritis, allergy, psoriasis, dermatitis, and inflammatory bowel disease.

SUMMARY OF THE INVENTION

The present invention encompasses antibodies (including molecules comprising, or alternatively consisting of, antibody fragments or variants thereof) that specifically bind to a chemoline beta-4 polypeptide (CK-B4; also known as macrophage inflammatory protein 3-α (MIP-3α), CCL20, Exodus-1, and liver and activation-regulated chemokine (LARC); described in International Publication Nos. WO 96/05856, WO 97/31098, and U.S. Pat. No. 5,981,230 each of which are hereby incorporated by reference in their entireties) or a polypeptide fragment or variant of CK-B4. In particular, the invention encompasses antibodies (including molecules comprising, or alternatively consisting of, antibody fragments or variants thereof) that specifically bind to a CK-B4 polypeptide or polypeptide fragment or variant of human CK-B4 such as SEQ ID NO:2.

The present invention relates to methods and compositions for preventing, treating or ameliorating a disease or disorder comprising administering to an animal, preferably a human, an effective amount of one or more antibodies or fragments or variants thereof, or related molecules, that specifically bind to CK-B4 or a fragment or variant thereof. In specific embodiments, the present invention relates to methods and compositions for preventing, treating or ameliorating a disease or disorder associated with CK-B4 function or aberrant CK-B4 expression, comprising administering to an animal, preferably a human, an effective amount of one or more antibodies or fragments or variants thereof, or related molecules, that specifically bind to CK-B4 or a fragment or variant thereof.

In highly preferred embodiments, the present invention encompasses methods for using the antibodies of the present invention to treat, prevent, diagnose and/or prognose a disease or disorder of the immune system. In highly preferred embodiments, the present invention encompasses methods for using antibodies of the invention to treat, prevent, diagnose and/or prognose an inflammatory disorder (e.g., psoriasis, dermatitis, Langerhans cell histocytosis, inflammatory bowel syndrome, allergy, Crohn's disease). In additional preferred embodiments, the present invention relates to antibody-based methods and compositions for preventing, treating or ameliorating infectious disorders (e.g., human immunodeficiency virus (HIV) infection). In other preferred embodiments, the present invention relates to antibody-based methods and compositions for preventing, treating or ameliorating autoimmune disorders (e.g., rheumatoid arthritis and autoimmune encephalitis), graft-vs.-host reaction, and/or immunodeficiencies.

In other highly preferred embodiments, the invention encompasses methods for using the antibodies of the invention to inhibit B cell, T cell and/or dendritic cell chemotaxis. In specific embodiments, the invention encompasses methods for using the antibodies of the present invention to inhibit memory B cell or T cell (e.g., CD4 positive T cell) chemotaxis.

In other highly preferred embodiments, the invention encompasses methods for using the antibodies of the invention to stimulate B cell, T cell and/or dendritic cell chemotaxis. In specific embodiments, the invention encompasses methods for using the antibodies of the present invention to stimulate memory B cell or T cell (e.g., CD4 positive T cell) chemotaxis.

In other preferred embodiments, the invention encompasses methods for using the antibodies of the invention to inhibit proliferation of cells expressing a CK-B4 receptor (e.g., T cell, dendritic cell, or B cell).

In other preferred embodiments, the invention encompasses methods for using the antibodies of the invention to stimulate proliferation of cells expressing a CK-B4 receptor (e.g., T cell, dendritic cell, or B cell).

In highly preferred embodiments, the present invention relates to antibody-based methods and compositions for preventing, treating or ameliorating cancers (e.g., leukemia, T-cell lymphoma, B-cell lymphoma, prostate cancer, breast cancer, lung cancer, colon cancer, urinary cancer, non-Hodgkin's lymphoma, renal cell carcinoma, and myeloproliferative disorders).

In a further highly preferred embodiment of the invention, antibodies of the present invention may be used to promote wound healing.

Another embodiment of the present invention includes the use of the antibodies of the invention as a diagnostic tool to monitor the expression of CK-B4.

The present invention encompasses single chain Fv's (scFvs) that specifically bind CK-B4 polypeptides (e.g., SEQ ID NOs:20-36). Thus, the invention encompasses these scFvs, listed in Table 1. In addition the invention encompasses cell lines engineered to express antibodies corresponding to these scFvs which have been deposited with the American Type Culture Collection ("ATCC") as of the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the International Recognition of the Deposit of Microorganisms for Purposes of Patent Procedure.

Further, the present invention encompasses the polynucleotides encoding the scFvs, as well as the amino acid sequences encoding the scFvs. Molecules comprising, or alternatively consisting of, fragments or variants of these scFvs (e.g., VH domains, VH CDRs, VL domains, or VL CDRs having an amino acid sequence of any one of the scFvs referred to in Table 1), that specifically bind to CK-B4 or fragments or variants thereof are also encompassed by the invention, as are nucleic acid molecules that encode these antibodies and/or molecules.

The present invention also provides anti-CK-B4 antibodies which are coupled to a detectable label, such as an enzyme, a fluorescent label, a luminescent label, or a bioluminescent label. The present invention also provides anti-CK-B4 antibodies which are coupled to a therapeutic or cytotoxic agent. The present invention also provides anti-CK-B4 antibodies which are coupled to a radioactive material.

The present invention also provides antibodies that specifically bind one or more CK-B4 polypeptides and that act as either CK-B4 agonists or CK-B4 antagonists. In specific embodiments, the antibodies of the invention inhibit CK-B4 binding to a CK-B4 receptor (e.g., CCR6; GenBank ID: U68030).

In specific embodiments, the antibodies of the invention inhibit chemotaxis of cells that express a CK-B4 receptor (e.g., CCR6). In specific embodiments, the antibodies of the invention inhibit chemotaxis of lymphocytes (e.g., T cells, B cells). In specific embodiments, the antibodies of the invention inhibit chemotaxis of dendritic cells.

In specific embodiments, the antibodies of the invention stimulate chemotaxis of cells that express a CK-B4 receptor (e.g., CCR6). In specific embodiments, the antibodies of the invention stimulate chemotaxis of lymphocytes (e.g., T cells, B cells). In specific embodiments, the antibodies of the invention stimulate chemotaxis of dendritic cells.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

The term "antibody," as used herein, refers to immunoglobulin molecules and immunologically active portions of immunoglobulin molecules, i.e., molecules that contain an antigen binding site that specifically binds an antigen. As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VH domain of antibody linked to a VL domain of an antibody. Antibodies that specifically bind to CK-B4 may have cross-reactivity with other antigens. Preferably, antibodies that specifically bind to CK-B4 do not cross-react with other antigens (e.g., other members of the chemokine superfamily). Antibodies that specifically bind to CK-B4 can be identified, for example, by immunoassays or other techniques known to those of skill in the art.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers withon an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94, both of which are hereby incorporated by reference in their entireties.) ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

By "isolated antibody" is intended an antibody removed from its native environment. Thus, an antibody produced by, purified from and/or contained within a hybridoma and/or a recombinant host cell is considered isolated for purposes of the present invention.

Unless otherwise defined in the specification, specific binding or immunospecifc binding by an anti-CK-B4 antibody means that the anti-CK-B4 antibody binds CK-B4 but does not significantly bind to (i.e., cross-react with) proteins other than CK-B4, such as other proteins in the same family of proteins). An antibody that binds CK-B4 protein and does not cross-react with other proteins is not necessarily an antibody that does not bind said other proteins in all conditions; rather, the CK-B4-specific antibody of the invention preferentially binds CK-B4 compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that CK-B4-specific antibodies bind to epitopes of CK-B4, an antibody that specifically binds CK-B4 may or may not bind fragments of CK-B4 and/or variants of CK-B4 (e.g., proteins that are at least 90% identical to CK-B4) depending on the presence or absence of the epitope bound by a given CK-B4-specific antibody in the CK-B4 fragment or variant. Likewise, CK-B4-specific antibodies of the invention may bind species orthologues of CK-B4 (including fragments thereof) depending on the presence or absence of the epitope recognized by the antibody in the orthologue. Additionally, CK-B4-specific antibodies of the invention may bind modified forms of CK-B4, for example, CK-B4 fusion proteins. In such a case when antibodies of the invention bind CK-B4 fusion proteins, the antibody must make binding contact with the CK-B4 moiety of the fusion protein in order for the binding to be specific. Antibodies that specifically bind to CK-B4 can be identified, for example, by immunoassays or other techniques known to those of skill in the art, e.g., the immunoassays described in the Examples below.

The term "variant" as used herein refers to a polypeptide that possesses a similar or identical amino acid sequence as a CK-B4 polypeptide, a fragment of a CK-B4 polypeptide, an anti-CK-B4 antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a CK-B4 polypeptide, a fragment thereof, an anti-CK-B4 antibody or antibody fragment thereof (including a VH domain, VHCDR, VL domain, or VLCDR having an amino acid sequence of any one or more scFvs referred to in Table 1) described herein; (b) a polypeptide encoded by a nucleotide sequence, the complementary sequence of which hybridizes under stringent conditions to a nucleotide sequence encoding a CK-B4 polypeptide (e.g., SEQ ID NO:2), a fragment of a CK-B4 polypeptide, an anti-CK-B4 antibody or antibody fragment thereof (including a VH domain, VHCDR, VL domain, or VLCDR having an amino acid sequence of any one of those referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a CK-B4 polypeptide, a fragment of a CK-B4 polypeptide, an anti-CK-B4 antibody or antibody fragment thereof (including a VH domain, VHCDR, VL domain, or VLCDR having an amino acid sequence of any one or more scFvs referred to in Table 1), described herein. A polypeptide with similar structure to a CK-B4 polypeptide, a fragment of a CK-B4 polypeptide, an anti-CK-B4 antibody or antibody fragment thereof, described herein refers to a polypeptide that has a similar secondary, tertiary or quaternary structure of a CK-B4 polypeptide, a fragment of a CK-B4 polypeptide, an anti-CK-B4 antibody, or antibody fragment thereof, described herein. The structure of a polypeptide can determined by methods known to those skilled in the art, including but not limited to, X-ray crystallography, nuclear magnetic resonance, and crystallographic electron microscopy. Preferably, a variant CK-B4 polypeptide, a variant fragment of a CK-B4 polypeptide, or a variant anti-CK-B4 antibody and/or antibody fragment possesses similar or identical function and/or structure as the reference CK-B4 polypeptide, the reference fragment of a CK-B4 polypeptide, or the reference anti-CK-B4 antibody and/or antibody fragment, respectively.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264-2268 (1990), modified as in Karlin and Altschul *Proc. Natl. Acad. Sci. USA* 90:5873-5877 (1993). The BLASTn and BLASTx programs of Altschul, et al. *J. Mol. Biol.* 215:403-410 (1990) have incorporated such an alogrithm. BLAST nucleotide searches can be performed with the BLASTn program (score=100, wordlength=12) to obtain nucleotide sequences homologous to a nucleic acid molecules of the invention. BLAST protein searches can be performed with the BLASTX program (score=50, wordlength=3) to obtain amino acid sequences homologous to a protein molecules of the invention. To obtain gapped alignments for comparison purposes, Gapped BLAST can be utilized as described in Altschul et al. *Nucleic Acids Res.* 25:3589-3402(1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti *Comput. Appl. Biosci.*, 10:3-5 (1994); and FASTA described in Pearson and Lipman *Proc. Natl. Acad. Sci.* 85:2444-8 (1988). Within FASTA, ktup is a control option that sets the sensitivity and speed of the search.

The term "derivative" as used herein, refers to a variant polypeptide of the invention that comprises, or alternatively consists of, an amino acid sequence of a CK-B4 polypeptide, a fragment of a CK-B4 polypeptide, or an antibody of the invention that specifically binds to a CK-B4 polypeptide, which has been altered by the introduction of amino acid residue substitutions, deletions or additions. The term "derivative" as used herein also refers to a CK-B4 polypeptide, a fragment of a CK-B4 polypeptide, or an antibody that specifically binds to a CK-B4 polypeptide which has been modified, e.g., by the covalent attachment of any type of molecule to the polypeptide. For example, but not by way of limitation, a CK-B4 polypeptide, a fragment of a CK-B4 polypeptide, or an anti-CK-B4 antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a CK-B4 polypeptide, a fragment of a CK-B4 polypeptide, or an anti-CK-B4 antibody, may be modified by chemical modifications using techniques known to those of skill in the art, including, but not limited to, specific chemical cleavage, acetylation, formylation, metabolic synthesis of tunicamycin, etc. Further, a derivative of a CK-B4 polypeptide, a fragment of a CK-B4 polypeptide, or an anti-CK-B4 antibody, may contain one or more non-classical amino acids. A polypeptide derivative possesses a similar or identical function as a CK-B4 polypeptide, a fragment of a CK-B4 polypeptide, or an anti-CK-B4 antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, or at least 90 amino acid residues, of the amino acid sequence of CK-B4, or an anti-CK-B4 antibody (including molecules such as scFv's, that comprise, or alternatively consist of, antibody fragments or variants thereof) that specifically binds to CK-B4.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hypervariable regions, also called complementarity determining regions or CDRs. The CDRs from the heavy and the ligt chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J Immunol.* 148:1547 1553 (1992). In addition, bispecific antibodies may be formed as "diabodies" (Holliger et al. "Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int. J. Cancer Suppl.* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-CK-B4 Antibodies

Using phage display technology, single chain antibody molecules ("scFvs") have been identified that specifically bind to CK-B4 (or fragments or variants thereof). Molecules comprising, or alternatively consisting of, fragments or variants of these scFvs (e.g., including VH domains, VH CDRs, VL domains, or VL CDRs having an amino acid sequence of any one of those referred to in Table 1), that specifically bind to CK-B4 (or fragments or variants thereof) are also encompassed by the invention, as are nucleic acid molecules that encode these scFvs, and/or molecules.

Accordingly, in one embodiment, the invention provides antibodies that comprise the VH and VL domains of scFvs of the invention.

In a preferred embodiment, an antibody of the invention is an antibody expressed by any one of the cell lines disclosed in Table 1.

TABLE 1 scFvs that Specifically bind to CK-B4

| ScFv | scFv DNA SEQ ID NO: | scFv Protein SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC Deposit Number | ATCC Deposit Date |
|---|---|---|---|---|---|---|---|---|---|---|---|---|---|
| F003A09 | 3 | 20 | 1-121 | 26-35 | 50-66 | 99-110 | 138-250 | 159-172 | 188-194 | 227-239 | | | |
| F081C09 | 4 | 21 | 1-119 | 26-35 | 50-66 | 99-108 | 135-245 | 157-169 | 185-191 | 224-234 | | | |
| F076F10 | 5 | 22 | 1-123 | 26-35 | 50-66 | 99-112 | 140-250 | 162-174 | 190-196 | 229-239 | | | |
| F002D07 | 6 | 23 | 1-118 | 26-35 | 50-66 | 99-107 | 136-245 | 156-169 | 185-191 | 224-234 | | | |
| F076C06 | 7 | 24 | 1-125 | 26-35 | 50-66 | 99-114 | 142-252 | 164-176 | 192-198 | 231-241 | | | |
| F003B07 | 8 | 25 | 1-125 | 26-35 | 50-66 | 99-114 | 142-253 | 164-177 | 193-198 | 232-242 | | | |
| F003F01 | 9 | 26 | 1-120 | 26-35 | 50-66 | 99-109 | 142-248 | 159-171 | 187-193 | 226-237 | | | |
| F002G03 | 10 | 27 | 1-125 | 26-35 | 50-66 | 99-114 | 141-248 | 164-174 | 190-196 | 229-237 | | | |
| F003E11 | 11 | 28 | 1-121 | 26-35 | 50-66 | 99-110 | 138-249 | 160-172 | 188-194 | 227-238 | | | |
| F003F09 | 12 | 29 | 1-121 | 26-35 | 50-66 | 99-110 | 139-250 | 161-173 | 189-195 | 228-239 | | | |
| F003G02 | 13 | 30 | 1-120 | 26-35 | 50-66 | 99-109 | 137-247 | 159-171 | 187-193 | 226-236 | | | |
| F002C08 | 14 | 31 | 1-120 | 26-35 | 50-66 | 99-109 | 136-246 | 158-170 | 185-192 | 225-235 | | | |
| F002E03 | 15 | 32 | 1-124 | 26-35 | 50-66 | 99-113 | 140-247 | 163-173 | 189-195 | 228-236 | | | |
| F002D02 | 16 | 33 | 1-121 | 26-35 | 50-66 | 99-110 | 137-247 | 159-171 | 187-193 | 226-236 | | | |
| F076D02 | 17 | 34 | 1-121 | 26-35 | 50-66 | 99-110 | 138-249 | 160-172 | 188-194 | 227-238 | | | |
| F075G06 | 18 | 35 | 1-125 | 26-35 | 50-66 | 99-114 | 142-252 | 164-176 | 192-198 | 231-241 | | | |
| F076G06 | 19 | 36 | 1-121 | 26-35 | 50-66 | 99-110 | 138-249 | 160-172 | 188-194 | 227-238 | | | |

In particular, the invention relates to scFvs comprising, or alternatively consisting of the amino acid sequence of any one of SEQ ID NOs:20-36, referred to in Table 1 below. Molecules comprising, or alternatively consisting of, fragments or variants (e.g., including VH domains, VH CDRs, VL domains, or VL CDRs identified in Table 1) of the scFvs referred to in Table 1, that specifically bind to CK-B4 are also encompassed by the invention, as are nucleic acid molecules that encode these scFvs, and/or molecules (e.g., SEQ ID NOs:3-19).

ScFvs corresponding to SEQ ID NOs: 20-36 were selected for their ability bind CK-B4 polypeptide.

The present invention provides antibodies (including molecules comprising, or alternatively consisting of, antibody fragments or variants thereof) that specifically bind to a polypeptide or a polypeptide fragment of CK-B4. In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 2 below.

Cell lines that express IgG1 antibodies that comprise the VH and VL domains of scFvs of the invention have been deposited with the American Type Culture Collection ("ATCC") on the dates listed in Table 1 and given the ATCC Deposit Numbers identified in Table 1. The ATCC is located at 10801 University Boulevard, Manassas, Va. 20110-2209, USA. The ATCC deposit was made pursuant to the terms of the Budapest Treaty on the International Recognition of the Deposit of Microorganisms for Purposes of Patent Procedure.

The present invention encompasses antibodies (including molecules comprising, or alternatively consisting of, antibody fragments or variants thereof) that specifically bind to a CK-B4 polypeptide or a fragment, variant, or fusion protein thereof. A CK-B4 polypeptide includes, but is not limited to, CK-B4 (SEQ ID NO:2) or the polypeptide encoded by the cDNA contained in ATCC Deposit No. 75848 on Jul. 29, 1994. CK-B4 may be produced through recombinant expression of nucleic acids encoding the polypeptides of SEQ ID NO:2 (e.g., the cDNA in ATCC Deposit Number 75848). Antibodies of the invention may specifically bind CK-B4 as well as fragments and variants thereof, and are described in more detail below.

CK-B4 Polypeptides

In certain embodiments of the present invention, the antibodies of the present invention bind CK-B4 polypeptide, or fragments or variants thereof. The following section describes the CK-B4 polypeptides, fragments and variants that antibodies of the invention may bind in more detail. CK-B4 polypeptides which the antibodies of the invention may bind are described in more detail in International Publication Number WO 96/05856, WO97/31098 and U.S. Pat. No. 5,981,230 each of which are herein incorporated by reference in their entireties.

In certain embodiments, the antibodies of the present invention specifically bind CK-B4 polypeptide. An antibody that specifically binds CK-B4 may, in some embodiments, bind fragments, variants (including species orthologs and allelic variants of CK-B4), multimers or modified forms of CK-B4. For example, an antibody specific for CK-B4 may bind the CK-B4 moiety of a fusion protein comprising all or a portion of CK-B4.

CK-B4 proteins may be found as monomers or multimers (i.e., dimers, trimers, tetramers, and higher multimers). Accordingly, the present invention relates to antibodies that bind CK-B4 proteins found as monomers or as part of multimers. In specific embodiments, antibodies of the invention bind CK-B4 monomers, dimers, trimers or tetramers. In additional embodiments, antibodies of the invention bind at least dimers, at least trimers, or at least tetramers containing one or more CK-B4 polypeptides.

Antibodies of the invention may bind CK-B4 homomers or heteromers. As used herein, the term homomer, refers to a multimer containing only CK-B4 proteins of the invention (including CK-B4 fragments, variants, and fusion proteins, as described herein). These homomers may contain CK-B4 proteins having identical or different polypeptide sequences. In a specific embodiment, a homomer of the invention is a multimer containing only CK-B4 proteins having an identical polypeptide sequence. In another specific embodiment, antibodies of the invention bind CK-B4 homomers containing CK-B4 proteins having different polypeptide sequences. In specific embodiments, antibodies of the invention bind a CK-B4 homodimer (e.g., containing CK-B4 proteins having identical or different polypeptide sequences) or a homotrimer (e.g., containing CK-B4 proteins having identical or different polypeptide sequences). In additional embodiments, antibodies of the invention bind at least a homodimer, at least a homotrimer, or at least a homotetramer of CK-B4.

As used herein, the term heteromer refers to a multimer containing heterologous proteins (i.e., proteins containing polypeptide sequences that do not correspond to a polypeptide sequences encoded by a gene encoding CK-B4) in addition to the CK-B4 proteins of the invention. In a specific embodiment, antibodies of the invention bind a heterodimer, a heterotrimer, or a heterotetramer. In additional embodiments, the antibodies of the invention bind at least a heterodimer, at least a heterotrimer, or at least a heterotetramer containing one or more CK-B4 polypeptides.

Antibodies of the invention may bind CK-B4 multimers that are the result of hydrophobic, hydrophilic, ionic and/or covalent associations and/or may be indirectly linked, by for example, liposome formation. Thus, in one embodiment, antibodies of the invention may bind multimers, such as, for example, homodimers or homotrimers, are formed when CK-B4 proteins contact one another in solution. In another embodiment, antibodies of the invention may bind heteromultimers, such as, for example, heterotrimers or heterotetramers, that are formed when proteins of the invention contact antibodies to the CK-B4 polypeptides (including antibodies to the heterologous polypeptide sequence in a fusion protein) in solution. In other embodiments, multimers that one or more antibodies of the invention may bind are formed by covalent associations with and/or between the CK-B4 proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA clone of ATCC Deposit 75848). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a CK-B4 fusion protein. In one example, covalent associations are between the heterologous sequence contained in a fusion protein (see, e.g., U.S. Pat. No. 5,478,925). In a specific example, the covalent associations are between the heterologous sequence contained in a CK-B4-Fc fusion protein (as described herein). In another specific example, covalent associations of fusion proteins are between heterologous polypeptide sequences from another chemokine family ligand/receptor member that is capable of forming covalently associated multimers, such as for example, MIP-1β and/or MIP-1α (see, e.g., Guan et al., J. Biol. Chem. 276:12404-12409 (2001)).

Antibodies of the invention may bind CK-B4 multimers that were generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more intermolecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that one or more antibodies of the invention may bind (see, e.g., U.S. Pat. No. 5,478,925, which is herein incorporated by reference in its entirety).

Alternatively, antibodies of the invention may bind CK-B4 polypeptide multimers generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a CK-B4 polypeptide to a sequence encoding a linker polypeptide and then further to a synthetic polynucleotide encoding the translated product of the polypeptide in the reverse orientation from the original C-terminus to the N-terminus (see, e.g., U.S. Pat. No. 5,478,925, which is herein incorporated by reference in its entirety). In another embodiment, recombinant techniques described herein or otherwise known in the art are applied to generate recombinant CK-B4 polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more CK-B4 polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple CK-B4 polypeptides separated by peptide linkers may be produced using conventional recombinant DNA technology. In specific embodiments, antibodies of the invention bind proteins comprising multiple CK-B4 polypeptides separated by peptide linkers.

Another method for preparing multimer CK-B4 polypeptides involves use of CK-B4 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric CK-B4 proteins are those described in PCT application WO 94/10308, hereby incorporated by reference. Recombinant fusion proteins comprising a soluble CK-B4 polypeptide fused to a peptide that dimerizes or trimerizes in solution are expressed in suitable host cells, and the resulting soluble multimeric CK-B4 is recovered from the culture supernatant using techniques known in the art. In specific embodiments, antibodies of the invention bind CK-B4-leucine zipper fusion protein monomers and/or CK-B4-leucine zipper fusion protein multimers.

Certain members of the chemokine family of proteins are believed to exist in dimeric form (Clore and Gronenborn, FASEB J. 9:57-62, 1995). Thus, dimeric CK-B4 may offer the advantage of enhanced biological activity. Preferred leucine zipper moieties are those that preferentially form dimers. In specific embodiments, antibodies of the invention bind CK-B4-leucine zipper fusion protein dimers.

Other peptides derived from naturally occurring dimeric proteins may be employed in preparing dimeric CK-B4. In specific embodiments, antibodies of the invention bind CK-B4-fusion protein monomers and/or CK-B4 fusion protein dimers.

Antibodies that bind CK-B4 may bind them as isolated polypeptides, in their naturally occurring state, and/or their native conformation. For example, antibodies of the present invention may bind recombinantly produced CK-B4.

Antibodies of the present invention may also bind CK-B4 purified from a cell culture, wherein said CK-B4 polypeptide is encoded by a polynucleotide encoding amino acids 1 to 96 of SEQ ID NO:2 operably associated with a regulatory sequence that controls expression of said polynucleotide.

Antibodies of the present invention may bind CK-B4 polypeptide fragments comprising or alternatively, consisting of, an amino acid sequence contained in SEQ ID NO:2, encoded by the cDNA contained in ATCC deposit Number 75848, or encoded by nucleic acids which hybridize (e.g., under stringent hybridization conditions) to the nucleotide sequence contained in ATCC deposit Number 75848, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 23, 24 to 43, 44 to 63, 64 to 83, and/or 84 to 96 of SEQ ID NO:2. In this context "about" includes the particularly recited value, larger or smaller by several (5, 4, 3, 2, or 1) amino acids, at either extreme or at both extremes. Moreover, polypeptide fragments that antibodies of the invention may bind can be at least about 10, 20, 30, 40, 50, 60, 70, 80, or 90 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising, or alternatively consisting of, a fragment of the predicted mature CK-B4 polypeptide (predicted to constitute amino acid residues from about 25 to about 96 in SEQ ID NO:2), wherein the fragment has a CK-B4 functional activity (e.g., antigenic activity or biological acitivity); a polypeptide comprising, or alternatively consisting of, 1, 2, 3, or 4 of the conserved cyteine residues of the CK-B4 protein (predicted to constitute amino acid residues 32, 33, 58 and 74 in SEQ ID NO:2); and a polypeptide comprising, or alternatively, consisting of, one, two, three, four or more, epitope bearing portions of the CK-B4 protein. In additional embodiments, the polypeptide fragments of the invention comprise, or alternatively, consist of, any combination of 1, 2, or all 3 of the above members. Polynucleotides encoding these polypeptides are also encompassed by the invention.

In highly preferred embodiments, the antibodies of the invention that bind CK-B4 prevent a CK-B4 receptor (e.g., CCR6) from binding to CK-B4. In other highly preferred embodiments, the antibodies of the invention that bind CK-B4 antagonize or neutralize CK-B4. In other highly preferred embodiments, the antibodies of the invention that bind CK-B4 inhibit chemotaxis of the cells expressing a CK-B4 receptor (e.g., T cells, B cells, dendritic cells). In other highly preferred embodiments, the antibodies of the invention that bind CK-B4 stimulate chemotaxis of the cells expressing a CK-B4 receptor (e.g., T cells, B cells, dendritic cells).

Antibodies of the invention may also bind fragments comprising, or alternatively, consisting of structural or functional attributes of CK-B4. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) CK-B4. Certain preferred regions are those set out in Table 2 and include, but are not limited to, regions of the aforementioned types identified by analysis of the amino acid sequence depicted in (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of CK-B4 set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column III represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions; Column VIII represents a Kyte-Doolittle hydrophilicity plot; Column; Column IX represents a Hopp-Woods hydrophobicity plot; Column X represents the results of an Eisenberg analysis of alpha amphipathic regions; Column XI represents the results of an Eisenberg analysis of beta amphipathic regions; Column XII represents the results of a Karplus-Schultz analysis of flexible regions; Column XIII represents the Jameson-Wolf antigenic index score; and Column XIV represents the Emini surface probability plot.

In a preferred embodiment, the data presented in columns VIII, XIII, and XIV of Table 2 can be used to determine regions of CK-B4 which exhibit a high degree of potential for antigenicity. Regions of high antigenicity are determined from the data presented in columns VIII, XIII, and/or XIV by choosing values which represent regions of the polypeptide which are likely to be exposed on the surface of the polypeptide in an environment in which antigen recognition may occur in the process of initiation of an immune response.

The above-mentioned preferred regions set out in Table 2 include, but are not limited to, regions of the aforementioned types identified by analysis of the amino acid sequence set out in SEQ ID NO:2. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments bound by one or more antibodies of the invention are those that comprise regions of CK-B4 that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | −0.26 | 0.53 | . | . | . | −0.40 | 0.15 |
| Cys | 2 | A | . | . | . | . | . | . | −0.17 | 0.10 | . | . | . | −0.10 | 0.24 |
| Cys | 3 | A | . | . | . | . | T | . | −0.59 | 0.06 | . | . | . | 0.10 | 0.25 |
| Thr | 4 | A | . | . | . | . | T | . | −1.01 | 0.31 | . | . | . | 0.10 | 0.21 |
| Lys | 5 | A | . | . | . | . | T | . | −1.43 | 0.39 | . | . | F | 0.25 | 0.32 |
| Ser | 6 | A | . | . | . | . | T | . | −1.42 | 0.50 | . | . | F | −0.05 | 0.50 |
| Leu | 7 | A | A | . | . | . | . | . | −1.34 | 0.43 | . | . | . | −0.60 | 0.35 |
| Leu | 8 | A | A | . | . | . | . | . | −1.49 | 0.44 | . | . | . | −0.60 | 0.18 |
| Leu | 9 | A | A | . | . | . | . | . | −1.78 | 1.13 | . | . | . | −0.60 | 0.11 |
| Ala | 10 | A | A | . | . | . | . | . | −2.12 | 1.36 | . | . | . | −0.60 | 0.13 |
| Ala | 11 | A | A | . | . | . | . | . | −2.68 | 1.06 | . | . | . | −0.60 | 0.21 |
| Leu | 12 | A | A | . | . | . | . | . | −2.68 | 1.01 | . | . | . | −0.60 | 0.19 |
| Met | 13 | A | A | . | . | . | . | . | −2.68 | 1.01 | . | . | . | −0.60 | 0.16 |
| Ser | 14 | A | A | . | . | . | . | . | −2.68 | 1.20 | . | . | . | −0.60 | 0.13 |
| Val | 15 | A | A | . | . | . | . | . | −2.12 | 1.39 | . | . | . | −0.60 | 0.13 |
| Leu | 16 | A | A | . | . | . | . | . | −2.34 | 1.20 | . | . | . | −0.60 | 0.17 |
| Leu | 17 | A | A | . | . | . | . | . | −2.20 | 1.27 | . | . | . | −0.60 | 0.11 |
| Leu | 18 | A | A | . | . | . | . | . | −1.94 | 1.46 | . | . | . | −0.60 | 0.08 |
| His | 19 | A | A | . | . | . | . | . | −1.64 | 1.24 | . | . | . | −0.60 | 0.09 |
| Leu | 20 | A | A | . | . | . | . | . | −1.09 | 0.56 | . | * | . | −0.60 | 0.19 |
| Cys | 21 | A | . | . | . | . | T | . | −0.28 | 0.26 | . | * | . | 0.10 | 0.32 |
| Gly | 22 | A | . | . | . | . | T | . | −0.06 | −0.43 | . | * | F | 0.85 | 0.40 |
| Glu | 23 | A | . | . | . | . | T | . | 0.17 | −0.43 | . | * | F | 0.85 | 0.49 |
| Ser | 24 | A | . | . | . | . | T | . | −0.10 | −0.61 | . | * | F | 1.15 | 0.93 |
| Glu | 25 | A | . | . | . | . | . | . | 0.71 | −0.80 | . | * | F | 1.10 | 1.26 |
| Ala | 26 | A | . | . | . | . | . | . | 0.68 | −0.83 | . | * | F | 1.10 | 1.17 |
| Ala | 27 | A | . | . | . | . | . | . | 1.02 | −0.04 | . | * | . | 0.50 | 0.76 |
| Ser | 28 | A | . | . | . | . | . | . | 0.36 | −0.43 | . | * | . | 0.50 | 0.73 |
| Asn | 29 | A | . | . | . | . | T | . | −0.01 | 0.14 | * | * | . | 0.10 | 0.39 |
| Phe | 30 | A | . | . | . | . | T | . | −0.82 | 0.21 | * | * | . | 0.10 | 0.21 |
| Asp | 31 | . | . | . | . | T | T | . | −0.58 | 0.40 | . | * | . | 0.50 | 0.13 |
| Cys | 32 | . | . | . | . | T | T | . | −0.23 | 0.44 | . | * | . | 0.20 | 0.08 |
| Cys | 33 | . | . | . | B | T | . | . | −0.24 | 0.80 | . | * | . | −0.20 | 0.14 |
| Leu | 34 | . | . | . | B | T | . | . | −0.24 | 0.50 | * | * | . | −0.20 | 0.12 |
| Gly | 35 | . | . | . | B | T | . | . | 0.57 | 0.50 | * | * | . | −0.20 | 0.38 |
| Tyr | 36 | . | . | . | . | T | T | . | −0.32 | −0.07 | * | * | . | 1.25 | 1.38 |
| Thr | 37 | A | . | . | . | . | T | . | −0.47 | 0.04 | * | . | . | 0.25 | 1.18 |
| Asp | 38 | A | . | . | . | . | T | . | 0.17 | 0.04 | * | . | . | 0.10 | 0.98 |
| Arg | 39 | A | . | . | . | . | T | . | 0.77 | 0.11 | . | . | . | 0.10 | 0.85 |
| Ile | 40 | A | . | . | . | . | . | . | 1.16 | −0.21 | . | . | . | 0.50 | 0.91 |
| Leu | 41 | A | . | . | . | . | . | . | 0.70 | −0.70 | . | . | . | 0.95 | 1.09 |
| His | 42 | . | . | . | . | . | T | C | 0.12 | 0.09 | . | . | . | 0.30 | 0.48 |
| Pro | 43 | . | . | . | . | . | T | C | −0.73 | 0.77 | . | . | . | 0.00 | 0.48 |
| Lys | 44 | . | . | . | . | T | T | . | −1.19 | 0.73 | . | * | . | 0.20 | 0.43 |
| Phe | 45 | . | . | B | . | . | T | . | −1.00 | 0.47 | . | * | . | −0.20 | 0.32 |
| Ile | 46 | . | . | B | B | . | . | . | −0.50 | 0.76 | * | * | . | −0.60 | 0.18 |
| Val | 47 | . | . | B | B | . | . | . | −0.36 | 0.81 | * | . | . | −0.60 | 0.13 |
| Gly | 48 | . | . | B | B | . | . | . | −0.14 | 0.81 | * | . | . | −0.60 | 0.29 |
| Phe | 49 | A | . | B | B | . | . | . | −1.00 | 0.43 | * | . | . | −0.60 | 0.71 |
| Thr | 50 | A | . | . | B | . | . | . | −0.89 | 0.43 | * | . | . | −0.60 | 0.79 |
| Arg | 51 | A | . | . | B | . | . | . | 0.00 | 0.29 | * | . | F | −0.15 | 0.81 |
| Gln | 52 | . | . | . | B | . | . | C | 0.86 | 0.26 | * | . | F | 0.20 | 1.50 |
| Leu | 53 | . | . | . | B | . | . | C | 0.86 | −0.53 | * | . | . | 0.95 | 1.80 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 54 | . | . | . | B | T | . | . | 0.89 | −0.59 | * | . | F | 1.43 | 0.91 |
| Asn | 55 | . | . | . | . | T | T | . | 1.20 | −0.01 | * | . | F | 1.81 | 0.28 |
| Glu | 56 | . | . | . | . | T | T | . | 0.20 | −0.41 | * | * | F | 2.09 | 0.57 |
| Gly | 57 | . | . | . | . | T | T | . | 0.20 | −0.41 | * | * | F | 2.37 | 0.40 |
| Cys | 58 | . | . | . | . | T | T | . | 0.42 | −0.51 | . | . | . | 2.80 | 0.40 |
| Asp | 59 | A | . | . | . | . | . | . | 0.12 | −0.41 | . | * | . | 1.62 | 0.23 |
| Ile | 60 | A | . | . | B | . | . | . | −0.77 | 0.27 | . | . | . | 0.54 | 0.16 |
| Asn | 61 | A | . | . | B | . | . | . | −1.47 | 0.53 | . | . | . | −0.04 | 0.21 |
| Ala | 62 | A | . | . | B | . | . | . | −1.16 | 0.74 | . | . | . | −0.32 | 0.11 |
| Ile | 63 | A | . | . | B | . | . | . | −0.80 | 1.24 | . | * | . | −0.60 | 0.22 |
| Ile | 64 | A | . | . | B | . | . | . | −0.76 | 1.04 | * | . | . | −0.60 | 0.19 |
| Phe | 65 | A | . | . | B | . | . | . | 0.18 | 0.64 | . | * | . | −0.60 | 0.38 |
| His | 66 | A | . | . | B | . | . | . | 0.22 | 0.14 | . | * | . | −0.15 | 1.09 |
| Thr | 67 | A | . | . | B | . | . | . | 0.00 | −0.54 | . | * | F | 0.90 | 3.12 |
| Lys | 68 | A | . | . | B | . | . | . | 0.59 | −0.54 | . | * | F | 0.90 | 2.97 |
| Lys | 69 | . | . | . | . | T | . | . | 0.62 | −0.94 | . | * | F | 1.50 | 2.92 |
| Lys | 70 | . | . | . | B | T | . | . | 0.66 | −0.80 | . | * | F | 1.30 | 1.50 |
| Leu | 71 | A | . | . | B | . | . | . | 0.10 | −0.71 | . | * | . | 0.60 | 0.40 |
| Ser | 72 | A | . | . | B | . | . | . | 0.41 | −0.21 | . | * | . | 0.30 | 0.20 |
| Val | 73 | A | . | . | B | . | . | . | 0.16 | 0.19 | . | * | . | −0.02 | 0.16 |
| Cys | 74 | . | . | . | B | T | . | . | 0.16 | 0.61 | . | * | . | 0.36 | 0.31 |
| Ala | 75 | A | . | . | B | T | . | C | 0.11 | −0.07 | . | * | . | 1.54 | 0.46 |
| Asn | 76 | . | . | . | . | . | T | C | 0.61 | −0.06 | . | * | F | 2.32 | 1.07 |
| Pro | 77 | . | . | . | . | T | T | . | 0.62 | −0.21 | . | * | F | 2.80 | 2.88 |
| Lys | 78 | . | . | . | . | T | T | . | 0.62 | 0.13 | . | * | F | 1.92 | 3.00 |
| Gln | 79 | A | . | . | . | . | T | . | 1.33 | 0.27 | . | . | F | 1.24 | 1.38 |
| Thr | 80 | . | . | . | B | T | . | . | 1.68 | −0.13 | * | . | F | 1.56 | 1.79 |
| Trp | 81 | A | . | . | B | . | . | . | 0.79 | 0.20 | * | . | F | 0.28 | 1.40 |
| Val | 82 | . | . | B | B | . | . | . | 0.14 | 0.89 | * | * | . | −0.60 | 0.57 |
| Lys | 83 | . | . | B | B | . | . | . | 0.21 | 1.13 | * | * | . | −0.60 | 0.29 |
| Tyr | 84 | . | . | B | B | . | . | . | −0.60 | 0.64 | * | * | . | −0.60 | 0.54 |
| Ile | 85 | . | . | B | B | . | . | . | −1.10 | 0.41 | * | * | . | −0.60 | 0.60 |
| Val | 86 | A | . | . | B | . | . | . | −1.11 | 0.46 | * | * | . | −0.60 | 0.25 |
| Arg | 87 | A | . | . | B | . | . | . | −0.21 | 0.84 | * | * | . | −0.60 | 0.21 |
| Leu | 88 | A | . | . | B | . | . | . | −0.21 | 0.09 | * | * | . | −0.30 | 0.61 |
| Leu | 89 | A | . | . | B | . | . | . | −0.82 | −0.60 | * | * | . | 0.75 | 1.64 |
| Ser | 90 | A | . | . | B | . | . | . | 0.11 | −0.60 | * | . | F | 0.75 | 0.62 |
| Lys | 91 | A | . | . | B | . | . | . | 0.97 | −0.60 | * | * | F | 0.90 | 1.50 |
| Lys | 92 | A | A | . | . | . | . | . | 0.26 | −0.89 | * | . | F | 0.90 | 2.93 |
| Val | 93 | A | A | . | . | . | . | . | 0.68 | −0.96 | * | . | F | 0.90 | 2.17 |
| Lys | 94 | A | A | . | . | . | . | . | 1.10 | −0.91 | * | . | . | 0.75 | 1.38 |
| Asn | 95 | A | A | . | . | . | . | . | 1.01 | −0.49 | * | . | . | 0.30 | 0.88 |
| Met | 96 | A | A | . | . | . | . | . | 0.58 | −0.06 | * | . | . | 0.45 | 1.52 |

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins nor to the amino or carboxyl terminals.

Antigenic epitope-bearing peptides and polypeptides are therefore useful to raise antibodies, including monoclonal antibodies, that bind to a CK-B4 polypeptide of the invention. See, for instance, Wilson et al., *Cell* 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:2.

Antibodies of the invention may bind one or more antigenic CK-B4 polypeptides or peptides including, but not limited to: a polypeptide comprising amino acid residues from about 55 to about 59 of SEQ ID NO:2; and/or a polypeptide comprising amino acid residues from about 75 to about 78 of SEQ ID NO:2. In this context "about" includes the particularly recited range, larger or smaller by several (5, 4, 3, 2, or 1) amino acids, at either terminus or at both termini. Epitope-bearing CK-B4 peptides and polypeptides may be produced by any conventional means. Houghten, R. A., "General method for the rapid solid-phase synthesis of large numbers of peptides: specificity of antigen-antibody interaction at the level of individual amino acids," *Proc. Natl. Acad. Sci. USA* 82:5131-5135 (1985).

This "Simultaneous Multiple Peptide Synthesis (SMPS)" process is further described in U.S. Pat. No. 4,631,211 to Houghten et al. (1986).

As one of skill in the art will appreciate, CK-B4 polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric CK-B4 protein or protein fragment alone (Fountoulakis et al., *J Biochem* 270:3958-3964 (1995)). Thus, antibodies of the invention may bind fusion proteins that comprise all or a portion of a CK-B4 polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified CK-B4 polypeptides or CK-B4 polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., *J. Biol. Chem.*, 268:2984-2988 (1993) reported modified KGF proteins that had heparin binding activity even if 3, 8, or 27 amino-terminal amino acid residues were missing However, even if deletion of one or more amino acids from the N-terminus of a protein results in modification or loss of one or more biological functions of the protein, other functional activities (e.g., biological activities, ability to multimerize, ability to bind a CK-B4 receptor (e.g., CCR6)) may still be retained. For example, the ability of shortened CK-B4 polypeptides to induce and/or bind to antibodies which recognize the complete or mature forms of the CK-B4 polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a CK-B4 polypeptide with a large number of deleted N-terminal amino acid residues may retain some biological or immunogenic activities. In fact, peptides composed of as few as six CK-B4 amino acid residues may often evoke an immune response.

Accordingly, the present invention further provides antibodies that bind polypeptides having one or more residues deleted from the amino terminus of the CK-B4 amino acid sequence of SEQ ID NO:2 up to the lysine residue at position number 91 and polynucleotides encoding such polypeptides. In particular, the present invention provides antibodies that bind polypeptides comprising the amino acid sequence of residues $n^1$-96 of SEQ ID NO:2, where $n^1$ is an integer from 2 to 91 corresponding to the position of the amino acid residue in SEQ ID NO:2.

More in particular, the invention provides antibodies that bind polypeptides comprising, or alternatively consisting of, the amino acid sequence of residues of C-2 to M-96; C-3 to M-96; T-4 to M-96; K-5 to M-96; S-6 to M-96; L-7 to M-96; L-8 to M-96; L-9 to M-96; A-10 to M-96; A-11 to M-96; L-12 to M-96; M-13 to M-96; S-14 to M-96; V-15 to M-96; L-16 to M-96; L-17 to M-96; L-18 to M-96; H-19 to M-96; L-20 to M-96; C-21 to M-96; G-22 to M-96; E-23 to M-96; S-24 to M-96; E-25 to M-96; A-26 to M-96; A-27 to M-96; S-28 to M-96; N-29 to M-96; F-30 to M-96; D-31 to M-96; C-32 to M-96; C-33 to M-96; L-34 to M-96; G-35 to M-96; Y-36 to M-96; T-37 to M-96; D-38 to M-96; R-39 to M-96; I-40 to M-96; L-41 to M-96; H-42 to M-96; P-43 to M-96; K-44 to M-96; F-45 to M-96; I-46 to M-96; V-47 to M-96; G-48 to M-96; F-49 to M-96; T-50 to M-96; R-51 to M-96; Q-52 to M-96; L-53 to M-96; A-54 to M-96; N-55 to M-96; E-56 to M-96; G-57 to M-96; C-58 to M-96; D-59 to M-96; I-60 to M-96; N-61 to M-96; A-62 to M-96; I-63 to M-96; I-64 to M-96; F-65 to M-96; H-66 to M-96; T-67 to M-96; K-68 to M-96; K-69 to M-96; K-70 to M-96; L-71 to M-96; S-72 to M-96; V-73 to M-96; C-74 to M-96; A-75 to M-96; N-76 to M-96; P-77 to M-96; K-78 to M-96; Q-79 to M-96; T-80 to M-96; W-81 to M-96; V-82 to M-96; K-83 to M-96; Y-84 to M-96; I-85 to M-96; V-86 to M-96; R-87 to M-96; L-88 to M-96; L-89 to M-96; S-90 to M-96; K-91 to M-96 of the CK-B4 sequence of SEQ ID NO:2.

As mentioned above, even if deletion of one or more amino acids from the C-terminus of a protein results in modification of loss of one or more biological functions of the protein, other functional activities (e.g., biological activities, ability to multimerize, ability to bind a CK-B4 receptor (e.g., CCR6)) may still be retained. For example the ability of the shortened CK-B4 polypeptide to induce and/or bind to antibodies which recognize the complete or mature forms of the CK-B4 polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a CK-B4 polypeptide with a large number of deleted C-terminal amino acid residues may retain some biological or immunogenic activities. In fact, peptides composed of as few as six CK-B4 amino acid residues may often evoke an immune response.

In another embodiment, antibodies of the invention bind C-terminal deletions of the CK-B4 polypeptide that can be described by the general formula 1-$m^1$ where $m^1$ is a number from 6 to 95 corresponding to the amino acid sequence identified of SEQ ID NO:2. In specific embodiments, the invention provides antibodies that bind CK-B4 polypeptides comprising, or alternatively consisting of, the amino acid sequence of residues: M-1 to N-95; M-1 to K-94; M-1 to V-93; M-1 to K-92; M-1 to K-91; M-1 to S-90; M-1 to I-89; M-1 to L-88; M-1 to R-87; M-1 to V-86; M-1 to I-85; M-1 to Y-84; M-1 to K-83; M-1 to V-82; M-1 to W-81; M-1 to T-80; M-1 to Q-79; M-1 to K-78; M-1 to P-77; M-1 to N-76; M-1 to A-75; M-1 to C-74; M-1 to V-73; M-1 to S-72; M-1 to I-71; M-1 to K-70; M-1 to K-69; M-1 to K-68; M-1 to T-67; M-1 to H-66; M-1 to F-65; M-1 to I-64; M-1 to I-63; M-1 to A-62; M-1 to N-61; M-1 to I-60; M-1 to D-59; M-1 to C-58; M-1 to G-57; M-1 to E-56; M-1 to N-55; M-1 to A-54; M-1 to I-53; M-1 to Q-52; M-1 to R-51; M-1 to T-50; M-1 to F-49; M-1 to G-48; M-1 to V-47; M-1 to I-46; M-1 to F-45; M-1 to K-44; M-1 to P-43; M-1 to H-42; M-1 to L-41; M-1 to I-40; M-1 to R-39; M-1 to D-38; M-1 to T-37; M-1 to Y-36; M-1 to G-35; M-1 to L-34; M-1 to C-33; M-1 to C-32; M-1 to D-31; M-1 to F-30; M-1 to N-29; M-1 to S-28; M-1 to A-27; M-1 to A-26; M-1 to E-25; M-1 to S-24; M-1 to E-23; M-1 to G-22; M-1 to C-21; M-1 to I-20; M-1 to H-19; M-1 to L-18; M-1 to L-17; M-1 to L-16; M-1 to V-15; M-1 to S-14; M-1 to M-13; M-1 to I-12; M-1 to A-11; M-1 to A-10; M-1 to L-9; M-1 to I-8; M-1 to I-7 of the CK-B4 sequence of SEQ ID NO:2.

In another embodiment, antibodies of the invention bind C-terminal deletions of the CK-B4 polypeptide that can be described by the general formula 25-$m^2$ where $m^2$ is a number from 31 to 95 corresponding to the amino acid sequence identified of SEQ ID NO:2. In specific embodiments, the invention provides antibodies that bind CK-B4 polypeptides comprising, or alternatively consisting of, the amino acid sequence of residues: E-25 to N-95; E-25 to K-94; E-25 to V-93; E-25 to K-92; E-25 to K-91; E-25 to S-90; E-25 to L-89; E-25 to L-88; E-25 to R-87; E-25 to V-86; E-25 to I-85; E-25 to Y-84; E-25 to K-83; E-25 to V-82; E-25 to W-81; E-25 to T-80; E-25 to Q-79; E-25 to K-78; E-25 to P-77; E-25 to N-76; E-25 to A-75; E-25 to C-74; E-25 to V-73; E-25 to S-72; E-25 to L-71; E-25 to K-70; E-25 to K-69; E-25 to K-68; E-25 to T-67; E-25 to H-66; E-25 to F-65; E-25 to I-64; E-25 to I-63; E-25 to A-62; E-25 to N-61; E-25 to I-60; E-25 to D-59; E-25 to C-58; E-25 to G-57; E-25 to E-56; E-25 to N-55; E-25 to A-54; E-25 to L-53; E-25 to Q-52; E-25 to R-51; E-25 to T-50; E-25 to F-49; E-25 to G-48; E-25 to V-47; E-25 to I-46; E-25 to F-45; E-25 to K-44; E-25 to P-43; E-25 to H-42; E-25 to I-41; E-25 to I-40; E-25 to R-39; E-25 to D-38; E-25 to T-37; E-25 to Y-36; E-25 to G-35; E-25 to L-34; E-25 to C-33; E-25 to C-32; E-25 to D-31 of the CK-B4 sequence of SEQ ID NO:2.

The invention also provides antibodies that bind polypeptides having one or more amino acids deleted from both the amino and the carboxyl termini of a CK-B4 polypeptide, which may be described generally as having residues $n^1$-$m^1$ and/or $n^1$-$m^2$ of SEQ ID NO:2, where $n^1$, $m^1$, and $m^2$ are integers as described above.

Preferably, antibodies of the present invention bind fragments of CK-B4 comprising a portion of the mature protein; i.e., within residues 25-96 of SEQ ID NO:2.

It will be recognized in the art that some amino acid sequence of CK-B4 can be varied without significant effect of the structure or function of the protein. If such differences in sequence are contemplated, it should be remembered that there will be critical areas on the protein which determine activity. Such areas will usually comprise residues which make up the ligand binding site or which form tertiary structures which affect these domains.

Thus, the invention further includes antibodies that bind variations of the CK-B4 protein which show substantial CK-B4 protein activity or which include regions of CK-B4 such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:2, or that encoded by the cDNA in ATCC deposit 75848. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the CK-B4 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a CK-B4 that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:2 and/or any of the polypeptide fragments described herein is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

In specific embodiments, the antibodies of the invention bind CK-B4 polypeptides or fragments or variants thereof (especially a fragment comprising or alternatively consisting of, the mature form of CK-B4), that contains any one or more of the following conservative mutations in CK-B4: M1 replaced with A, G, I, L, S, T, or V; T4 replaced with A, G, I, L, S, M, or V; K5 replaced with H, or R; S6 replaced with A, G, I, L, T, M, or V; L7 replaced with A, G, I, S, T, M, or V; L8 replaced with A, G, I, S, T, M, or V; L9 replaced with A, G, I, S, T, M, or V; A10 replaced with G, I, L, S, T, M, or V; A11 replaced with G, I, L, S, T, M, or V; L12 replaced with A, G, I, S, T, M, or V; M13 replaced with A, G, I, L, S, T, or V; S14 replaced with A, G, I, L, T, M, or V; V15 replaced with A, G, I, L, S, T, or M; L16 replaced with A, G, I, S, T, M, or V; L17 replaced with A, G, I, S, T, M, or V; L18 replaced with A, G, I, S, T, M, or V; H19 replaced with K, or R; L20 replaced with A, G, I, S, T, M, or V; G22 replaced with A, I, L, S, T, M, or V; E23 replaced with D; S24 replaced with A, G, I, L, T, M, or V; E25 replaced with D; A26 replaced with G, I, L, S, T, M, or V; A27 replaced with G, I, L, S, T, M, or V; S28 replaced with A, G, I, L, T, M, or V; N29 replaced with Q; F30 replaced with W, or Y; D31 replaced with E; L34 replaced with A, G, I, S, T, M, or V; G35 replaced with A, I, L, S, T, M, or V; Y36 replaced with F, or W; T37 replaced with A, G, I, L, S, M, or V; D38 replaced with E; R39 replaced with H, or K; I40 replaced with A, G, L, S, T, M, or V; L41 replaced with A, G, I, S, T, M, or V; H42 replaced with K, or R; K44 replaced with H, or R; F45 replaced with W, or Y; I46 replaced with A, G, L, S, T, M, or V; V47 replaced with A, G, I, L, S, T, or M; G48 replaced with A, I, L, S, T, M, or V; F49 replaced with W, or Y; T50 replaced with A, G, I, L, S, M, or V; R51 replaced with H, or K; Q52 replaced with N; L53 replaced with A, G, I, S, T, M, or V; A54 replaced with G, I, L, S, T, M, or V; N55 replaced with Q; E56 replaced with D; G57 replaced with A, I, L, S, T, M, or V; D59 replaced with E; I60 replaced with A, G, L, S, T, M, or V; N61 replaced with Q; A62 replaced with G, I, L, S, T, M, or V; I63 replaced with A, G, L, S, T, M, or V; I64 replaced with A, G, L, S, T, M, or V; F65 replaced with W, or Y; H66 replaced with K, or R; T67 replaced with A, G, I, L, S, M, or V; K68 replaced with H, or R; K69 replaced with H, or R; K70 replaced with H, or R; L71 replaced with A, G, I, S, T, M, or V; S72 replaced with A, G, I, L, T, M, or V; V73 replaced with A, G, I, L, S, T, or M; A75 replaced with G, I, L, S, T, M, or V; N76 replaced with Q; K78 replaced with H, or R; Q79 replaced with N; T80 replaced with A, G, I, L, S, M, or V; W81 replaced with F, or Y; V82 replaced with A, G, I, L, S, T, or M; K83 replaced with H, or R; Y84 replaced with F, or W; I85 replaced with A, G, L, S, T, M, or V; V86 replaced with A, G, I, L, S, T, or M; R87 replaced with H, or K; L88 replaced with A, G, I, S, T, M, or V; L89 replaced with A, G, I, S, T, M, or V; S90 replaced with A, G, I, L, T, M, or V; K91 replaced with H, or R; K92 replaced with H, or R; V93 replaced with A, G, I, L, S, T, or M; K94 replaced with H, or R; N95 replaced with Q; M96 replaced with A, G, I, L, S, T, or V of SEQ ID NO:2.

In specific embodiments, the antibodies of the invention bind CK-B4 polypeptides or fragments or variants thereof (especially a fragment comprising or alternatively consisting of, the extracellular soluble domain of CK-B4), that contains any one or more of the following non-conservative mutations in CK-B4: M1 replaced with D, E, H, K, R, N, Q, F, W, Y, P, or C; C2 replaced with D, E, H, K, R, A, G, I, L, S, T, M, V, N, Q, F, W, Y, or P; C3 replaced with D, E, H, K, R, A, G, I, L, S, T, M, V, N, Q, F, W, Y, or P; T4 replaced with D, E, H, K, R, N, Q, F, W, Y, P, or C; K5 replaced with D, E, A, G, I, L, S, T, M, V, N, Q, F, W, Y, P, or C; S6 replaced with D, E, H, K, R, N, Q, F, W, Y, P, or C; L7 replaced with D, E, H, K, R, N, Q, F, W, Y, P, or C; L8 replaced with D, E, H, K, R, N, Q, F, W, Y, P, or C; L9 replaced with D, E, H, K, R, N, Q, F, W, Y, P, or C; A10 replaced with D, E, H, K, R, N, Q, F, W, Y, P, or C; A11 replaced with D, E, H, K, R, N, Q, F, W, Y, P, or C; L12 replaced with D, E, H, K, R, N, Q, F, W, Y, P, or C; M13 replaced with D, E, H, K, R, N, Q, F, W, Y, P, or C; S14 replaced with D, E, H, K, R, N, Q, F, W, Y, P, or C; V15 replaced with D, E, H, K, R, N, Q, F, W, Y, P, or C; L16 replaced with D, E, H, K, R, N, Q, F, W, Y, P, or C; L17 replaced with D, E, H, K, R, N, Q, F, W, Y, P, or C; L18 replaced with D, E, H, K, R, N, Q, F, W, Y, P, or C; H19 replaced with D, E, A, G, I, L, S, T, M, V, N, Q, F, W, Y, P, or C; L20 replaced with D, E, H, K, R, N, Q, F, W, Y, P, or C; C21 replaced with D, E, H, K, R, A, G, I, L, S, T, M, V, N, Q, F, W, Y, or P; G22 replaced with D, E, H, K, R, N, Q, F, W, Y, P, or C; E23 replaced with H, K, R, A, G, I, L, S, T, M, V, N, Q, F, W, Y, P, or C; S24 replaced with D, E, H, K, R, N, Q, F, W, Y, P, or C; E25 replaced with H, K, R, A, G, I, L, S, T, M, V, N, Q, F, W, Y, P, or C; A26 replaced with D, E, H, K, R, N, Q, F, W, Y, P, or C; A27 replaced with D, E, H, K, R, N, Q, F, W, Y, P, or C; S28 replaced with D, B, H, K, R, N, Q, F, W, Y, P, or C; N29 replaced with D, E, H, K, R, A, G, I, L, S, T, M, V, F, W, Y, P, or C; F30 replaced with D, E, H, K, R, N, Q, A, G, I, L, S, T, M, V, P, or C; D31 replaced with H, K, R, A, G, I, L, S, T, M, V, N, Q, F, W, Y, P, or C; C32 replaced with D, E, H, K, R, A, G, I, L, S, T, M, V, N, Q, F, W, Y, or P; C33 replaced with D, E, H, K, R, A, G, I, L, S, T, M, V, N, Q, F, W, Y, or P; L34 replaced with D, E, H, K, R, N, Q, F, W, Y, P, or C; G35 replaced with D, E, H, K, R, N, Q, F, W, Y, P, or C; Y36 replaced with D, E, H, K, R, N, Q, A, G, I, L, S, T, M, V, P, or C; T37 replaced with D, E, H, K, R, N, Q, F, W, Y, P, or C; D38 replaced with H, K, R, A, G, I, L, S, T, M, V, N, Q, F, W, Y, P, or C; R39 replaced with D, E, A, G, I, L, S, T, M, V, N, Q, F, W, Y, P, or C; I40 replaced with D, E, H, K, R, N, Q, F, W, Y, P, or C; L41 replaced with D, E, H, K, R, N, Q, F, W, Y, P, or C; H42 replaced with D, E, A, G, I, L, S, T, M, V, N, Q, F, W, Y, P, or C; P43 replaced with D, E, H, K, R, A, G, I, L, S, T, M, V, N, Q, F, W, Y, or C; K44 replaced with D, E, A, G, I, L, S, T, M, V, N, Q, F, W, Y, P, or C; F45 replaced with D, E, H, K, R, N, Q, A, G, I, L, S, T, M, V, P, or C; I46 replaced with D, E, H, K, R, N, Q, F, W, Y, P, or C; V47 replaced with D, E, H, K, R, N, Q, F, W, Y, P, or C; G48 replaced with D, E, H, K, R, N, Q, F, W, Y, P, or C; F49 replaced with D, E, H, K, R, N, Q, A, G, I, L, S, T, M, V, P, or C; T50 replaced with D, E, H, K, R, N, Q, F, W, Y, P, or C; R51 replaced with D, E, A, G, I, L, S, T, M, V, N, Q, F, W, Y, P, or C; Q52 replaced with D, E, H, K, R, A, G, I, L, S, T, M, V, F, W, Y, P, or C; L53 replaced with D, E, H, K, R, N, Q, F, W, Y, P, or C; A54 replaced with D, E, H, K, R, N, Q, F, W, Y, P, or C; N55 replaced with D, E, H, K, R, A, G, I, L, S, T, M, V, F, W, Y, P, or C; E56 replaced with H, K, R, A, G, I, L, S, T, M, V, N, Q, F, W, Y, P, or C; G57 replaced with D, E, H, K, R, N, Q, F, W, Y, P, or C; C58 replaced with D, E, H, K, R, A, G, I, L, S, T, M, V, N, Q, F, W, Y, or P; D59 replaced with H, K, X, A, G, I, L, S, T, M, V, N, Q, F, W, Y, P, or C; I60 replaced with D, E, H, K, R, N, Q, F, W, Y, P, or C; N61 replaced with D, E, H, K, R, A, G, I, L, S, T, M, V, F, W, Y, P, or C; A62 replaced with D, E, H, K, R, N, Q, F, W, Y, P, or C; I63 replaced with D, E, H, K, R, N, Q, F, W, Y, P, or C; I64 replaced with D, E, H, K, R, N, Q, F, W, Y, P, or C; F65 replaced with D, E, H, K, R, N, Q, A, G, I, L, S, T, M, V, P, or C; H66 replaced with D, E, A, G, I, L, S, T, M, V, N, Q, F, W, Y, P, or C; T67 replaced with D, E, H, K, R, N, Q, F, W, Y, P, or C; K68 replaced with D, E, A, G, I, L, S, T, M, V, N, Q, F, W, Y, P, or C; K69 replaced with D, E, A, G, I, L, S, T, M, V, N, Q, F, W, Y, P, or C; K70 replaced with D, E, A, G, I, L, S, T, M, V, N, Q, F, W, Y, P, or C; L71 replaced with D, E, H, K, R, N, Q, F, W, Y, P, or C; S72 replaced with D, E, H, K, R, N, Q, F, W, Y, P, or C; V73 replaced with D, E, H, K, R, N, Q, F, W, Y, P, or C; C74 replaced with D, E, H, K, R, A, G, I, L, S, T, M, V, N, Q, F, W, Y, or P; A75 replaced with D, E, H, K, R, N, Q, F, W, Y, P, or C; N76 replaced with D, E, H, K, R, A, G, I, L, S, T, M, V, F, W, Y, P, or C; P77 replaced with D, E, H, K, R, A, G, I, L, S, T, M, V, N, Q, F, W, Y, or C; K78 replaced with D, E, A, G, I, L, S, T, M, V, N, Q, F, W, Y, P, or C; Q79 replaced with D, E, H, K, R, A, G, I, L, S, T, M, V, F, W, Y, P, or C; T80 replaced with D, E, H, K, R, N, Q, F, W, Y, P, or C; W81 replaced with D, E, H, K, R, N, Q, A, G, I, L, S, T, M, V, P, or C; V82 replaced with D, E, H, K, R, N, Q, F, W, Y, P, or C; K83 replaced with D, E, A, G, I, L, S, T, M, V, N, Q, F, W, Y, P, or C; Y84 replaced with D, E, H, K, R, N, Q, A, G, I, L, S, T, M, V, P, or C; I85 replaced with D, E, H, K, R, N, Q, F, W, Y, P, or C; V86 replaced with D, E, H, K, R, N, Q, F, W, Y, P, or C; R87 replaced with D, E, A, G, I, L, S, T, M, V, N, Q, F, W, Y, P, or C; L88 replaced with D, E, H, K, R, N, Q, F, W, Y, P, or C; L89 replaced with D, E, H, K, R, N, Q, F, W, Y, P, or C; S90 replaced with D, E, H, K, R, N, Q, F, W, Y, P, or C; K91 replaced with D, E, A, G, I, L, S, T, M, V, N, Q, F, W, Y, P, or C; K92 replaced with D, E, A, G, I, L, S, T, M, V, N, Q, F, W, Y, P, or C; V93 replaced with D, E, H, K, R, N, Q, F, W, Y, P, or C; K94 replaced with D, E, A, G, I, L, S, T, M, V, N, Q, F, W, Y, P, or C; N95 replaced with D, E, H, K, R, A, G, I, L, S, T, M, V, F, W, Y, P, or C; M96 replaced with D, E, H, K, R, N, Q, F, W, Y, P, or C of SEQ ID NO:2.

Amino acids in the CK-B4 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vivo proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of CK-B4 that are essential for CK-B4 function. In other preferred embodiments, antibodies of the present invention bind regions of CK-B4 that are essential for CK-B4 function and inhibit or abolish CK-B4 function. In other preferred embodiments, antibodies of the present invention bind regions of CK-B4 that are essential for CK-B4 function and enhance CK-B4 function.

Additionally, protein engineering may be employed to improve or alter the characteristics of CK-B4 polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified CK-B4 polypeptides.

Non-naturally occurring variants of CK-B4 may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses antibodies that bind CK-B4 derivatives and analogs that have one or more amino acid residues deleted, added, and/or substituted to generate CK-B4 polypeptides that have better binding activity, better therapeutic activity, are expressed better, or are better suited to scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the CK-B4 polypeptides and/or an amino acid deletion at the second position of any one or more such recognition sequences will prevent glycosylation of the CK-B4 at the modified tripeptide sequence (see, e.g., Miyajimo et al., EMBO J 5(6):1193-1197). Additionally, one or more of the amino acid residues of CK-B4 polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of the polypeptide encoded by the deposited cDNAs (the deposit having ATCC Accession Number 75848); a polypeptide comprising, or alternatively, consisting of the polypeptide of SEQ ID NO:2 minus the amino terminal methionine; as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clones (the deposit having ATCC Accession Number 75848), the polypeptide of SEQ ID NO:2, and portions of such polypeptides with at least 30 amino acids and more preferably at least 50 amino acids.

By a polypeptide having an amino acid sequence at least, for example, 95% "identical" to a reference amino acid sequence of a CK-B4 polypeptide is intended that the amino acid sequence of the polypeptide is identical to the reference sequence except that the polypeptide sequence may include up to one amino acid alterations per each 20 amino acids of the reference amino acid of the CK-B4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the CK-B4 polypeptide sequence set forth herein as $n^1$-$m^1$, and/or $n^1$-$m^2$. In preferred embodiments, the application encompasses antibodies that bind proteins containing polypeptides at least 90%, 95%, 96%, 97%, 98% or 99% identical to polypeptides having the amino acid sequence of the specific CK-B4 N- and C-terminal deletions recited herein.

In certain preferred embodiments, antibodies of the invention bind CK-B4 fusion proteins as described above wherein the CK-B4 portion of the fusion protein are those described as $n^1$-$m^1$, and/or $n^1$-$m^2$ herein.

Antibodies of the Invention May Bind Modified CK-B4 Polypeptides

It is specifically contemplated that antibodies of the present invention may bind modified forms of CK-B4 protein.

In specific embodiments, antibodies of the present invention bind CK-B4 polypeptides (such as those described above) including, but not limited to naturally purified CK-B4 polypeptides, CK-B4 polypeptides produced by chemical synthetic procedures, and CK-B4 polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, CK-B4 polypeptides may also include an initial modified methionine residue, in some cases as a result of host-mediated processes.

In addition, CK-B4 proteins that antibodies of the present invention may bind can be chemically synthesized using techniques known in the art (e.g., see Creighton, Proteins: Structures and Molecular Principles, W.H. Freeman & Co., N.Y. (1983), and Hunkapiller, et al., *Nature* 310:105-111 (1984)). For example, a peptide corresponding to a fragment of a CK-B4 polypeptide can be synthesized by use of a peptide synthesizer. Furthermore, if desired, nonclassical amino acids or chemical amino acid analogs can be introduced as a substitution or addition into the CK-B4 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrlline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Nα-methyl amino acids, and amino acid analogs in general. Furthermore, the amino acid can be D (dextrorotary) or L (levorotary).

The invention additionally, encompasses antibodies that bind CK-B4 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$ acetylation, formylation, oxidation, reduction, metabolic synthesis in the presence of tunicamycin; etc.

Additional post-translational modifications to CK-B4 polypeptides include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of CK-B4 polypeptide which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride (ClSO$_2$CH$_2$CF$_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each CK-B4 polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the antibodies of the present invention may bind CK-B4 polypeptides that are modified by either natural processes, such as posttranslational processing, or by chemical modification techniques which are well known in the art. It will be appreciated that the same type of modification may be present in the same or varying degrees at several sites in a given CK-B4 polypeptide. CK-B4 polypeptides may be branched, for example, as a result of ubiquitination, and they may be cyclic, with or without branching. Cyclic, branched, and branched cyclic CK-B4 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Antibodies that Specifically Bind CK-B4

In one embodiment, the invention provides antibodies (e.g., anti-CK-B4 antibodies comprising two heavy chains and two light chains linked together by disulfide bridges) that specifically bind a CK-B4 polypeptide (e.g., SEQ ID NO: 2) or fragments or variants thereof, wherein the amino acid sequence of the heavy chain and the amino acid sequence of the light chain are the same as the amino acid sequence of a heavy chain and a light chain of an antibody expressed by one or more cell lines referred to in Table 1. In another embodiment, the invention provides antibodies (each consisting of two heavy chains and two light chains linked together by disulfide bridges to form an antibody) that specifically bind a CK-B4 polypeptide (e.g., SEQ ID NO: 2) or fragments or variants thereof, wherein the amino acid sequence of the heavy chain or the amino acid sequence of the light chain are the same as the amino acid sequence of a heavy chain or a light chain of an antibody expressed by one or more cell lines referred to in Table 1. Specific binding to CK-B4 polypeptides may be determined by immunoassays known in the art or described herein for assaying specific antibody-antigen binding. Molecules comprising, or alternatively consisting of, fragments or variants of these antibodies that specifically bind to CK-B4 are also encompassed by the invention, as are nucleic acid molecules encoding these antibodies molecules, fragments and/or variants (e.g., SEQ ID NOs:3-19).

In one embodiment of the present invention, antibodies that specifically bind to CK-B4 or a fragment or variant thereof, comprise a polypeptide having the amino acid sequence of a heavy chain of an antibody expressed by at least one of the cell lines referred to in Table 1 and/or a light chain of an antibody expressed by at least one of the cell lines referred to in Table 1.

In another embodiment of the present invention, antibodies that specifically bind to CK-B4 or a fragment or variant thereof, comprise a polypeptide having the amino acid sequence of any one of the VH domains of at least one of the scFvs referred to in Table 1 and/or any one of the VL domains of at least one of the scFvs referred to in Table 1. In preferred embodiments, antibodies of the present invention comprise the amino acid sequence of a VH domain and VL domain of the scFvs referred to in Table 1. Molecules comprising, or alternatively consisting of, antibody fragments or variants of the VH and/or VL domains of at least one of the scFvs referred to in Table 1 that specifically bind to CK-B4 are also encompassed by the invention, as are nucleic acid molecules encoding these VH and VL domains, molecules, fragments and/or variants.

The present invention also provides antibodies that specifically bind to a polypeptide, or polypeptide fragment or variant of CK-B4, wherein said antibodies comprise, or alternatively consist of, a polypeptide having an amino acid sequence of any one, two, three, or more of the VH CDRs contained in a VH domain of one or more scFvs referred to in Table 1. In particular, the invention provides antibodies that specifically bind CK-B4, comprising, or alternatively consisting of, a polypeptide having the amino acid sequence of a VH CDR1 contained in a VH domain of one or more scFvs referred to in Table 1. In another embodiment, antibodies that specifically bind CK-B4, comprise, or alternatively consist of, a polypeptide having the amino acid sequence of a VH CDR2 contained in a VH domain of one or more scFvs referred to in Table 1. In a preferred embodiment, antibodies that specifically bind CK-B4, comprise, or alternatively consist of a polypeptide having the amino acid sequence of a VH CDR3 contained in a VH domain of one or more scFvs referred to in Table 1. Molecules comprising, or alternatively consisting of, these antibodies, or antibody fragments or variants thereof, that specifically bind to CK-B4 or a CK-B4 fragment or variant thereof are also encompassed by the invention, as are nucleic acid molecules encoding these antibodies, molecules, fragments and/or variants (e.g., SEQ ID NOs:3-19).

The present invention also provides antibodies that specifically bind to a polypeptide, or polypeptide fragment or variant of CK-B4, wherein said antibodies comprise, or alternatively consist of, a polypeptide having an amino acid sequence of any one, two, three, or more of the VL CDRs contained in a VL domain of one or more scFvs referred to in Table 1. In particular, the invention provides antibodies that specifically bind CK-B4, comprising, or alternatively consisting of, a polypeptide having the amino acid sequence of a VL CDR1 contained in a VL domain of one or more scFvs referred to in Table 1. In another embodiment, antibodies that specifically bind CK-B4, comprise, or alternatively consist of, a polypeptide having the amino acid sequence of a VL CDR2 contained in a VL domain of one or more scFvs referred to in Table 1. In a preferred embodiment, antibodies that specifically bind CK-B4, comprise, or alternatively consist of a polypeptide having the amino acid sequence of a VL CDR3 contained in a VL domain of one or more scFvs referred to in Table 1. Molecules comprising, or alternatively consisting of, these antibodies, or antibody fragments or variants thereof, that specifically bind to CK-B4 or a CK-B4 fragment or variant thereof are also encompassed by the invention, as are nucleic acid molecules encoding these antibodies, molecules, fragments and/or variants (e.g., SEQ ID NOs:3-19).

The present invention also provides antibodies (including molecules comprising, or alternatively consisting of, antibody fragments or variants) that specifically bind to a CK-B4 polypeptide or polypeptide fragment or variant of CK-B4, wherein said antibodies comprise, or alternatively consist of, one, two, three, or more VH CDRs and one, two, three or more VL CDRs, as contained in a VH domain or VL domain of one or more scFvs referred to in Table 1. In particular, the invention provides for antibodies that specifically bind to a polypeptide or polypeptide fragment or variant of CK-B4, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1. In a preferred embodiment, one or more of these combinations are from the same scFv as disclosed in Table 1. Molecules comprising, or alternatively consisting of, fragments or variants of these antibodies, that specifically bind to CK-B4 are also encompassed by the invention, as are nucleic acid molecules encoding these antibodies, molecules, fragments or variants (e.g., SEQ ID NOs:3-19).

Nucleic Acid Molecules Encoding Anti-CK-B4 Antibodies

The present invention also provides for nucleic acid molecules, generally isolated, encoding an antibody of the invention (including molecules comprising, or alternatively consisting of, antibody fragments or variants thereof). In specific embodiments, the nucleic acid molecules encoding an antibody of the invention comprise, or alternatively consist of SEQ ID NOs:3-19 or fragments or variants thereof.

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 and a VL domain having an amino acid sequence of VL domain of at least one of the scFvs referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or a VL domain having an amino acid sequence of a VL domain of at least one of the scFvs referred to in Table 1.

The present invention also provides antibodies that comprise, or alternatively consist of, variants (including derivatives) of the antibody molecules (e.g., the VH domains and/or VL domains) described herein, which antibodies specifically bind to CK-B4 or fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid subsitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a CK-B4 receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g, improvements in antigen binding activity or change in antibody specificity). Following mutagenesis, the encoded protein may routinely be expressed and the functional and/or biological activity of the encoded protein, (e.g., ability to specifically bind CK-B4) can be determined using techniques described herein or by routinely modifying techniques known in the art.

In a specific embodiment, an antibody of the invention (including a molecule comprising, or alternatively consisting of, an antibody fragment or variant thereof), that specifically binds CK-B4 polypeptides or fragments or variants thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1. under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to a CK-B4 polypeptide or fragments or variants of a CK-B4 polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1.

In another embodiment, an antibody (including a molecule comprising, or alternatively consisting of, an antibody fragment or variant thereof), that specifically binds to a CK-B4 polypeptide or fragments or variants of a CK-B4 polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1.

Methods of Producing Antibodies

Antibodies in accordance with the invention are preferably prepared utilizing a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a CK-B4 polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184: 177-186 (1995); Kettleborough et al., Eur. J. Immunol. 24:952-958 (1994); Persic et al., Gene 187 9-18 (1997); Burton et al., Advances in Immunology 57:191-280(1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single schain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind CK-B4 polypeptides with preferred binding characteristics such as improved affinity or improved off rates. Additionally, VH and VL segments—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind CK-B4 polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including, but not limited to, myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 2), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH or VL domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g. as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al, BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g. a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed, Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of one or more scFvs referred to in Table 1, or fragments or variants thereof, are inserted within antibody framework regions using recombinant DNA techniques known in the art. In a specific embodiment, one, two, three, four, five, six, or more of the CDRs of VH and/or VL domains of one or more scFvs referred to in Table 1, or fragments or variants thereof, is inserted within antibody framework regions using recombinant DNA techniques known in the art. The antibody framework regions may be naturally occurring or consensus antibody framework regions, and preferably human antibody framework regions (see, e.g., Chothia et al., J. Mol. Biol. 278: 457-479 (1998) for a listing of human antibody framework regions, the contents of which are hereby incorporated by reference in its entirety). Preferably, the polynucleotides generated by the combination of the antibody framework regions and CDRs encode an antibody (including molecules comprising, or alternatively consisting of, antibody fragments or variants thereof) that specifically binds to CK-B4. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

Xenomouse™ Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germine configuration YAC fragments of the human heavy chain loci and kappa light chain loci, respectively, to produce XenoMouse™ mice. See Mendez et al. *Nature Genetics* 15:146-156 (1997), Green and Jakobovits *J Exp. Med.* 188:483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/710,515, filed Nov. 8, 1990, Ser. No. 07/919, 297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/471,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al. *Nature Genetics* 15:146-156 (1997) and Green and Jakobovits *J Exp. Med.* 188:483 495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against CK-B4 polypeptides in order to vitiate concerns and/or effects of HAMA or HACA responses.

Monoclonal antibodies specific for CK-B4 polypeptides may be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XenoMouse™ mice may be immunized with CK-B4 polypeptides. After immunization, the splenocytes of such mice may be extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the CK-B4 polypetides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, WO98/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1, or fragments or variants thereof, and framework regions (and, optionally one or more CDRs not present in the scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s of a VH or VL domain of one or more of the scFvs referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is (are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants teherof (single chain antibodies), microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g. the adenovirus late promoter, the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entirities by refernce herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovims transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O3O and HsS78Bst.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloningl , Vol.* 3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availabilty of cell lines (e.g., the murine myeloma cell line, NS0) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169 (1992) and in Biblia and Robinson *Biotechnol. Prog.* 11:1 (1995) which are incorporated in their entirities by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, 213Bi, or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin.

In specific embodiments, antibodies of the invention may be labeled with Europium. For example, antibodies of the invention may be labelled with Europium using the DELFIA Eu-labeling kit (catalog# 1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N'',N'''-tetraacetic acid (DOTA). In specific embodiments, the macrocyclic chelator is □-(5-isothiocyanato-2-methoxyphenyl)-1,4,7,10-tetraazacyclododecane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (ClSO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-CK-B4 Antibodies

Antibodies of the present invention (including molecules comprising, or alternatively consisting of, antibody fragments or variants thereof) may also be described or specified in terms of their binding to CK-B4 polypeptides or fragments or variants of CK-B4 polypeptides. In specific embodiments, antibodies of the invention bind CK-B4 polypeptides, or fragments or variants thereof, with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind CK-B4 polypeptides or fragments or variants thereof with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, antibodies of the invention bind CK-B4 polypeptides or fragments or variants thereof with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. The invention encompasses antibodies that bind CK-B4 polypeptides with a dissociation constant or $K_D$ that is within any one of the ranges that are between each of the individual recited values.

In specific embodiments, antibodies of the invention bind CK-B4 polypeptides or fragments or variants thereof with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, antibodies of the invention bind CK-B4 polypeptides or fragments or variants thereof with an off rate ($k_{off}$) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$. The invention encompasses antibodies that bind CK-B4 polypeptides with an off rate ($k_{off}$) that is within any one of the ranges that are between each of the individual recited values.

In other embodiments, antibodies of the invention bind CK-B4 polypeptides or fragments or variants thereof with an on rate ($k_{on}$) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. More preferably, antibodies of the invention bind CK-B4 polypeptides or fragments or variants thereof with an on rate ($k_{on}$) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$. The invention encompasses antibodies that bind CK-B4 polypeptides with on rate ($k_{on}$) that is within any one of the ranges that are between each of the individual recited values.

The antibodies of the invention (including molecules comprising, or alternatively consisting of, antibody fragments or variants thereof) specifically bind to a polypeptide or polypeptide fragment or variant of human CK-B4 (e.g., SEQ ID NO:2). In another embodiment, the antibodies of the invention specifically bind to a polypeptide or polypeptide fragment or variant of simian CK-B4 polypeptides. In yet another embodiment, the antibodies of the invention specifically bind to a polypeptide or polypeptide fragment or variant of murine CK-B4 polypeptides. In one embodiment, the antibodies of the invention bind specifically to human and simian CK-B4 polypeptides. In another embodiment, the antibodies of the invention bind specifically to human CK-B4 polypeptides and murine CK-B4 polypeptides. More preferably, antibodies of the invention, preferentially bind to human CK-B4 polypeptides compared to murine CK-B4 polypeptides.

In preferred embodiments, the antibodies of the present invention (including molecules comprising, or alternatively consisting of, antibody fragments or variants thereof), specifically bind to CK-B4 polypeptides and do not cross-react with any other antigens. In preferred embodiments, the antibodies of the invention specifically bind to CK-B4 polypeptides (e.g., SEQ ID NO:2 or fragments or variants thereof) and do not cross-react with one or more additional members of the Chemokine Family (e.g., RANTES, MIP-1α, MIP-1β, MIP-1γ, MCP-1, MCP-2, MCP-3, MCP-4, I-309, Eotaxin, TECK, Dctactin, Dendrokine, HCC-1, MIP-3β, Lymphotactin, Fractalkine, IL-8, MGSA, PF4, SDF-1, NAP-2, IP-10, and ENA78).

In another embodiment, the antibodies of the present invention (including molecules comprising, or alternatively consisting of, antibody fragments or variants thereof), specifically bind to CK-B4 polypeptides and cross-react with other antigens. In other embodiments, the antibodies of the invention specifically bind to CK-B4 polypeptides (e.g., SEQ ID NO:2, or fragments or variants thereof) and cross-react with one or more additional members of the Chemokine Family (e.g., RANTES, MIP-1α, MIP-1β, MIP-1γ, MCP-1, MCP-2, MCP-3, MCP-4, I-309, Eotaxin, TECK, Dctactin, Dendrokine, HCC-1, MIP-3β, Lymphotactin, Fractalkine, IL-8, MGSA, PF4, SDF-1, NAP-2, IP-10, and ENA78).

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to CK-B4 polypeptides, the ability to inhibit CK-B4 mediated biological activity (e.g., the ability to inhibit chemotaxis of T cells, see Examples 3 and 4, or the ability to inhibit proliferation of CK-B4 receptor expressing cells); or the ability to substantially block binding of CK-B4, or a fragment, variant or fusion protein thereof, to its receptor (e.g., CCR6; GenBank ID: U68030, see, Example 5). Other biological activities that antibodies against CK-B4 polypeptides may have, include, but are not limited to, the ability to stimulate CK-B4 mediated biological activity (e.g., to stimulate chemotaxis of CK-B4 receptor expressing cells (e.g., T cells, dendritic cells, B cells)) or the ability to stimulate proliferation of CK-B4 receptor expressing cells. Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that inhibit one or more CK-B4 polypeptide mediated biological activities. In one embodiment, an antibody that inhibits one or more CK-B4 polypeptide mediated biological activities comprises, or alternatively consists of a VH and/or a VL domain of at least one of the scFvs referred to in Table 1, or fragment or variant thereof. In a specific embodiment, an antibody that inhibits one or more CK-B4 polypeptide mediated biological activities comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that inhibit proliferation of CK-B4 expressing cells. In one embodiment, an antibody that inhibits proliferation of CK-B4 expressing cells comprises, or alternatively consists of a VH and/or a VL domain of at least one of the scFvs referred to in Table 1, or fragment or variant thereof. In a specific embodiment, an antibody that inhibits proliferation of CK-B4 expressing cells comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that inhibit chemotaxis of CK-B4 expressing cells (e.g., T cells; See Example 4 and 5). In one embodiment, an antibody that inhibits chemotaxis of CK-B4 expressing cells comprises, or alternatively consists of a VH and/or a VL domain of at least one of the scFvs referred to in Table 1, or fragment or variant thereof. In a specific embodiment, an antibody that inhibits chemotaxis of CK-B4 expressing cells comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the binding of CK-B4 ligand to a CK-B4 receptor. In one embodiment, an antibody that blocks or inhibits the binding of CK-B4 ligand to a CK-B4 receptor comprises, or alternatively consists of a VH and/or a VL domain of at least one of the scFvs referred to in Table 1, or fragment or variant thereof. In a specific embodiment, an antibody that blocks or inhibits the binding of CK-B4 ligand to a CK-B4 receptor comprises, or alternatively consists of a VH and a VL domain of any one of the scFvs referred to in Table 1, or fragment or variant thereof. In a specific embodiment, the CK-B4 receptor is CCR6. Nucleic acid molecules encoding these antibodies are also encompassed by the invention.

The present invention also provides for antibodies (including molecules comprising, or alternatively consisting of, antibody fragments or variants thereof), that stimulate proliferation and/or chemotaxis of CK-B4 expressing cells (e.g., T cells). In one embodiment, an antibody that stimulates proliferation and/or chemotaxis of CK-B4 expressing cells comprises, or alternatively consists of a VH and/or a VL domain of at least one of the scFvs referred to in Table 1, or fragment or variant thereof. In a specific embodiment, an antibody that stimulates proliferation and/or chemotaxis of CK-B4 expressing cells comprises, or alternatively consists of a VH and a VL domain of any one of the scFvs referred to in Table 1, or fragment or variant thereof. Nucleic acid molecules encoding these antibodies are also encompassed by the invention.

Antibodies of the present invention (including antibody fragments or variants thereof) may be characterized in a variety of ways. In particular, antibodies and related molecules of the invention may be assayed for the ability to specifically bind to CK-B4 polypeptides or a fragment or variant of CK-B4 polypeptides using techniques described herein or routinely modifying techniques known in the art. Assays for the ability of the antibodies of the invention to specifically bind CK-B4 polypeptides or a fragment of CK-B4 polypeptides may be performed in solution (e.g., Houghten, Bio/Techniques 13:412-421 (1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403, 484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Antibodies that have been identified to specifically bind to CK-B4 polypeptides or a fragment or variant of CK-B4 polypeptides can then be assayed for their specificity and affinity for CK-B4 polypeptides or a fragment or variant of a CK-B4 polypeptide using or routinely modifying techniques described herein or otherwise known in the art.

The antibodies of the invention may be assayed for specific binding to CK-B4 polypeptides and cross-reactivity with other antigens by any method known in the art. Immunoassays which can be used to analyze specific binding and cross-reactivity include, but are not limited to, competitive and non-competitive assay systems using techniques such as BIAcore analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen in the form of a CK-B4-Fc fusion protein, may be bound to the anti-Ig Fc coated to the plate. This may be desirable so as to maintain the antigen protein (e.g., the CK-B4 polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I, or fragment or variant thereof with the antibody of interest in the presence of increasing amounts of unlabeled antigen, and the detection of the antibody bound to the labeled antigen. The affinity of the antibody of the present invention for CK-B4 and the binding off-rates can be determined from the data by Scatchard plot analysis. Competition with a second antibody can also be determined using radioimmunoassays. In this case, CK-B4 polypeptide is incubated with an antibody of the present invention conjugated to a labeled compound (e.g., compound labeled with $^3$H or $^{125}$I in the presence of increasing amounts of an unlabeled second anti-CK-B4 antibody. This kind of competitive assay between two antibodies, may also be used to determine if two antibodies bind the same, closely associated (e.g., overlapping) or different epitopes.

In a preferred embodiment, BIAcore kinetic analysis is used to determine the binding on and off rates of antibodies (including antibody fragments or variants thereof) to CK-B4, or fragments of CK-B4. BIAcore kinetic analysis comprises analyzing the binding and dissociation of antibodies from chips with immobilized CK-B4 on their surface.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g. $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146: 2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357-11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to CK-B4 may be recombined with one or more components, motifs, sections, parts, domains, fragments, etc. of one or more heterologous molecules.

Moreover, the antibodies of the present invention (including antibody fragments or variants thereof), can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not lmited to, luciferase, luciferin, and aequorin; and examples of suitable radioactive material include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody of the invention (including an scFv or other molecule comprising, or alternatively consisting of, antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and frragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), Fas Ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of CK-B4 polypeptides in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types, such as T-cells (e.g., activated T-cells). In other embodiments, the antibodies of the invention may be useful as tumors and/or cancer cell markers. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as might be found with hematological malignancies (i.e. minimal residual disease MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Epitope Mapping

The present invention provides antibodies (including antibody fragments or variants thereof), that can be used to identify epitopes of a CK-B4 polypeptide. In particular, the antibodies of the present invention can be used to identify epitopes of a human CK-B4 polypeptide (e.g., SEQ ID NO:2); a murine CK-B4; a rat CK-B4 polypeptide; or a monkey CK-B4 polypeptide, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occuring forms of CK-B4 polypeptides.

Diagnostic Uses of Antibodies

Labeled antibodies of the invention (including molecules comprising, or alternatively consisting of, antibody fragments or variants thereof) which specifically bind to a CK-B4 polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) which specifically bind to a CK-B4 polypeptide can be used for diagnostic purposes to detect, diagnose, prognose, or monitor diseases and/or disorders associated with the aberrant expression and/or activity of a CK-B4 polypeptide.

The invention provides for the detection of expression of a CK-B4 polypeptide comprising: (a) assaying the expression of a CK-B4 polypeptide in a biological sample from an individual using one or more antibodies of the invention that specifically binds to a CK-B4 polypeptide; and (b) comparing the level of a CK-B4 polypeptide with a standard level of a CK-B4 polypeptide, (e.g., the level in normal biological samples).

The invention provides for the detection of aberrant expression of a CK-B4 polypeptide comprising: (a) assaying the expression of a CK-B4 polypeptide in a biological sample from an individual using one or more antibodies of the invention that specifically binds to a CK-B4 polypeptide; and (b) comparing the level of a CK-B4 polypeptide with a standard level of a CK-B4 polypeptide, e.g., in normal biological samples, whereby an increase or decrease in the assayed level of a CK-B4 polypeptide compared to the standard level of a CK-B4 polypeptide is indicative of aberrant expression.

By "biological sample" is intended any fluids and/or cells obtained from an individual, body fluid, body tissue, body cell, cell line, tissue culture, or other source which may contain a CK-B4 polypeptide protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with aberrant expression of a CK-B4 polypeptide or a CK-B4 polypeptide receptor (e.g., CCR6) in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that specifically binds to a CK-B4 polypeptide; b) waiting for a time interval following the administering for permitting the labeled antibody to preferentially concentrate at sites in the subject where CK-B4 polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of a CK-B4 polypeptide or a CK-B4 polypeptide receptor. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Imnunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In specific embodiments, antibodies of the present invention may be used in wound healing and in the diagnosis, prevention, and treatment of proliferative disorders, as well as immune system diseases and disorders including autoimmune disease, inflammatory disorders, immunodeficiencies, infections, HIV, arthritis, allergy, psoriasis, dermatitis, and inflammatory bowel disease, particularly those diseases and/or disorders described in the "Therapeutic Uses of Antibodies" sections below.

Therapeutic Uses of Antibodies

One or more antibodies of the present invention (including molecules comprising, or alternatively consisting of, antibody fragments or variants thereof) that specifically bind to CK-B4 may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein.

Therapeutic Uses of Antibodies for Treating Inflammatory Disorders and Wound Healing In highly preferred embodiments, antibodies and antibody compositions of the invention may be useful for treating, diagnosing, preventing, and/or detecting inflammatory diseases. In a specific embodiment, antibodies and antibody compositions of the invention are useful in the diagnosis, treatment, detection, and/or prevention of psoriasis, dermatitis, Langerhans cell histiocytosis, allergy, asthma, and inflammatory bowel disease.

In other highly preferred embodiments, antibodies and antibody compositions of the invention are useful in the diagnosis and treatment or prevention of immune diseases and disorders including, but not limited to, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can affect virtually any tissue of the body. Accordingly, antibodies of the invention have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In highly preferred embodiments, antibodies and antibody compositions of the invention are useful to diagnose, prognose, prevent, and/or treat organ transplant rejections and graft-versus-host disease. Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD. In specific embodiments, antibodies and antibody compositions of the invention that inhibit an immune response, particularly the activation, proliferation, differentiation, or chemotaxis of T-cells, may be an effective therapy in preventing allergic and hyperacute xenograft rejection.

In other preferred embodiments, antibodies of the present invention are useful to diagnose, prognose, prevent, and/or treat immune complex diseases, including, but not limited to, serum sickness, post streptococcal glomerulonephritis, polyarteritis nodosa, and immune complex-induced vasculitis.

Antibodies and antibody compositions of the invention are also useful in promoting angiogenesis and/or wound healing (e.g., wounds, burns, and bone fractures).

In a highly preferred embodiment, antibodies and antibody compositions of the invention may be used to stimulate epithelial cell proliferation and basal keratinocytes for the purpose of wound healing, and to stimulate hair follicle production and healing of dermal wounds. Antibodies and antibody compositions of the invention may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Antibodies and antibody compositions of the invention could be used to promote dermal reestablishment subsequent to dermal loss.

In another highly preferred embodiment, antibodies and antibody compositions of the invention may be used as an adjuvant to enhance immune responsiveness to specific antigen, such as in anti-viral immune responses.

More generally, antibodies and antibody compositions of the invention are useful in regulating (i.e., elevating or reducing) immune response. For example, antibodies and antibody compositions of the invention may be useful in preparation or recovery from surgery, trauma, radiation therapy, chemotherapy, and transplantation, or may be used to boost immune response and/or recovery in the elderly and immunocompromised individuals. Alternatively, antibodies and antibody compositions of the invention are useful as immunosuppressive agents, for example in the treatment or prevention of autoimmune disorders. In specific embodiments, antibodies and antibody compositions of the invention are used to treat or prevent chronic inflammatory, allergic or autoimmune conditions, such as those described herein or are otherwise known in the art.

Therapeutic Uses of Antibodies for Treating Cancers

In highly preferred embodiments, antibodies of the invention that bind a CK-B4 polypeptide and inhibit proliferation of CK-B4 expressing cells are used to diagnose, treat, prevent or ameliorate cancer. In specific embodiments, antibodies of the invention are used to inhibit the progression or metastasis of myeloproliferative and other disorders such as leukemia, T-cell lymphoma, and/or B-cell lymphoma.

In other preferred embodiments, antibodies of the invention that bind a CK-B4 polypeptide and inhibit proliferation of CK-B4 expressing cells are used to diagnose, treat, prevent or ameliorate cancers and related disorders including, but not limited to, colon cancer, cervical cancer, leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In specific embodiments, antibodies of the invention used to treat the aforementioned cancers are administered with or conjugated to a cytotoxic and/or chemotherapeutic agent.

Therapeutic and Diagnostic Uses of Antibodies for Treating Autoimmune Disorders

In highly preferred embodiments, antibodies and antibody compositions of the invention are used to diagnose, treat, prevent or ameliorate autoimmune diseases, disorders, or conditions associated with such diseases or disorders. Autoimmune disorders and related disorders, include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, ulcerative colitis, dense deposit disease, rheumatic heart disease, glomerulonephritis (e.g., IgA nephropathy), pemphigus vulgaris, discoid lupus, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye, autoimmune thyroiditis, hypothyroidism (i.e., Hashimoto's thyroiditis), systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, graft v. host diseases (GVHD) and other inflammatory, granulamatous, degenerative, and atrophic disorders).

In a specific embodiment, antibodies of the invention can used to diagnose, treat, inhibit, prognose, diagnose or prevent rheumatoid arthritis.

In a specific embodiment, antibodies of the invention can used to diagnose, treat, inhibit, prognose, diagnose or prevent systemic lupus erythematosus.

In a specific embodiment, antibodies of the invention can used to diagnose, treat, inhibit, prognose, diagnose or prevent autoimmune encephalitis.

Additional Therapeutic Uses of Antibodies

In an additional highly preferred embodiment, the antibodies of the invention can be used to diagnose, treat, inhibit or prevent diseases, disorders or conditions associated with immunodeficiencies including, but not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, autoimmune neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

Antibodies and antibody compositions of the present invention may be useful in treating, preventing, prognosing, and/or diagnosing diseases, disorders, and/or conditions of hematopoietic cells including, but not limited to, leukopenia, neutropenia, anemia, and thrombocytopenia. Alternatively, antibodies of the invention could be used to decrease differentiation and proliferation of hematopoietic cells, including the pluripotent stem cells, in an effort to treat or prevent those diseases, disorders, and/or conditions associated with an increase in certain (or many) types of hematopoietic cells, including but not limited to, histiocytosis.

The antibodies of the invention can be used to diagnose, treat, ameliorate or prevent diseases, disorders or conditions associated with aberrant expression and/or activity of CK-B4, including, but not limited to, any one or more of the diseases, disorders, or conditions described herein. The treatment and/or prevention of diseases, disorders, or conditions associated with aberrant CK-B4 expression and/or activity includes, but is not limited to, alleviating symptoms associated with those diseases, disorders or conditions. Antibodies of the invention may be provided in pharmaceutically acceptable compositions as known in the art or as described herein.

Further, antibodies of the present invention (including molecules comprising, or alternatively consisting of, antibody fragments or variants thereof) which activate CK-B4-mediated biological activities (e.g., the chemotaxis of CK-B4 receptor expressing cells (e.g., T cells, dendritic cells, B cells)) can be administered to an animal to diagnose, treat, prevent or ameliorate a disease or disorder described herein, particularly inflammatory and other immune disorders. These antibodies may potentiate or activate either all or a subset of the biological activities of CK-B4, for example, by inducing a conformational change in CK-B4. In a specific embodiment, an antibody of the present invention that increases CK-B4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to CK-B4 activity in absence of the antibody is administered to an animal to diagnose, treat, prevent or ameliorate a disease or disorder. In another embodiment, a combination of antibodies, a combination of antibody fragments, a combination of antibody variants, or a combination of antibodies, antibody fragments and/or antibody variants that increase CK-B4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to CK-B4 activity in absence of the said antibodies or antibody fragments and/or antibody variants is administered to an animal to diagnose, treat, prevent or ameliorate a disease or disorder.

Further, antibodies of the present invention (including molecules comprising, or alternatively consisting of, antibody fragments or variants thereof) which activate CK-B4-mediated biological activities (e.g., the induction of chemotaxis and/or proliferation in CK-B4 receptor expressing cells) can be administered to an animal to diagnose, treat, prevent or ameliorate a disease or disorder associated with aberrant CK-B4 expression and/or function or aberrant CK-B4 receptor expression and/or function, especially cancer and other hyperproliferative disorders. These antibodies may potentiate or activate either all or a subset of the biological activities of CK-B4, for example, by inducing a conformational change in CK-B4. In a specific embodiment, an antibody of the present invention that increases CK-B4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to CK-B4 activity in absence of the antibody is administered to an animal to diagnose, treat, prevent or ameliorate a disease or disorder associated with aberrant CK-B4 expression and/or function or aberrant CK-B4 receptor expression and/or function. In another embodiment, a combination of antibodies, a combination of antibody fragments, a combination of antibody variants, or a combination of antibodies, antibody fragments and/or antibody variants that increase CK-B4 activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to CK-B4 activity in absence of the said antibodies or antibody fragments and/or antibody variants is administered to an animal to diagnose, treat, prevent or ameliorate a disease or disorder associated with aberrant CK-B4 expression and/or function or aberrant CK-B4 receptor expression and/or function.

Antibodies of the present invention (including molecules comprising, or alternatively consisting of, antibody fragments or variants thereof) that function as agonists or antagonists of a CK-B4, preferably of CK-B4 signal transduction, can be administered to an animal to diagnose, treat, prevent or ameliorate a disease or disorder associated with aberrant CK-B4 expression and/or function or aberrant CK-B4 receptor expression and/or function. For example, antibodies of the invention which mimic the action of CK-B4 binding to the CK-B4 receptor, in full or in part, (e.g., antibodies that act as CK-B4 agonists), may be administered to an animal to diagnose, treat, prevent or ameliorate a disease or disorder associated aberrant CK-B4 expression, function, or aberrant CK-B4 receptor expression or function. As an alternative example, antibodies of the invention which disrupt or prevent the interaction between CK-B4 and its receptor or inhibit, reduce, or prevent signal transduction through one or more CK-B4, may be administered to an animal to diagnose, treat, prevent or ameliorate a disease or disorder associated with aberrant CK-B4 expression and/or function or aberrant CK-B4 receptor expression and/or function. Antibodies of the invention which do not prevent CK-B4 from binding its ligand but inhibit or downregulate CK-B4 signal transduction can be administered to an animal to diagnose, treat, prevent or ameliorate a disease or disorder associated with aberrant CK-B4 expression, abberant CK-B4 function, aberrant CK-B4 receptor expression, or abberant CK-B4 receptor function. The ability of an antibody of the invention to enhance, inhibit, upregulate or downregulate CK-B4 signal transduction may be determined by techniques described herein or otherwise known in the art. For example, CK-B4-induced receptor activation and the activation of signaling molecules can be determined by detecting the association of adaptor proteins with the CK-B4 receptors, by immunoprecipitation followed by western blot analysis (for example, as described herein).

In a specific embodiment, an antibody of the present invention (including molecules comprising, or alternatively consisting of, antibody fragments or variants thereof) that inhibits or downregulates, in full or in part, CK-B4 activity (e.g., the chemotaxis of CK-B4 receptor expressing cells (e.g., T cells, dendritic cells, B cells)) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to CK-B4 activity in absence of the antibody is administered to an animal to diagnose, treat, prevent or ameliorate a disease or disorder associated with aberrant CK-B4 expression and/or function or aberrant CK-B4 receptor expression and/or function. In another embodiment, a combination of antibodies, a combination of antibody fragments, a combination of antibody variants, or a combination of antibodies, antibody fragments, and/or variants that inhibit or downregulate CK-B4 activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to CK-B4 activity in absence of said antibodies, antibody fragments, and/or antibody variants are administered to an animal to diagnose, treat, prevent or ameliorate a disease or disorder associated with aberrant CK-B4 expression and/or function or aberrant CK-B4 receptor expression and/or function.

In a specific embodiment, an antibody of the present invention (including molecules comprising, or alternatively consisting of, antibody fragments or variants thereof) that inhibits or downregulates, in full or in part, CK-B4 activity (e.g., stimulation of chemotaxis and/or proliferation of lymphocytes or dendritic cells) by at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to CK-B4 activity in absence of the antibody is administered to an animal to diagnose, treat, prevent or ameliorate a disease or disorder associated with aberrant CK-B4 expression and/or function or aberrant CK-B4 receptor expression and/or function. In another embodiment, a combination of antibodies, a combination of antibody fragments, a combination of antibody variants, or a combination of antibodies, antibody fragments, and/or variants that inhibit or downregulate CK-B4 activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to CK-B4 activity in absence of said antibodies, antibody fragments, and/or antibody variants are administered to an animal to diagnose, treat, prevent or ameliorate a disease or disorder associated with aberrant CK-B4 expression and/or function or aberrant CK-B4 receptor expression and/or function.

In another embodiment, therapeutic or pharmaceutical compositions of the invention are administered to an animal to diagnose, treat, prevent or ameliorate infectious diseases. Infectious diseases include diseases associated with yeast, fungal, viral and bacterial infections. Viruses associated with viral infections which can be treated or prevented in accordance with this invention include, but are not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenavirues (e.g., lassa fever virus), paramyxoviruses (e.g., morbillivirus virus, human respiratory syncytial virus, mumps, and pneumovirus), adenoviruses, bunyaviruses (e.g., hantavirus), cornavimses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C), papovaviruses (e.g., papillomavirues), picornaviruses (e.g., rhinoviruses, enteroviruses and hepatitis A viruses), poxviruses, reoviruses (e.g., rotavirues), togavirues (e.g., rubella virus), rhabdovirues (e.g., rabies virus). Microbial pathogens associated with bacterial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

Human immunodeficiency virus (HIV) targets chemokine receptors during entry into cells, and certain chemokines act as HIV suppressive factors (Garzino-Demo et al., *Proc. Natl. Acad. Sci U.S.A.* 96:11986-11991 (1999)). Thus, in additional preferred embodiments, antibodies and antibody compositions of the invention are used to treat AIDS and pathologies associated with AIDS. Another embodiment of the present invention encompasses the use of antibodies of the invention to reduce death of T cells in HIV-infected patients.

Suitable agents, which also block binding of CK-B4 to a CK-B4 receptor (e.g., CCR6) that may be administered with the antibodies of the present invention include, but are not limited to, soluble CK-B4 receptor polypeptides; multimeric forms of soluble CK-B4 receptor polypeptides; and CK-B4 antibodies that bind the CK-B4 without transducing the biological signal that results in chemotaxis, anti-CK-B4 antibodies that block binding of CK-B4 to one or more CK-B4 receptors, and muteins of CK-B4 that bind CK-B4 receptors but do not transduce the biological signal that results in chemotaxis.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228:190 (1985); During et al., Ann. Neurol. 25:35 1 (1989); Howard et al., J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that specifically bind to one or more CK-B4 polypeptides, or polynucleotides encoding antibodies that specifically bind to one or more CK-B4 polypeptides, for both immunoassays and therapy of disorders related to CK-B4 polynucleotides or polypeptides, including fragments thereof. Such antibodies will preferably have an affinity for CK-B4 polypeptides and/or CK-B4 polypeptide fragments. Preferred binding affinities include those with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind CK-B4 polypeptides or fragments or variants thereof with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, antibodies of the invention bind CK-B4 polypeptides or fragments or variants thereof with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In a preferred embodiment, antibodies of the invention inhibit proliferation and/or chemotaxis of CK-B4 receptor expressing cells. In an additional preferred embodiment, antibodies of the invention induce proliferation and/or chemotaxis of CK-B4 receptor expressing cells.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to chemotherapeutic agents, antibiotics, antivirals, anti-retroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Combination Therapies with Anti-CK-B4 Antibodies, Immunomodulatory Agents, Antiviral Drugs, and/or Chemotherapeutic Agents Anti-CK-B4 antibodies may be administered in combination with other anti-CK-B4 antibodies, CK-B4, and/or chemotherapeutics.

In specific embodiments, an antibody of the invention that specifically binds CK-B4 is used or administered in combination with a second antibody that specifically binds CK-B4. In another embodiment, the antibodies specific for CK-B4 are antagonistic antibodies that inhibit proliferation and/or chemotaxis of CK-B4 expressing cells (e.g., T cells). In a specific embodiment, the combination of anti-CK-B4 treatment inhibits more proliferation and/or chemotaxis of CK-B4 expressing cells than either anti-CK-B4 antibody treatment alone. The anti-CK-B4 antibodies can be administered either simultaneously, sequentially, or a combination of simultaneous or sequential administration throughout the dosage regimen. In another specific embodiment anti-CK-B4 antibodies are used or administered in combination with a chemotherapeutic drug, antiviral drug, and/or immunomodulatory drug. In a particular embodiment, the synergistic inhibition and/or stimulation of proliferation and/or chemotaxis resulting from anti-CK-B4 antibody treatment, is more evident or more pronounced when the anti-CK-B4 antibodies are used or administered in combination with a chemotherapeutic agent, antiviral drug, immunomodulatory drug, and/or a cross-linking reagent.

In another embodiment, the second antibody specific for CK-B4 is an agonistic antibody that stimulates proliferation, and/or chemotaxis of CK-B4 expressing cells. In a specific embodiment, the combination of anti-CK-B4 treatment stimulates more proliferation and/or chemotaxis of CK-B4 expressing cells than either anti-CK-B4 antibody treatment alone.

In additional embodiments, anti-CK-B4 antibodies of the present invention may be administered in combination with a soluble form of other chemolines which include, but are not limited to, RANTES, MIP-1α, MIP-1β, MIP-1γ, MCP-1, MCP-2, MCP-3, MCP-4, I-309, Eotaxin, TECK, Dctactin, Dendrokine, HCC-1, MIP-3β, Lymphotactin, Fractalkine, IL-8, MGSA, PF4, SDF-1, NAP-2, IP-10, and/or ENA78.

In a highly preferred embodiment, compositions of the invention are administered in combination with a chemotherapeutic agent. Chemotherapeutic agents that may be administered with the compositions of the invention include, but are not limited to, antibiotic derivatives (e.g., doxorubicin (adriamycin), bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguarine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, etoposide, Topotecan, 5-Fluorouracil, paclitaxel (Taxol), Cisplatin, Cytarabine, and IFN-gamma, irinotecan (Camptosar, CPT-11), and gemcitabine (GEMZAR™)).

In a highly preferred embodiment, antibody and antibody compositions of the invention are administered in combination with steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685), ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucocorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants may be used to prevent rejection of organ or bone marrow transplantation.

In other embodiments, the compositions of the invention are administered in combination with immunostimulants including, but not limited to, levamisole (e.g., ERGAMISOL™), isoprinosine (e.g., INOSIPLEX™), interferons (e.g., interferon alpha), and interleulins (e.g., IL-2).

In other embodiments, antibody compositions of the invention may be administered in combination with anti-opportunistic infection agents. Anti-opportunistic agents that may be administered in combination with the albumin fusion proteins and/or polynucleotides of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF).

Additional Combination Therapies

The antibodies of the invention (including molecules comprising, or alternatively consisting of, antibody fragments or variants thereof) may be administered alone or in combination with other therapeutic or prophylactic regimens (e.g., radiation therapy, chemotherapy, hormonal therapy, immunotherapy, anti-tumor agents, anti-angiogenesis and anti-inflammatory agents). Such combinatorial therapy may be administered sequentially and/or concomitantly.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the antibody and antibody compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243-248 (1981); Kurtz, FEBS Letters, 14a:105-108 (1982); McGonigle et al., Kidney Int., 25:437-444 (1984); and Pavlovic-Kantera, Expt. Hematol., 8(supp. 8) 283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383-391 (1982); Shahidi, New Eng. J. Med., 289:72-80 (1973); Urabe et al., J. Exp. Med., 149:1314-1325 (1979); Billat et al., Expt. Hematol., 10:135-140 (1982); Naughton et al., Acta Haemat, 69:171-179 (1983); Cognote et al. in abstract 364, Proceedings 7th Intl. Cong. of Endocrinology (Quebec City, Quebec, Jul. 1-7, 1984); and Rothman et al., 1982, J. Surg. Oncol., 20:105-108 (1982). Methods for stimulating hematopoiesis comprise administering a hematopoietically effective amount (i.e., an amount which effects the formation of blood cells) of a pharmaceutical composition containing polynucleotides and/or poylpeptides of the invention (and/or agonists or antagonists thereof) to a patient. The polynucleotides and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the antibody and antibody compositions of the invention are administered in combination with hematopoietic growth factors. Hematopoietic growth factors that may be administered with the antibody and antibody compositions of the invention include, but are not limited to, LEUKINE™ (SARGRAMOSTIM™) and NEUPOGEN™ (FILGRASTIM™).

In an additional embodiment, the antibody and antibody compositions of the invention are administered alone or in combination with an anti-angiogenic agent(s). Anti-angiogenic agents that may be administered with the antibody and antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman *J Pediatr. Surg.* 28:445-51 (1993)); an integrin alpha v beta 3 antagonist (C. Storgard et al., *J Clin. Invest.* 103:47-54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC359555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3540) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibody and antibody compositions of the invention include, but are not limited to, AG-3540 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with the antibody and antibody compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the antibody and antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the antibody and antibody compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of antibody and antibody compositions of the invention in combination with anti-angiogenic agents is contemplated for the treatment, prevention, and/or amelioration of cancers and other hyperproliferative disorders.

In certain embodiments, antibody and antibody compositions of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the Therapeutics of the invention, include, but are not limited to, VIRAMUNE™ (nevirapine), RESCRIPTOR™ (delavirdine), and SUS- TIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In a further embodiment, the antibody and antibody compositions of the invention are administered in combination with an antibiotic agent. Antibiotic agents that may be administered with the antibody and antibody compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

In other embodiments, antibody and antibody compositions of the invention may be administered in combination with anti-opportunistic infection agents. In a specific embodiment, antibody and antibody compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, antibody and antibody compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, antibody and antibody compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, antibody and antibody compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, antibody and antibody compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, antibody and antibody compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, antibody and antibody compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, antibody and antibody compositions of the invention are used in any combination with LEUCOVORIN™ and/or NEUPOGEN™ to prophylactically treat, prevent, and/or diagnose an opportunistic bacterial infection.

In a preferred embodiment, the antibody and antibody compositions of the invention are administered in combination with steroid therapy. Steroids that may be administered in combination with the antibody and antibody compositions of the invention, include, but are not limited to, oral corticosteroids, prednisone, and methylprednisolone (e.g., IV methylprednisolone). In a specific embodiment, antibody and antibody compositions of the invention are administered in combination with prednisone.

In an additional embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

The antibodies and antibody compositions of the invention may be administered alone or in combination with other adjuvants. Adjuvants that may be administered with the antibody and antibody compositions of the invention include, but are not limited to, alum, alum plus deoxycholate (ImmunoAg), MTP-PE (Biocine Corp.), QS21 (Genentech, Inc.), BCG, and MPL. In a specific embodiment, antibody and antibody compositions of the invention are administered in combination with alum. In another specific embodiment, antibody and antibody compositions of the invention are administered in combination with QS-21. Further adjuvants that may be administered with the antibody and antibody compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the antibody and antibody compositions of the invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, antibody and antibody compositions of the invention are used in combination with PNEUMOVAX-23™ to treat, prevent, and/or diagnose infection and/or any disease, disorder, and/or condition associated therewith. In one embodiment, antibody and antibody compositions of the invention are used in combination with PNEUMOVAX-23™ to treat, prevent, and/or diagnose any Gram positive bacterial infection and/or any disease, disorder, and/or condition associated therewith. In another embodiment, antibody and antibody compositions of the invention are used in combination with PNEU- MOVAX-23™ to treat, prevent, and/or diagnose infection and/or any disease, disorder, and/or condition associated with one or more members of the genus *Enterococcus* and/or the genus *Streptococcus*. In another embodiment, antibody and antibody compositions of the invention are used in any combination with PNEUMOVAX-23™ to treat, prevent, and/or diagnose infection and/or any disease, disorder, and/or condition associated with one or more members of the Group B *streptococci*. In another embodiment, antibody and antibody compositions of the invention are used in combination with PNEUMOVAX-23™ to treat, prevent, and/or diagnose infection and/or any disease, disorder, and/or condition associated with *Streptococcus pneumoniae*.

In a preferred embodiment, the antibody and antibody compositions of the invention are administered in combination with CD40 ligand (CD40L), a soluble form of CD40L (e.g., AVREND™), bioloigically active fragments, variants, or derivatives of CD40L, anti-CD40L antibodies (e.g., agonistic or antagonistic antibodies), and/or anti-CD40 antibodies (e.g., agonistic or antagonistic antibodies).

In a preferred embodiment, the antibody and antibody compositions of the invention are administered in combination with an NSAID.

In a nonexclusive embodiment, the antibody and antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-714 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-671 (Merck), ST-1482 (Sigma-Tau), and butixocort propionate (Warner Lambert).

In a preferred embodiment, the antibody and antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug, cyclophosphamide, chlorambucil, gold, ENBREL™ (Etanercept), anti-TNF antibody, LJP 394 (La Jolla Pharmaceutical Company, San Diego, Calif.) and prednisolone.

In an additional embodiment, antibody and antibody compositions of the invention are administered alone or in combination with one or more intravenous immune globulin preparations. Intravenous immune globulin preparations that may be administered with the antibody and antibody compositions of the invention include, but not limited to, GAMMAR™, IVEEGAM™, SANDOGLOBULIN™, GAMMAGARD S/D™, and GAMIMUNE™. In a specific embodiment, antibody and antibody compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the antibody and antibody compositions of the invention are administered in combination with cytokines. Cytokines that may be administered with the antibody and antibody compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In preferred embodiments, antibody and antibody compositions of the invention are administered with CK-B4. In another embodiment, antibody and antibody compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the antibody and antibody compositions of the invention are administered in combination with IL4 and IL10.

In one embodiment, the antibody and antibody compositions of the invention are administered in combination with one or more chemokines. In specific embodiments, the antibody and antibody compositions of the invention are administered in combination with an α(CxC) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In another embodiment, the antibody and antibody compositions of the invention are administered with chemokine beta-8, chemokine beta-1, and/or macrophage inflammatory protein-4. In a preferred embodiment, the antibody and antibody compositions of the invention are administered with chemokine beta-8.

In an additional embodiment, the antibody and antibody compositions of the invention are administered in combination with an L-4 antagonist. IL-4 antagonists that may be administered with the antibody and antibody compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL-4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the antibody and antibody compositions of the invention are administered in combination with fibroblast growth factors. Fibroblast growth factors that may be administered with the antibody and antibody compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce tumor formation in in vitro, ex vivo and in vivo assays. Antibodies or compositions of the invention can also be tested for their ability to inhibit viral replication or reduce viral load in in vitro and in vivo assays. Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with cancer, an immune disorder (e.g., an inflammatory disease), a neurological disorder or an infectious disease. Antibodies or compositions of the invention can also be tested for their ability to decrease the time course of the infectious disease. Further, antibodies or compositions of the invention can be tested for their ability to increase the survival period of animals suffering from disease or disorder, including cancer, an immune disorder or an infectious disease. Techniques known to those of skill in the art can be used to analyze the function of the antibodies or compositions of the invention in vivo.

Efficacy in treating or preventing viral infection may be demonstrated by detecting the ability of an antibody or composition of the invention to inhibit the replication of the virus, to inhibit transmission or prevent the virus from establishing itself in its host, or to prevent, ameliorate or alleviate the symptoms of disease a progression. The treatment is considered therapeutic if there is, for example, a reduction in viral load, amelioration of one or more symptoms, or a decrease in mortality and/or morbidity following administration of an antibody or composition of the invention.

Antibodies or compositions of the invention can be tested for their ability to modulate the biological activity of immune cells by contacting immune cells, preferably human immune cells (e.g., T cells, B-cells, and Natural Killer cells), with an antibody or composition of the invention or a control compound and determining the ability of the antibody or compostion of the invention to modulate (i.e, increase or decrease) the biological activity of immune cells. The ability of an antibody or composition of the invention to modulate the biological activity of immune cells can be assessed by detecting the expression of antigens, detecting the proliferation of immune cells (i.e., T-cell proliferation), detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the ability of an antibody or composition of the invention to induce cell proliferation is measured. In another preferred embodiment, the ability of an antibody or composition of the invention to modulate chemotaxis is measured.

Panels/Mixtures

The present invention also provides for mixtures of antibodies (including scFvs and other molecules comprising, or alternatively consisting of, antibody fragments or variants thereof) that specifically bind to CK-B4 or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to CK-B4 or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to CK-B4 or a fragment or variant thereof, wherein the panel has at least one, two, three, four, five or more different antibodies of the invention. In specific embodiments, the invention provides for panels of antibodies that have different affinities for CK-B4, different specificities for CK-B4, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains of a one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a VH domain of one or more of the scFvs referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a VH domain of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a VH domain of one or more of the scFvs referred to in Table 1, or a variant thereof.

Other embodiments of the present invention providing for compositions comprising, one or more antibodies (including molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of one or more of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that specifically binds to CK-B4 polypeptides or fragments or variants thereof. In a specific embodiment, the kits of the present invention contain a substantially isolated CK-B4 polypeptide or fragment or variant thereof as a control. Preferably, the kits of the present invention further comprise a control antibody which does not react with any, some or all CK-B4. In another specific embodiment, the kits of the present invention contain a means for detecting the binding of an antibody to CK-B4 polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized CK-B4. The CK-B4 provided in the kit may also be attached to a solid support. In a more specific embodiment the detecting means of the above-described kit includes a solid support to which CK-B4 is attached. Such a kit may also include a non-attached reporter-labeled anti-human antibody. In this embodiment, binding of the antibody to CK-B4 can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with CK-B4, and means for detecting the binding of CK-B4 polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound CK-B4 obtained by the methods of the present invention. After CK-B4 polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-CK-B4 antibody on the solid support. Typically, the reporter is an enzyme which is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant CK-B4, and a reporter-labeled anti-human antibody for detecting surface-bound anti-CK-B4 antibody.

Gene Therapy

In a specific embodiment, nucleic acids comprising sequences encoding antibodies or functional derivatives thereof, are administered to diagnose, treat, inhibit or prevent a disease or disorder associated with aberrant expression and/or activity of CK-B4 and/or its receptors (e.g., CCR6), by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 1 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g. PCT Publications WO 92/06180; WO 92/22715; WO92/203 16; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Having generally described the invention, the same will be more readily understood by reference to the following examples, which are provided by way of illustration and are not intended as limiting.

EXAMPLES

Example 1

Generation of Anti-CK-B4 Antibodies

General Methods

Rescue of the Library.

A library of scFvs is constructed from the RNA of human PBLs as described in WO92/01047 (which is hereby incorporated by reference in its entirety). To rescue phage displaying antibody fragments, approximately 109 $E.$ $coli$ harboring the phagemid are used to inoculate 50 ml of 2×TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 micrograms ampicillin/ml and 25 micrograms kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in bicarbonate buffer, pH 9.0 or PBS with 1-4 ml of either 10-100 micrograms/ml of a CK-B4 polypeptide. When bicarbonate buffer, pH 9.0 is used as the coating buffer, allowing CK-B4 to dry onto the immunotube is preferable. Alternatively, the immunotube can be coated with a polyclonal anti-CK-B4 antibody, such as, for example, the polyclonal available from R&D Systems (Minneapolis, Minn.). Then, CK-B4 protein 0.5-10 micrograms/ml) is loaded onto the anti-CK-B4 coated immunotube. After a washing step to remove unbound CK-B4 polypeptides, such immunotubes may be used to pan the scFv library.

Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 micrograms/ml ampicillin. The resulting bacterial library is then rescued with delta gene 3 helper phage as described above to prepare phage for a subsequent round of selection. This process is usually repeated for a total of 2-4 rounds of affinity purification.

Characterization of Binders.

Eluted phage from the final rounds of selection are used to infect $E.$ $coli$ HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 2

Identification and Cloning of VH and VL Domains

One method to identfy and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may lysed in the TRIzol® reagent (Life Technologies, Rockville, Md.) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Follwing washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transciptase and random hexamer primers. cDNA is then used as a template for PCR amplification of VH and VL domains. Alternatively, DNA encoding an scFv, e.g., a vector containing the scFv expression construct, may be used as template material for the following PCR reaction. Primers used to amplify VH and VL genes are shown in Table 4. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerse, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 4

Primer Sequences Used to Amplify VH and VL domains.

| Primer name | SEQ ID NO | Primer Sequence (5'-3') |
|---|---|---|
| VH Primers | | |
| Hu VH1-5' | 37 | CAGGTGCAGCTGGTGCAGTCTGG |
| Hu VH2-5' | 38 | CAGGTCAACTTAAGGGAGTCTGG |

TABLE 4-continued

Primer Sequences Used to Amplify VH and VL domains.

| Primer name | SEQ ID NO | Primer Sequence (5'-3') |
|---|---|---|
| Hu VH3-5' | 39 | GAGGTGCAGCTGGTGGAGTCTGG |
| Hu VH4-5' | 40 | CAGGTGCAGCTGCAGGAGTCGGG |
| Hu VH5-5' | 41 | GAGGTGCAGCTGTTGCAGTCTGC |
| Hu VH6-5' | 42 | CAGGTACAGCTGCAGCAGTCAGG |
| Hu JH1, 2-5' | 43 | TGAGGAGACGGTGACCAGGGTGCC |
| Hu JH3-5' | 44 | TGAAGAGACGGTGACCATTGTCCC |
| Hu JH4, 5-5' | 45 | TGAGGAGACGGTGACCAGGGTTCC |
| Hu JH6-5' | 46 | TGAGGAGACGGTGACCGTGGTCCC |
| VL Primers | | |
| Hu Vkappa1-5' | 47 | GACATCCAGATGACCCAGTCTCC |
| Hu Vkappa2a-5' | 48 | GATGTTGTGATGACTCAGTCTCC |
| Hu Vkappa2b-5' | 49 | GATATTGTGATGACTCAGTCTCC |
| Hu Vkappa3-5' | 50 | GAAATTGTGTTGACGCAGTCTCC |
| Hu Vkappa4-5' | 51 | GACATCGTGATGACCCAGTCTCC |
| Hu Vkappa5-5' | 52 | GAAACGACACTCACGCAGTCTCC |
| Hu Vkappa6-5' | 53 | GAAATTGTGCTGACTCAGTCTCC |
| Hu Vlambda1-5' | 54 | CAGTCTGTGTTGACGCAGCCGCC |
| Hu Vlambda2-5' | 55 | CAGTCTGCCCTGACTCAGCCTGC |
| Hu Vlambda3-5' | 56 | TCCTATGTGCTGACTCAGCCACC |
| Hu Vlambda3b-5' | 57 | TCTTCTGAGCTGACTCAGGACCC |
| Hu Vlambda4-5' | 58 | CACGTTATACTGACTCAACCGCC |
| Hu Vlambda5-5' | 59 | CAGGCTGTGCTCACTCAGCCGTC |
| Hu Vlambda6-5' | 60 | AATTTTATGCTGACTCAGCCCCA |
| Hu Jkappa1-3' | 61 | ACGTTTGATTTCCACCTTGGTCCC |
| Hu Jkappa2-3' | 62 | ACGTTTGATCTCCAGCTTGGTCCC |
| Hu Jkappa3-3' | 63 | ACGTTTGATATCCACTTTGGTCCC |
| Hu Jkappa4-3' | 64 | ACGTTTGATCTCCACCTTGGTCCC |
| Hu Jkappa5-3' | 65 | ACGTTTAATCTCCAGTCGTGTCCC |
| Hu Jlambda1-3' | 66 | CAGTCTGTGTTGACGCAGCCGCC |
| Hu Jlambda2-3' | 67 | CAGTCTGCCCTGACTCAGCCTGC |
| Hu Jlambda3--3' | 68 | TCCTATGTGCTGACTCAGCCACC |
| Hu Jlambda3b-3' | 69 | TCTTCTGAGCTGACTCAGGACCC |
| Hu Jlambda4-3' | 70 | CACGTTATACTGACTCAACCGCC |
| Hu Jlambda5-3' | 71 | CAGGCTGTGCTCACTCAGCCGTC |
| Hu Jlambda6-3' | 72 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art.

Example 3

Detecting Inhibition of Intracellular Calcium Flux Using Anti-CK-β4 Antibodies

General Methods

Evidence suggests that both CC and CXC chemokines are able to elicit their functional responses via the signaling pathway controlled by the phophoinositide 3-kinase (PI3K) family (Curnock et al., *Immunology* 105:125-136 (2002)). Binding of CK-β4 to its receptor (e.g., CCR6), may therefore alter intracellular levels of calcium. These alterations can be measured in an assay using Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells transfected with a CK-β4 receptor, seed the cells at $1\text{-}2\times10^5$ cells/well in a Co-star black 96-well plate with clear bottom. The plate is incubated in a $CO_2$ incubator for 20 hours. The adherent cells are washed two times in Biotek washer with 200 microliters of HBSS (Hank's Balanced Salt Solution) leaving 100 microliters of buffer after the final wash.

A stock solution of 1 mg/ml fluo-4 is made in 10% pluronic acid in DMSO. To load the cells with fluo-4, 50 microliters of 12 ug/ml fluo-4 is added to each well. The plate is incubated at 37 degrees C. in a $CO_2$ incubator for 60 min. The plate is washed four times in the Biotek washer with HBSS leaving 100 microliters of buffer.

For non-adherent cells transfected with a CK-β4 receptor, the cells are spun down from culture media. Cells are re-suspended to $2\text{-}5\times10^6$ cells/ml in HBSS in a 50-ml conical tube. Four microliters of 1 mg/ml fluo-4 solution in 10% pluronic acid DMSO is added to each ml of cell suspension. The tube is then placed in a 37 degrees C. water bath for 30-60 min. The cells are washed twice with HBSS, resuspended to $1\times10^6$ cells/ml, and dispensed into a microplate, 100 microliters/well. The plate is centrifuged at 1000 rpm for 5 min. The plate is then washed once in Denley Cell Wash with 200 microliters HBSS, followed by an aspiration step to 100 microliter final volume.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488 nm; and (5) Emission is 530 nm. The first sample addition consists of 4 microliters of Buffer only or a solution of Buffer and anti-CK-β4. The second addition consists of 6 microliters of CK-β4. Appropriate concentrations of CK-β4 and/or CK-β4 antisera can be determined by one of ordinary skill in the art. Increased emission at 530 nm indicates an extracellular signaling event caused by CK-β4 or a molecule induced by CK-β4, which has resulted in an increase in the intracellular $Ca^{++}$ concentration.

Alternative Method:

A similar assay to determine the ability of antibodies of the invention to inhibit calcium flux induced by CK-B4 can be performed on activated T cells obtained from human donors.

Purification of and Activation of T Cells.

First, peripheral blood mononuclear cells must be purified from whole blood. A pack of blood usually contains 500 ml. Place 20 ml aliquots into 50 ml polypropylene tubes, ands add 10 ml to 1×PBS without calcium and without magnesium (Biofluids Cat # P312-000) to each tube. Underlay diluted blood samples with 14.5 ml Lymphocyte Separation Medium (LSM; ICN Biochemical Cat # 50494), then spin in a tabletop centrifuge at 1800 rpm for 30 min. at room temperature with brake off. Once spin is complete, aspirate interface material (about 10 milliliters) and place into a separate 50 ml tube (two interfaces may be placed in one tube). Add PBS to the tube until the total volume is 50 ml. Spin at 2000 rpm for 5 minutes. Aspirate supernatant. Next, add 5 ml of sterile water to each tube and gently mix for 20 seconds, then fill tube to 50 ml with PBS. Spin at 1800 rpm for 5 minutes. Aspirate supernatant. Combine the cells into a 50 ml tube. Filter the cells through a 70 micrometer filter to remove the clumps. At this point, cells should be counted.

T cells are purified from PBMC using a nylon wool column. In this particular procedure a 10 ml nylon wool column such as the one available from Polysciences, Inc., (Warrington, Pa.; Cat No. 21759) can be used. Remove the stopcock from sterile packaging and place on tip of syringe column. Wash the column with 37° C. complete RPMI 1640 medium (RPMI 1640 supplemented with 10% fetal bovine serum, 1× Penicillin-Streptomycin and 1× Glutamine). 100× solutions of Penicillin-Streptomycin and Glutamine are available from Biosource (Camarillo, Calif.). Tap column gently while washing to ensure wool is wetted and free of air bubbles. Close stopcock and incubate column with media for one hour at 37° C. At the end of the hour, open stopcock and drain media to the top of the nylon wool column and close. Add $1\text{-}2\times10^8$ viable cells per column in a volume of 2 ml of media. Open stopcock and allow media to drain until cell volume has entered the packed wool. Close stopcock. Add another 2-5 ml of media to column to ensure that the top of the wool is covered with media Incubate for 1 hour at 37° C. Collect non adherent T-cells by using two washes. Wash cells and count cells. The yield after one column ($2\times10^8$ cells) is about $50\times10^6$. Adjust cells to $2\times10^6$/ml. At this point, a sample of cells may be set aside and analyzed for CCR6 expression via FAC analysis, if desired.

To activate purified T cells, place purified T cells in T75 tissue culture flask and add recombinant human IL2 at 1000 units/ml to each flask. Incubate for three days at 37° C. At the end of three days wash cells and replate at $2\times10^6$ cells/ml in media containing 1000 units/ml IL2. Repeat this step on days 3 and 6. On day 7, cells should be analyzed for CCR6 and CD3 expression by FACS analysis. Cells may also be used in calcium flux assay described below.

Calcium Flux Assay

Activated IL-2 T cells are suspended at $5\times10^6$/ml in pH 7.4 calcium buffer (20 mM Hepes buffer, 125 mM NaCl, 5 mM KCl, 0.5 mM Glucose, 1 mM $CaCl_2$, 1 mM $MgCl_2$ and 0.025% BSA). One microliter of Fura-2, AM (50 micrograms dissolved in 25 microliters of DMSO) is added per 2 ml of the cell suspension. The cells are then incubated for 30 minutes at room temperature in the dark. Cells are washed twice with calcium buffer and suspended at 1 million cells/ml in calcium buffer after incubation. Two mls of the cell suspension are placed in a continuously stirring cuvette at 37 C. $[Ca^{++}]_{Initial}$ is measured using dual excitation wavelength 340 nm and 380 nm, a single emission wavelength 510 nm on Hitachi spectrophotometer. The baseline is established for 60 seconds before adding the test antibody. Add 20 microliters of test antibody (100× of the final concentration) to the cuvette and record the time. CK-B4 at a final concentration of about 5-10 micrograms/ml is added 60 seconds after addition of test antibody. The concentration of CK-B4 is determined by performing a calcium flux assay in the absence of antibody and using the lowest concentration of CK-B4 that gives a strong calcium response. Recording of the fluorescence in the spectrophotometer is continued until the fluorescence returns to baseline levels. Whole IgG1 antibodies comprising the VH and VL domains of the F003A09, F002G03, F0076F10, F003F09, and F0081C09 were able to inhibit the calcium flux induced by 5-10 micrograms/ml of CKB4 when tested at concentrations of 10 micrograms/ml. Some antibodies exhibited activity at concentrations less than 10 micrograms/ml.

Example 4

Inhibition of CK-β-4-Mediated Chemotaxis Using CK-β4 Antibodies

General Methods

Cell migration assays are performed using a 48 well microchemotaxis chamber (Neuroprobe Inc., Cabin John, M D; Falk, W., et al., J. Immunological Methods 1980; 33:239-247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. CK-β4 is diluted to appropriate concentrations in M199 supplemented with 0.25% bovine serum albumin (BSA), and 25 microliters of the final dilution is placed in the lower chamber of the modified Boyden apparatus. Subconfluent, early passage (2-6) cell cultures of lymphocytes are washed and trypsinized for the minimum time required to achieve cell detachment. After placing the filter between lower and upper chamber, $2.5 \times 10^5$ cells suspended in 50 microliters M199 containing 1% FBS are seeded in the upper compartment. For lymphocyte chemotaxis, the membranes are coated with 20 ug/ml fibronectin (Life Technologies, Inc.) for 24 h at 4 degrees C. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution Diff-Quick, Baxter, McGraw Park, Ill.). Migration is quantified by counting cells of three random high-power fields (40×) in each well, and all groups are performed in quadruplicate. One skilled in the art could easily modify the exemplified studies to test other cell types or to test for inhibition of cell migration through the addition of CK-β4 antibodies of the invention in test wells.

Example 5

Competitive Inhibition of $^{125}$I-CK-B4 Binding to CCR6 Membranes

The ability of anti-CK-B4 antibodies of the invention to inhibit the binding of CK-B4 to CCR6 may be tested in the following assay. This assay is performed in 96-well plates and each sample is tested in triplicate. A 1:3 serial dilution of anti-CK-B4 antibody is made starting with 200 nM solution of anti-CK-B4 antibody in binding buffer (50 mM HEPES, pH7.0, 5 mM MgCl$_2$, 1 mM CaCl$_2$, 0.5% protease free BSA, 0.033% CHAPS, 0.05% Tween 20, 0.05% sodium azide). To fifty microliters of each dilution of antibody are added 25 microliters of CCR6 membranes (40 micrograms/ml in binding buffer; available from Upstate Biotechnology, Charlottesville, Va. Catalog number 50-139M.) Lastly 25 microliters of $^{125}$I-CK-B4 (0.8 nM in binding buffer) are added to the wells containing the mixture of antibody and membranes, making for a 100 microliter reaction volume. Total binding is measured using 50 microliters of binding buffer in lieu of 50 microliters of antibody dilution.

The reaction is incubated for 3 hours at room temperature. The plates are harvested in a Tomtec Cell Harvester. The reaction is washed through a filtermat B (Perkin Elmer Life Sciences, Inc. Boston, Mass. product Number 1450-521) presoaked in 0.3% polyethyliamine using an ice cold wash buffer (25 mM Hepes, 5 mM MgCl$_2$, 1 mM CaCl$_2$, 0.5M NaCl, and 0.05% Tween 20). The filter is then dried and radioactivity bound to the filter is measured using a Wallac MicroBeta Trilux (Perlin Elmer Life Sciences, Inc.).

Table 4 gives the EC-50 values for inhibition of $^{125}$I CK-B4 binding by IgG1 antibodies comprising the VH and VL domains of the scFvs described in Table 1. Data was obtained in three separate experiments indicated by Expt. 1, Expt. 2 and Expt. 3.

TABLE 5

| Antibody | EC50 (nM) |
|---|---|
| F003A09 | 0.30 Expt 1 |
|  | 0.46 Expt 3 |
| F081C09 | 0.09 Expt 2 |
| F076F10 | 0.49 Expt 2 |
| F076C06 | 1.80 Expt 3 |
| F003F01 | 0.20 Expt 1 |
|  | 0.13 Expt 3 |
| F002G03 | 4.10 Expt 1 |
| F003F09 | 2.4 Expt 2 |
| F002C08 | 2.20 Expt 3 |
| F002D02 | 4.50 Expt 3 |
| F076G06 | 1.70 Expt 3 |
| Irrelevant IgG1 negative control | No inhibition observed |

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosure (including the specification, sequence listing, and drawings) of Provisional Application No. 60/376,561 filed May 1, 2002 is herein incorporated by reference in its entirety.

What is claimed is:

1. An isolated antibody or fragment thereof comprising:
   (a) the amino acid sequence of the VHCDR1, VHCDR2, VHCDR3, VLCDR1, VLCDR2, and VLCDR3 domains of the scFv of SEQ ID NO:20;
   (b) the amino acid sequences sequence of the VH and VL domains of the scFv of SEQ ID NO:20; or
   (c) the amino acid sequence of the scFv of SEQ ID NO:20;
   wherein said antibody or fragment thereof specifically binds a CK-B4 polypeptide consisting of amino acids 25 to 96 of SEQ ID NO:2.

2. The antibody or fragment thereof of claim 1, which comprises (a).

3. The antibody or fragment thereof of claim 1, which comprises (b).

4. The antibody or fragment thereof of claim 1, which comprises (c).

5. The antibody or fragment thereof of claim 1, wherein said CK-B4 polypeptide is purified from a cell culture.

6. The antibody of claim 1 which is a whole immunoglobulin molecule, monoclonal, human, chimeric, or humanized.

7. The antibody fragment of claim 1 which is an scFv, a Fab fragment, an Fab' fragment, an F(ab')2, an Fv, or a disulfide linked Fv.

8. The antibody or fragment thereof of claim 1 which comprises a heavy chain immunoglobulin constant domain selected from the group consisting of:
   (a) a human IgM constant domain;
   (b) a human IgG1 constant domain;
   (c) a human IgG2 constant domain;
   (d) a human IgG3 constant domain;
   (e) a human IgG4 constant domain; and
   (f) a human IgA constant domain.

9. The antibody or fragment thereof of claim 1 which comprises a light chain immunoglobulin constant domain selected from the group consisting of:
   (a) a human Ig kappa constant domain; and
   (b) a human Ig lambda constant domain.

10. The antibody or fragment thereof of claim 1, wherein the antibody or fragment thereof is conjugated to a detectable label.

11. The antibody or fragment thereof of claim 10, wherein the detectable label is a radiolabel.

12. The antibody or fragment thereof of claim 11, wherein the radiolabel is $^{125}$I, $^{131}$I, $^{111}$In, $^{90}$Y, $^{99}$Tc, $^{177}$Lu, $^{166}$Ho, $^{153}$Sm, $^{215}$Bi, or $^{225}$Ac.

13. The antibody or fragment thereof of claim 10, wherein the detectable label is an enzyme, a fluorescent label, a luminescent label, or a bioluminescent label.

14. The antibody or fragment thereof of claim 1, wherein the antibody or fragment thereof is biotinylated.

15. The antibody or fragment thereof of claim 1, wherein the antibody or fragment thereof is conjugated to a therapeutic or cytotoxic agent.

16. The antibody or fragment thereof of claim 1, wherein the antibody or fragment thereof is attached to a solid support.

17. The antibody or fragment thereof of claim 1, wherein the antibody or fragment thereof specifically binds said CK-B4 polypeptide in a Western blot.

18. The antibody or fragment thereof of claim 1, wherein the antibody or fragment thereof specifically binds said CK-B4 polypeptide in an ELISA.

19. An isolated cell that produces the antibody or fragment thereof of claim 1.

20. The antibody or fragment thereof of claim 1 which inhibits the activity of said CK-B4 polypeptide.

21. The antibody or fragment thereof of claim 1 which diminishes or abolishes the ability of said CK-B4 polypeptide to bind to a CK-B4 receptor.

22. The antibody or fragment thereof of claim 1 which diminishes or abolishes the ability of said CK-B4 polypeptide to bind to CCR6.

23. The antibody or fragment thereof of claim 1 which inhibits or abolishes the ability of said CK-B4 polypeptide to induce chemotaxis, proliferation, or calcium flux of a cell expressing a CK-B4 receptor.

24. The antibody or fragment thereof of claim 1 which inhibits or abolishes the ability of said CK-B4 polypeptide to induce chemotaxis, proliferation, or calcium flux of a cell expressing CCR6.

25. The antibody or fragment thereof of claim 1 in a pharmaceutically acceptable carrier.

26. A kit comprising the antibody or fragment thereof of claim 1.

27. The kit of claim 26, wherein the antibody or fragment thereof is conjugated to a detectable label.

28. A method of treating or ameliorating psoriasis, comprising administering to an animal in need thereof, the antibody or fragment thereof of claim 1 in an amount effective to treat or ameliorate psoriasis.

29. An isolated scFv comprising the amino acid sequence of SEQ ID NO:20.

* * * * *

SEQUENCE LISTING

<160> NUMBER OF SEQ ID NOS: 72

<210> SEQ ID NO 1
<211> LENGTH: 291
<212> TYPE: DNA
<213> ORGANISM: Homo Sapiens
<220> FEATURE:
<221> NAME/KEY: CDS
<222> LOCATION: (1)..(288)

<400> SEQUENCE: 1 atg tgc tgt acc aag agt ttg ctc ctg gct gct ttg atg tca gtg ctg      48

```
Met Cys Cys Thr Lys Ser Leu Leu Ala Ala Leu Met Ser Val Leu
 1               5                  10                  15 cta ctc cac ctc tgc ggc gaa tca gaa gca gca agc aac ttt gac tgc      96
Leu Leu His Leu Cys Gly Glu Ser Glu Ala Ala Ser Asn Phe Asp Cys
             20                  25                  30 tgt ctt gga tac aca gac cgt att ctt cat cct aaa ttt att gtg ggc     144
Cys Leu Gly Tyr Thr Asp Arg Ile Leu His Pro Lys Phe Ile Val Gly
             35                  40                  45 ttc aca cgg cag ctg gcc aat gaa ggc tgt gac atc aat gct atc atc     192
Phe Thr Arg Gln Leu Ala Asn Glu Gly Cys Asp Ile Asn Ala Ile Ile
         50                  55                  60 ttt cac aca aag aaa aag ttg tct gtg tgc gca aat cca aaa cag act     240
Phe His Thr Lys Lys Lys Leu Ser Val Cys Ala Asn Pro Lys Gln Thr
 65                  70                  75                  80 tgg gtg aaa tat att gtg cgt ctc ctc agt aaa aaa gtc aag aac atg     288
Trp Val Lys Tyr Ile Val Arg Leu Leu Ser Lys Lys Val Lys Asn Met
                 85                  90                  95 taa                                                                  291

<210> SEQ ID NO 2
<211> LENGTH: 96
<212> TYPE: PRT
<213> ORGANISM: Homo Sapiens

<400> SEQUENCE: 2

Met Cys Cys Thr Lys Ser Leu Leu Ala Ala Leu Met Ser Val Leu
 1               5                  10                  15

Leu Leu His Leu Cys Gly Glu Ser Glu Ala Ala Ser Asn Phe Asp Cys
             20                  25                  30

Cys Leu Gly Tyr Thr Asp Arg Ile Leu His Pro Lys Phe Ile Val Gly
             35                  40                  45

Phe Thr Arg Gln Leu Ala Asn Glu Gly Cys Asp Ile Asn Ala Ile Ile
         50                  55                  60

Phe His Thr Lys Lys Lys Leu Ser Val Cys Ala Asn Pro Lys Gln Thr
 65                  70                  75                  80

Trp Val Lys Tyr Ile Val Arg Leu Leu Ser Lys Lys Val Lys Asn Met
                 85                  90                  95

<210> SEQ ID NO 3
<211> LENGTH: 750
<212> TYPE: DNA
<213> ORGANISM: Artificial sequence
<220> FEATURE:
<223> OTHER INFORMATION: DNA encoding F003A09 scFv

<400> SEQUENCE: 3
caggtccagc tggtacagtc tggggctgag gtgaagaagg ctgggtcctc ggtgaaggtc      60
tcctgcaagg cctctggaga caccttcagc aactttgcta tcagctgggt gcgacaggcc     120
cctggacacg gcttgagtg gtgggaggg atcatccctg tcttcaacac ggctgactac     180
gcacagaatt tcacggacag agtcacgatt ccgcggaca aagccacgaa gacagtctac     240
atggaactgc gcagcctgag atctgacgac acggccgtat atttctgtgc gaggacgaaa     300
atcgaactgg acaatgatgc ctttgatatc tggggccaag caccctggt caccgtctcg     360 agtggaggcg gcggttcagg cggaggtggc tctggcggtg gcggaagtgc acagcctgtg     420
ctgactcagc caccctcagc gtctgggacc ccgggcaga gggtcaccat ctcttgttct     480
ggaagcagct ccaacatcgg aagtaatact gtaaactggt accagcagct cccaggaacg     540
```

```
gcccccaaac tcctcatcta tagtaataat cagcggccct cagggggtccc tgaccgattc      600 tctggctcca agtctggcac ctcagcctcc ctggccatca gtgggctcca gtctgaggat      660
gaggctgatt attactgtgc agcatgggat gacagcctga atggtccttt ttgggtgttc      720
ggcggaggga ccaagctgac cgtcctaggt                                       750
```

<210> SEQ ID NO 4
<211> LENGTH: 735
<212> TYPE: DNA
<213> ORGANISM: Artificial Sequence
<220> FEATURE:
<223> OTHER INFORMATION: DNA encoding F081C09 scFv

<400> SEQUENCE: 4

```
caggtgcagc tggtgcaatc tggggctgag gtgaagaagc ctgggtcctc ggtgagggtc       60
tcctgcaagg cgtctggagg cagcttcagc gactatgcta tccactgggt gcgacaggcc      120
cctggacaag gcttgagtg gatgggaggg atcatccccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagaagcg      300
cagtatgatg atgcttttga tatctgggc caaaggacaa tggtcaccgt ctcttcaggt      360
ggaggcggtt caggcggagg tggcagcggc ggtggcggat cgcagtctgt gttgacgcag      420
ccgccctcag tgtctgcggc cccaggacag aaggtcacca tttcctgctc tggaagcacc      480
tccaacattg gaataatta tgtctcctgg taccaacagc acccaggcaa agccccccaaa      540 ctcatgattt atgatgtcag taagcggccc tcaggggtcc ctgaccgatt ctctggctcc      600
aagtctggca actcagcctc cctggacatc agtgggctcc agtctgagga tgaggctgat      660
tattactgtg cagcatggga tgacagcctg agtgaatttc tcttcggaac tgggaccaag      720
ctgaccgtcc taggt                                                       735
```

<210> SEQ ID NO 5
<211> LENGTH: 750
<212> TYPE: DNA
<213> ORGANISM: Artificial Sequence
<220> FEATURE:
<223> OTHER INFORMATION: DNA encoding F076F10 scFv

<400> SEQUENCE: 5

```
gaggtgcagc tggtgcagtc tggggctgag gtgaagaagc ctgggtcctc ggtgaaggtc       60
ttctgcaaga cttctggagg caccttcagc agctatgctt tcggctgggt gcgacagcgc      120
cctggacaag gcttgagtg gatgggaggg atcatccccta actttgatgc agcaaactac      180
gcacagaagt tccaggacac agtcgccttt accgcggaca catccacgaa cacactctac      240
ttggagttga gcagcctgac atctgatgac acggccgtct attactgtgc gcgagaggtc      300
ggagtgcatg ccagtggcct gggcgctttt gatatctggg gccggggcac cctggtcacc      360
gtctcgagtg gaggcggcgg ttcaggcgga ggtggctctg gcggtggcgg aagtgcacag      420
tctgtgctga cgcagccgcc ctcggtgtct ggtgccccca gcagagggt caccatctcc      480 tgttctggaa gcagctccaa catcggagat aatgttgtga attggtacca gcagctccca      540
ggaaaggctc ccaaactcct catctattat gatgatctgc tgccctcagg ggtctctgac      600
cgattctctg gctccaagtc tggcacctca gcctcctgg ccatcagtgg gctccagtct      660
gaggatgagg ctgattattt ctgtgcggca tgggatgaca gtttggatgc ttatgtcttc      720
ggaactagga ccaaggtcac cgtcctaggt                                       750
```

<210> SEQ ID NO 6
<211> LENGTH: 735
<212> TYPE: DNA
<213> ORGANISM: Artificial Sequence
<220> FEATURE:
<223> OTHER INFORMATION: DNA encoding F002D07 scFv

<400> SEQUENCE: 6

```
caggtgcagc tggtgcagtc tggggggaggc gtggtccagc ctggggggtc cctgagactc    60
tcctgtgcag cttctgggtt cattttcagt agttatggga tgcactgggt ccgccaggct   120
ccaggcaagg ggctggagtg ggtggcaggt atttttttatg atggaggtaa taaatactat   180
gcagactccg tgaagggccg attcaccatc tccagagaca attccaagaa cacgctgtat   240
ctgcaaatga acagcctgag agctgaggac acggctgtgt attactgtgc gagagatagg   300
ggctactact acatggacgt ctggggcaaa gggaccacgg tcaccgtctc tcaggtgga    360
ggcggttcag gcggaggtgg ctctggcggt ggcggatcgc agtctgtgtt gacgcagccg   420
ccctcagtgt ctggggcccc aggacagagg gtcaccatct cctgcactgg gagaagctcc   480
aacatcgggg caggtcatga tgtacactgg taccagcaac ttccaggaac agcccccaaa   540
ctcctcatct atggtgacag caatcggccc tcagggtcc ctgaccgatt ctctggctcc    600
aggtctggca cctcagcctc ctggccatc actgggctcc aggctgaaga tgaggctgat    660
tattactgcc agtcctatga cagcagcctg agggggttcgg tattcggcgg agggaccaag   720
gtcaccgtcc taggt                                                    735
```

<210> SEQ ID NO 7
<211> LENGTH: 756
<212> TYPE: DNA
<213> ORGANISM: Artificial Sequence
<220> FEATURE:
<223> OTHER INFORMATION: DNA encoding F076C06 scFv

<400> SEQUENCE: 7

```
caggtccagc tggtacagtc tgggcctgag gtgaagaagc tgggtcctc ggtgaaggtc     60
tcctgcaggg cttctggagg cacccttcagc acctatgctt tcagctgggt gcgacaggcc   120
cctggacagg ggcttgagtg gatgggagga atcatccctg tgtttgaaac accgatctac   180
gcacagaagt tacagggcag actcacgatt accgcggaca tcgacgga cacggcctac    240
atggaactga gcaacctgag atctggggac acggccgttt attactgtgc gagagagtgg   300
gggactatt acagttcagt cagttctgga gctctgcact actgggccg gggcacccctg    360
gtcaccgtct cgagtggagg cggcggttca ggcggaggtg gctctggcgg tggcggaagt   420
gcacaggctg tgctgactca gccgtcctca gcgtctggga ccccgggca gagggtcacc    480
atctcttgtt ctggaagcag ctccaacatc ggaaataatg ctgttaattg gtaccagcaa   540
ctcccaggaa cggccccaa actcctcatc tacaacaata tcagtggcc ctcagggggtc    600
cctgaccgat tctctggctc caagtctggc acctcagcct ccctggccgt cagtgggctc   660
cagtctgagg atgaggctga ttattactgt gcagcatggg atgacagcct gaatggttat   720
gtcttcggaa ctgggaccca gctcaccgtt ttaagt                             756
```

<210> SEQ ID NO 8
<211> LENGTH: 759
<212> TYPE: DNA
<213> ORGANISM: Artificial Sequence
<220> FEATURE:

<223> OTHER INFORMATION: DNA encoding F003B07 scFv

<400> SEQUENCE: 8

| | | | | | |
|---|---|---|---|---|---|
| gaggtccagc | tggtgcagtc | tggggctgaa | gtgaagaagc | ctgggtcctc | ggtgaaggtc | 60 |
| tcctgcaagg | cttctggaga | caccttcgac | agttatgctt | tcagctgggt | gcgacaggcc | 120 |
| cctggacaag | ggcttgaatg | gatgggagga | atcatcccta | tgtttgatac | accaatctac | 180 |
| gcacagaagt | tccagggcaa | agtcactatt | accgcggaca | catcaacgag | cacagtctac | 240 |
| atgaagctga | gcagcctcag | atctggtgac | acggccattt | attactgtgc | gagagagtgg | 300 |
| gggggttact | acagttcaga | gagttctgga | gctctacaat | actggggccg | ggcaccctg | 360 |
| gtcaccgtct | cgagtggagg | cggcggttca | ggcggaggtg | gctctggcgg | tggcggaagt | 420 |
| gcacaggctg | tgctgactca | gccgtcctca | gtgtctgggg | ccccagggca | gagggtcacc | 480 |
| atctcctgca | ctgggagcag | gtccaatatc | ggggctgatt | atgatgtcca | gtggtatcag | 540 |
| cagcttccag | gaacagcccc | caaactcctc | atctatggta | caacaatcg | gccctcaggg | 600 |
| gtccctgacc | gattctctgg | ctcgaagtct | gacagatcag | cctccctggc | catcactggg | 660 |
| ctccgggctg | aggatgagtc | tgattattac | tgccagtcct | atgacagcag | cctgagtgtc | 720 |
| tgggtcttcg | gcggagggac | caagctgacc | gtcctaggt | | | 759 |

<210> SEQ ID NO 9
<211> LENGTH: 744
<212> TYPE: DNA
<213> ORGANISM: Artificial Sequence
<220> FEATURE:
<223> OTHER INFORMATION: DNA encoding F003F01 scFv

<400> SEQUENCE: 9

| | | | | | |
|---|---|---|---|---|---|
| gaagtgcagc | tggtgcagtc | tggggctgag | gtgaggaagc | ctgcgtcctc | cgtgaaggtc | 60 |
| tcctgcaaga | cctctggagg | ctccttcaac | gactattctt | tcaattgggt | gcgacaggcc | 120 |
| cctggacaag | ggcttgagtg | gatgggaagt | atcatccctg | tctttgatat | ggcagactac | 180 |
| gggcagaact | tcagggtcg | actcactatt | accgcggacg | agtccacgac | cacgcctac | 240 |
| atggaactga | gcgacctgac | gcctatggac | acggccattt | attactgtgc | gagagttgcc | 300 |
| atggtgggag | cgacccactt | tgacatctgg | ggccagggaa | ccctggtcac | cgtctcgagt | 360 |
| ggaggcggcg | gttcaggcgg | aggtggctct | ggcggtggcg | gaagtgcaca | gtctgtgttg | 420 |
| acgcagccgc | cctcagcgtc | tgggacccc | gggcagaggg | tcaccatctc | ttgttctgga | 480 |
| ggcagttcca | acatcggaag | taatcctgta | aactggtacc | agcaggtccc | aggaacggcc | 540 |
| cccaaactcc | tcatttatct | tagtgatcaa | cgtcccgcag | gggttcctga | ccgattctct | 600 |
| ggctccaagt | ctggcacctc | agcctccctg | gccatcagtg | gctccagtc | tgaggatgag | 660 |
| gctgactatt | actgttcaac | atgggatgac | agcctgaatg | atcctgtggt | tttcggcgga | 720 |
| gggaccaagg | tcaccgtcct | aggt | | | | 744 |

<210> SEQ ID NO 10
<211> LENGTH: 744
<212> TYPE: DNA
<213> ORGANISM: Artificial Sequence
<220> FEATURE:
<223> OTHER INFORMATION: DNA encoding F002G03 scFv

<400> SEQUENCE: 10

| | | | | | |
|---|---|---|---|---|---|
| caggtgcagc | tggtgcagtc | tggggctgag | gtgaagaagc | ctgggtcctc | ggtgaaggtc | 60 |
| tcctgcaagg | cctctggagg | cacattcaac | agatatgcta | tcagttgggt | gcggcaggcc | 120 |

```
cctggacaag ggcttgagtg gatgggaggg atcatcccta tgtttgctac acctatctac    180
tcacagaagt tccaggacag agtcaccatt accgcggacg aatccacgag cacagcctac    240
atggagctga gcagcctgag atctgaggac acggccgtgt attactgtgc gagagaccga    300
acagattatt atgatactga tggttatcaa tcccccgact cctggggcaa gggcaccctg    360
gtcaccgtct cgagtggtgg aggcggttca ggcggaggtg gcagcggcgg cggcggatcg    420
gacatccaga tgacccagtc tccttccacc ctgtctgcat ctataggaga cagagtcacc    480
atcacttgcc gggccagtca gggcattaac aattatttag cctggtatca gcaaaaacca    540
gggagagccc ctaagctcct gatctacgct gcatccagtt tacaaagtgg ggtcccatca    600
aggttcagcg gcagtggatc tggcacagat ttcactctca ccatcagcag cctgcagcct    660
gaagattttg caacttatta ctgtctccaa gattccgatt atcccctcac tttcggcgga    720
gggaccaagc tggagatcaa acgt                                            744

<210> SEQ ID NO 11
<211> LENGTH: 747
<212> TYPE: DNA
<213> ORGANISM: Artificial Sequence
<220> FEATURE:
<223> OTHER INFORMATION: DNA encoding F003E11 scFv

<400> SEQUENCE: 11
caggtacagc tgcagcagtc aggggctgag gtgaagaagg ctgggtcctc ggtgaaggtc     60
tcctgcaagg cctctggaga cacccttcagc aactttgcta tcagctgggt gcgacaggcc   120
cctggacacg ggcttgagtg ggtgggaggg atcatccctg tcttcaacac ggctgactac   180
gcacagaatt tcacggacag agtcacgatt tccgcggaca aagccacgaa gacagtctac   240
atggaactgc acagcctgag atctgacgac acggccgtat atttctgtgc gaggacgaaa   300
atcgaactgg acaatgatgc ctttgatatc tggggccgag gcaccctggt caccgtctcg   360
agtggaggcg gcggttcagg cggaggtggc tctggcggtg gcggaagtgc acagtctgtg   420
ctgactcagc caccctcagc gtctgggacc cccgggcaga gggtcaccat ctcttgttct   480
ggaagcagct ccaacatcgg aagtaatact gtaaactggt atcagcagct cccaggaacg   540
gcccccaaac tcctcatcta tagtaataat cagcggccct caggggtccc tgaccgattc   600
tctggctcca agtctggcac ctcagcctcc ctggccatca gtgggctcca gtctgaggat   660
gaggctgatt attactgtgc agcatgggat gacagtctga atggcccctgt ggtattcggc   720 ggagggacca agctgaccgt cctaggt                                         747

<210> SEQ ID NO 12
<211> LENGTH: 747
<212> TYPE: DNA
<213> ORGANISM: Artificial Sequence
<220> FEATURE:
<223> OTHER INFORMATION: DNA encoding F003F09 scFv

<400> SEQUENCE: 12
gaggtgcagc tggtgcagtc tggggctgag gtgaggaagc ctgggtcctc ggtgaaggtc     60
tcctgcaagg cttctggaga cacccttcaac aactttgcta tcagctgggt gcgacaggcc   120
cctggacacg ggcttgagtg ggtgggaggg atcatccctg tcttcaacac ggctgactac   180
gcacagaatt tcacgggcag agtcacgatt tccgcggaca aagccacgaa gacagtctac   240
atggaactgc agcagcctgag atatgacgac acggccgtat atttctgtgc gaggacgaaa   300
```

| | |
|---|---|
| atcgaactgg acaatgatgc ctttgatatc tggggggcgag ggaccacggt caccgtctcg | 360 |
| agtggaggcg gcggttcagg cggaggtggc tctggcggtg gcggaagtgc actgcctgtg | 420 |
| ctgactcagc cccctcagc gtctgggacc ccgggcaga gggtcaccat ctcttgttct | 480 |
| ggaagcacct ccaacatcgg aagtaatgct gtagtttggt accagcagct cccaggagcg | 540 |
| gcccccaaac tcctcatcta tagtaatgat cagcggccct cagggtccc tgaccgattc | 600 |
| tctggctcca ggtctggcac ctcagcctcc ctggccatca gtggtctcca gtctgaggat | 660 |
| gaggctgatt attactgtgc agcatgggat gacagccggg atggtccttg gtgttcggc | 720 |
| ggagggacga aggtcaccgt cctaggt | 747 |

<210> SEQ ID NO 13
<211> LENGTH: 741
<212> TYPE: DNA
<213> ORGANISM: Artificial Sequence
<220> FEATURE:
<223> OTHER INFORMATION: DNA encoding F003G02 scFv

<400> SEQUENCE: 13

| | |
|---|---|
| caggtacagc tgcagcagtc aggggctgag gtgaagaagc ctgggtcctc ggtgaaggtc | 60 |
| tcctgcaagg cttctggagg caccttcagc agttatgcta tcagctgggt gcgacaggcc | 120 |
| cctggacaag gcttgagtg gatgggaggg atcatcccta cctttggtat agcagactac | 180 |
| gcacagaagt tccagggcag agtcacgatt accgcggacg aatccacgag cacagcctat | 240 |
| atggagctga ccggcctgag atctgaggac acggccatgt attactgtgc gaggggacag | 300 |
| ctggaacgac tgggcgaata tgactactgg ggcagaggga caatggtcac cgtctcgagt | 360 |
| ggaggcggcg gttcaggcgg aggtggctct ggcggtggcg aagtgcaca gtctgtgctg | 420 |
| actcagccac cctcagcgtc tgggaccccc gggcagaggg tcaccatctc ttgttctgga | 480 |
| agcagctcca acatcgaaat caatactgta aactggtata gcaactccc aggaacggcc | 540 |
| cccaaactcc tcatctatag tgattatcag cggccctcag gggtccctga ccgattctct | 600 |
| gcctccaagt ctggcacctc agcctccctg gccatcagtg gctccagtc tgaggatgag | 660 |
| gctgattatt actgtgcaac atgggatgac agcctgaatg gtccggtgtt cggcggaggg | 720 |
| accaaggtca ccgtcctagg t | 741 |

<210> SEQ ID NO 14
<211> LENGTH: 738
<212> TYPE: DNA
<213> ORGANISM: Artificial Sequence
<220> FEATURE:
<223> OTHER INFORMATION: DNA encoding F002C08 scFv

<400> SEQUENCE: 14

| | |
|---|---|
| gaggtgcagc tggtggagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaggg atcatcccta tctttggtac agcaaactac | 180 |
| gcacagaagt tccagggcag agtcacgatt accgcggacg aatccacgag cacagcctac | 240 |
| atggagctga gcagcctggg atctgaggac acggccgtgt attactgtgc gagagagtcg | 300 |
| ctaactggag attctgagct tgacctctgg ggcaaaggaa ccctggtcac cgtctcctca | 360 |
| ggtgaggcg gttcaggcgg aggtggcagc ggcggtggcg gatcgcagtc tgtgttgacg | 420 |
| cagccgccct cagtgtctgc ggccccagga cagaaggtca ccatttcctg ctctggaagc | 480 |
| acctccaaca ttgggaataa ttatgtctcc tggtaccaac agcacccagg caaagccccc | 540 |

```
aaactcatga tttatgatgt cagtaagcgg ccctcagggg tccctgaccg attctctggc    600
tccaagtctg gcaactcagc ctccctggac atcagtgggc tccagtctga ggatgaggct    660
gattattact gtgcagcatg ggatgacagc ctgagtgaat ttctcttcgg aactgggacc    720
aagctgaccg tcctaggt                                                  738
```

```
<210> SEQ ID NO 15
<211> LENGTH: 741
<212> TYPE: DNA
<213> ORGANISM: Artificial Sequence
<220> FEATURE:
<223> OTHER INFORMATION: DNA encoding F002E03 scFv

<400> SEQUENCE: 15
gaggtccagc tggtgcagtc cggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tgtttggtgc aggtaactac     180
gcaccgaagt tccaggacag agtcacgctt accgcggacg aatccacgag cactgcctac    240
atggagttga gcagcctgac atctgaggac acggccgtct atttctgtgc gagagactct    300
acggatttct ctggagatag tggactcgga atggacgtct ggggccgagg acaatggtc     360 accgtctcga gtggtggagg cggttccaggc ggaggtggca gcggcggtgg cggatcggac    420
atccagatga cccagtctcc atccttcctg tctgcatctg tagggacag agtcaccatc    480 acttgccggg ccagtcaggg cattaacaat tatttagcct ggtatcagca aaaaccaggg    540
agagccccta agctcctgat ctacgctgca tccagtttac aaagtggggt cccatcgagg    600
ttcagcggca gtggatctgg gacagatttc actctcacca tcagcagcct gcagcctgaa    660
gattttgcaa cttattactg tctccaagat tccgattatc ccctcacttt cggcggaggg    720
accaagctgg agatcaaacg t                                              741
```

```
<210> SEQ ID NO 16
<211> LENGTH: 741
<212> TYPE: DNA
<213> ORGANISM: Artificial Sequence
<220> FEATURE:
<223> OTHER INFORMATION: DNA encoding F002D02 scFv

<400> SEQUENCE: 16
gaggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagaggat    300
atagtgggtg cggttgatgg ttttgatatt tggggccggg aaccctggt caccgtctcg    360 agtggtggag gcggttcagg cggaggtggc agcggcggtg cggatcgca gtctgtgttg    420 acgcagccgc cctcagtgtc tgcggcccca ggacagaagg tcaccatttc ctgctctgga    480
agcacctcca acattgggaa taattatgtc tcctggtacc aacagcaccc aggcaaagcc    540
cccaaactca tgatttatga tgtcagtaag cggccctcag gggtccctga ccgattctct    600
ggctccaagt ctggcaactc agcctccctg gacatcagtg gctccagtc tgaggatgag    660 gctgattatt actgtgcagc atgggatgac agcctgagtg aatttctctt cggaactggg    720
```
accaagctga ccgtcctagg t                                        741

<210> SEQ ID NO 17
<211> LENGTH: 747
<212> TYPE: DNA
<213> ORGANISM: Artificial Sequence
<220> FEATURE:
<223> OTHER INFORMATION: DNA encoding F076D02 scFv

<400> SEQUENCE: 17
caggtgcagc tggtgcagtc tggggctgag gtgaggaagc ctgggtcctc ggtgaaggtc    60
tcctgcaagg cttctggaga caccttcaac aactttgcta tcagctgggt gcgacaggcc   120
cctggacacg ggcttgagtg gtgggaggg atcatccctg tcttcaacac ggctgactac    180
gcacagaatt tcacgggcag agtcacgatt ccgcggaca agccacgaa gacagtctac     240
atggaactgc gcagcctgag atatgacgac acggccgtat atttctgtgc gaggacgaaa   300
atcgaactgg acaatgatgc ctttgatatc tggggccaag gacaatggt caccgtctcg    360
agtggaggcg gcggttcagg cggaggtggc tctggcggtg gcggaagtgc acagtctgtg   420
ctgactcagc caccctcagc gtctgggacc ccgggcaga gggtcaccat ctcttgttct    480
ggaaccacct ccaatatcgg aagtaatagt gtaagctggt accagaagct cccaggaacg   540
gccccaaac tcctcatcca tagtaataat ctgcggccct caggagtccc tgaccgattc     600
tctggctcca gtctggcac tcagcctcc ctggccatca gtgggctccg gtctgaggat     660
gaggctgatt attactgtgc agcgtgggat gacagcctga gtggccctgt ggtcttcggc    720
ggagggacca aggtcaccgt cctaggt                                       747

<210> SEQ ID NO 18
<211> LENGTH: 756
<212> TYPE: DNA
<213> ORGANISM: Artificial Sequence
<220> FEATURE:
<223> OTHER INFORMATION: DNA encoding F075G06 scFv

<400> SEQUENCE: 18
gaagtgcagc tggtgcagtc tgggcctgag gtgaagaagc ctgggtcctc ggtgaaggtc    60
tcctgcaggg cttctggagg caccttcagc acctatgctt tcagctgggt gcgacaggcc   120
cctggacagg ggcttgagtg gatgggagga atcatccctg tgtttgaaac accgatctac    180
gcacagaagt tacagggcag actcacgatt accgcggaca catcgacgga cacggcctac    240
atggaactga gcaacctgag atctggggac acggccgttt attactgtgc gagagagtgg    300
ggggactatt acagttcagt cagttctgga gctctgcact actggggcca aggcaccctg    360
gtcaccgtct cgagtggagg cggcggttca ggcggaggtg gctctggcgg tggcggaagt    420
gcacagtctg tcgtgacgca gccgccctca gcgtctggga ccccgggca gagggtcacc     480
atctcttgtt ctgaagcag gtccaacatc ggaagtaata ttgtaaactg gtaccagcag    540
cttgtaggaa cggccccaa actcctcatt tatagtgata atcagcggcc ctcaggggtc    600
cccgaccgat tctctggctc caagtctggc acctcagcct ccctggccat cagtgggctc    660
cagtctgagg atgaggctga ttattactgt gcagcatggg atgacagcct caatcgttat    720
gtcttcggaa ctgggaccaa ggtcaccgtc ctaggt                            756

<210> SEQ ID NO 19
<211> LENGTH: 747
<212> TYPE: DNA
<213> ORGANISM: Artificial Sequence
<220> FEATURE:
<223> OTHER INFORMATION: DNA encoding F076G06 scFv

<400> SEQUENCE: 19

| | | |
|---|---|---|
| cagatgcagc tggtgcagtc tggggctgag gtgaggaagc ctgggtcctc ggtgaaggtc | 60 |
| tcctgcaagg cttctggaga caccttcaac aactttgcta tcagctgggt gcgacaggcc | 120 |
| cctggacacg gcttgagtg gtgggaggg atcatccctg tcttcaacac ggctgactac | 180 |
| gcacagaatt tcacgggcag agtcacgatt ccgcggaca aagccacgaa gacagtctac | 240 |
| atggaactgc gcagcctgag atatgacgac acggccgtat atttctgtgc gaggacgaaa | 300 |
| atcgaactgg acaatgatgc ctttgatatc tggggccaag ggacaatggt caccgtctcg | 360 |
| agtggaggcg gcggttcagg cggaggtggc tctggcggtg gcggaagtgc acagtctgtg | 420 |
| ctgacgcagc cgccctcagc gtctgggacc cccgggcaga gggtcaccat ctcttgttct | 480 |
| ggaagcagct ccaatatcgg aagtaatact gtaaactggt accagcacct cccaggaacg | 540 |
| gcccccaaac tcctcatcta tagtaataat cagcggccct caggggtccc tgaccgattc | 600 |
| tctggctcca gtctggcac ctcagcctcc ctggccatca gtgggctcca gtctgaggat | 660 |
| gaggctgatt attactgtgc agcatgggat gacagcctga tggtccttta tgtcttcgga | 720 |
| actgggacca agctgaccgt cctaggt | 747 |

<210> SEQ ID NO 20
<211> LENGTH: 250
<212> TYPE: PRT
<213> ORGANISM: Artificial sequence
<220> FEATURE:
<223> OTHER INFORMATION: F003A09 scFv

<400> SEQUENCE: 20

Gln Val Gln Leu Val Gln Ser Gly Ala Glu Val Lys Lys Ala Gly Ser
1               5                   10                  15

Ser Val Lys Val Ser Cys Lys Ala Ser Gly Asp Thr Phe Ser Asn Phe
                20                  25                  30

Ala Ile Ser Trp Val Arg Gln Ala Pro Gly His Gly Leu Glu Trp Val
            35                  40                  45

Gly Gly Ile Ile Pro Val Phe Asn Thr Ala Asp Tyr Ala Gln Asn Phe
        50                  55                  60

Thr Asp Arg Val Thr Ile Ser Ala Asp Lys Ala Thr Lys Thr Val Tyr
65                  70                  75                  80

Met Glu Leu Arg Ser Leu Arg Ser Asp Asp Thr Ala Val Tyr Phe Cys
                85                  90                  95

Ala Arg Thr Lys Ile Glu Leu Asp Asn Asp Ala Phe Asp Ile Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Ala Gln Pro Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Ser Asn Ile Gly Ser Asn Thr Val Asn Trp Tyr Gln Gln
                165                 170                 175

Leu Pro Gly Thr Ala Pro Lys Leu Leu Ile Tyr Ser Asn Asn Gln Arg
            180                 185                 190

Pro Ser Gly Val Pro Asp Arg Phe Ser Gly Ser Lys Ser Gly Thr Ser
        195                 200                 205

```
Ala Ser Leu Ala Ile Ser Gly Leu Gln Ser Glu Asp Glu Ala Asp Tyr
    210                 215                 220

Tyr Cys Ala Ala Trp Asp Asp Ser Leu Asn Gly Pro Phe Trp Val Phe
225                 230                 235                 240

Gly Gly Gly Thr Lys Leu Thr Val Leu Gly
            245                 250
```

<210> SEQ ID NO 21
<211> LENGTH: 245
<212> TYPE: PRT
<213> ORGANISM: Artificial sequence
<220> FEATURE:
<223> OTHER INFORMATION: F081C09 scFv

<400> SEQUENCE: 21

```
Gln Val Gln Leu Val Gln Ser Gly Ala Glu Val Lys Lys Pro Gly Ser
1               5                   10                  15

Ser Val Arg Val Ser Cys Lys Ala Ser Gly Gly Ser Phe Ser Asp Tyr
                20                  25                  30

Ala Ile His Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gln Tyr Asp Asp Ala Phe Asp Ile Trp Gly Gln Arg
            100                 105                 110

Thr Met Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
130                 135                 140

Ser Ala Ala Pro Gly Gln Lys Val Thr Ile Ser Cys Ser Gly Ser Thr
145                 150                 155                 160

Ser Asn Ile Gly Asn Asn Tyr Val Ser Trp Tyr Gln Gln His Pro Gly
                165                 170                 175

Lys Ala Pro Lys Leu Met Ile Tyr Asp Val Ser Lys Arg Pro Ser Gly
            180                 185                 190

Val Pro Asp Arg Phe Ser Gly Ser Lys Ser Gly Asn Ser Ala Ser Leu
        195                 200                 205

Asp Ile Ser Gly Leu Gln Ser Glu Asp Glu Ala Asp Tyr Tyr Cys Ala
    210                 215                 220

Ala Trp Asp Asp Ser Leu Ser Glu Phe Leu Phe Gly Thr Gly Thr Lys
225                 230                 235                 240

Leu Thr Val Leu Gly
            245
```

<210> SEQ ID NO 22
<211> LENGTH: 250
<212> TYPE: PRT
<213> ORGANISM: Artificial sequence
<220> FEATURE:
<223> OTHER INFORMATION: F076F10 scFv

<400> SEQUENCE: 22

```
Glu Val Gln Leu Val Gln Ser Gly Ala Glu Val Lys Lys Pro Gly Ser
```

```
            1               5                  10                 15
Ser Val Lys Val Phe Cys Lys Thr Ser Gly Gly Thr Phe Ser Ser Tyr
                20                 25                 30

Ala Phe Gly Trp Val Arg Gln Arg Pro Gly Gln Gly Leu Glu Trp Met
            35                 40                 45

Gly Gly Ile Ile Pro Asn Phe Asp Ala Ala Asn Tyr Ala Gln Lys Phe
        50                 55                 60

Gln Asp Thr Val Ala Phe Thr Ala Asp Thr Ser Thr Asn Thr Leu Tyr
65                 70                 75                 80

Leu Glu Leu Ser Ser Leu Thr Ser Asp Asp Thr Ala Val Tyr Tyr Cys
                85                 90                 95

Ala Arg Glu Val Gly Val His Ala Ser Gly Leu Gly Ala Phe Asp Ile
            100                105                110

Trp Gly Arg Gly Thr Leu Val Thr Val Ser Ser Gly Gly Gly Gly Ser
        115                120                125

Gly Gly Gly Gly Ser Gly Gly Gly Ser Ala Gln Ser Val Leu Thr
        130                135                140

Gln Pro Pro Ser Val Ser Gly Ala Pro Arg Gln Arg Val Thr Ile Ser
145                150                155                160

Cys Ser Gly Ser Ser Asn Ile Gly Asp Asn Val Val Asn Trp Tyr
            165                170                175

Gln Gln Leu Pro Gly Lys Ala Pro Lys Leu Leu Ile Tyr Tyr Asp Asp
            180                185                190

Leu Leu Pro Ser Gly Val Ser Asp Arg Phe Ser Gly Ser Lys Ser Gly
            195                200                205

Thr Ser Ala Ser Leu Ala Ile Ser Gly Leu Gln Ser Glu Asp Glu Ala
        210                215                220

Asp Tyr Phe Cys Ala Ala Trp Asp Asp Ser Leu Asp Ala Tyr Val Phe
225                230                235                240

Gly Thr Arg Thr Lys Val Thr Val Leu Gly
            245                250

<210> SEQ ID NO 23
<211> LENGTH: 245
<212> TYPE: PRT
<213> ORGANISM: Artificial sequence
<220> FEATURE:
<223> OTHER INFORMATION: F002D07 scFv

<400> SEQUENCE: 23

Gln Val Gln Leu Val Gln Ser Gly Gly Gly Val Val Gln Pro Gly Arg
1               5                  10                 15

Ser Leu Arg Leu Ser Cys Ala Ala Ser Gly Phe Ile Phe Ser Ser Tyr
                20                 25                 30

Gly Met His Trp Val Arg Gln Ala Pro Gly Lys Gly Leu Glu Trp Val
            35                 40                 45

Ala Gly Ile Phe Tyr Asp Gly Gly Asn Lys Tyr Tyr Ala Asp Ser Val
        50                 55                 60

Lys Gly Arg Phe Thr Ile Ser Arg Asp Asn Lys Asn Thr Leu Tyr
65                 70                 75                 80

Leu Gln Met Asn Ser Leu Arg Ala Glu Asp Thr Ala Val Tyr Tyr Cys
                85                 90                 95

Ala Arg Asp Arg Gly Tyr Tyr Tyr Met Asp Val Trp Gly Lys Gly Thr
            100                105                110

Thr Val Thr Val Ser Ser Gly Gly Gly Gly Ser Gly Gly Gly Gly Ser
```

```
              115                 120                 125
Gly Gly Gly Gly Ser Gln Ser Val Leu Thr Gln Pro Ser Val Ser
            130                 135                 140
Gly Ala Pro Gly Gln Arg Val Thr Ile Ser Cys Thr Gly Arg Ser Ser
145                 150                 155                 160
Asn Ile Gly Ala Gly His Asp Val His Trp Tyr Gln Gln Leu Pro Gly
                165                 170                 175
Thr Ala Pro Lys Leu Leu Ile Tyr Gly Asp Ser Asn Arg Pro Ser Gly
            180                 185                 190
Val Pro Asp Arg Phe Ser Gly Ser Arg Ser Gly Thr Ser Ala Ser Leu
            195                 200                 205
Ala Ile Thr Gly Leu Gln Ala Glu Asp Glu Ala Asp Tyr Tyr Cys Gln
            210                 215                 220
Ser Tyr Asp Ser Ser Leu Arg Gly Ser Val Phe Gly Gly Gly Thr Lys
225                 230                 235                 240
Val Thr Val Leu Gly
            245

<210> SEQ ID NO 24
<211> LENGTH: 252
<212> TYPE: PRT
<213> ORGANISM: Artificial sequence
<220> FEATURE:
<223> OTHER INFORMATION: F076C06 scFv

<400> SEQUENCE: 24

Gln Val Gln Leu Val Gln Ser Gly Pro Glu Val Lys Lys Pro Gly Ser
1               5                   10                  15
Ser Val Lys Val Ser Cys Arg Ala Ser Gly Gly Thr Phe Ser Thr Tyr
            20                  25                  30
Ala Phe Ser Trp Val Arg Gln Ala Pro Gly Gln Gly Leu Glu Trp Met
        35                  40                  45
Gly Gly Ile Ile Pro Val Phe Glu Thr Pro Ile Tyr Ala Gln Lys Leu
    50                  55                  60
Gln Gly Arg Leu Thr Ile Thr Ala Asp Thr Ser Thr Asp Thr Ala Tyr
65                  70                  75                  80
Met Glu Leu Ser Asn Leu Arg Ser Gly Asp Thr Ala Val Tyr Tyr Cys
                85                  90                  95
Ala Arg Glu Trp Gly Asp Tyr Tyr Ser Ser Val Ser Ser Gly Ala Leu
            100                 105                 110
His Tyr Trp Gly Arg Gly Thr Leu Val Thr Val Ser Ser Gly Gly Gly
        115                 120                 125
Gly Ser Gly Gly Gly Gly Ser Gly Gly Gly Gly Ser Ala Gln Ala Val
            130                 135                 140
Leu Thr Gln Pro Ser Ser Ala Ser Gly Thr Pro Gly Gln Arg Val Thr
145                 150                 155                 160
Ile Ser Cys Ser Gly Ser Ser Ser Asn Ile Gly Asn Asn Ala Val Asn
                165                 170                 175
Trp Tyr Gln Gln Leu Pro Gly Thr Ala Pro Lys Leu Leu Ile Tyr Asn
            180                 185                 190
Asn Asn Gln Trp Pro Ser Gly Val Pro Asp Arg Phe Ser Gly Ser Lys
            195                 200                 205
Ser Gly Thr Ser Ala Ser Leu Ala Val Ser Gly Leu Gln Ser Glu Asp
            210                 215                 220
Glu Ala Asp Tyr Tyr Cys Ala Ala Trp Asp Asp Ser Leu Asn Gly Tyr
```

```
                    225                 230                 235                 240

Val Phe Gly Thr Gly Thr Gln Leu Thr Val Leu Ser
                245                 250

<210> SEQ ID NO 25
<211> LENGTH: 253
<212> TYPE: PRT
<213> ORGANISM: Artificial sequence
<220> FEATURE:
<223> OTHER INFORMATION: F003B07 scFv

<400> SEQUENCE: 25

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asp Ser Tyr
            20                  25                  30

Ala Phe Ser Trp Val Arg Gln Ala Pro Gly Gln Gly Leu Glu Trp Met
        35                  40                  45

Gly Gly Ile Ile Pro Met Phe Asp Thr Pro Ile Tyr Ala Gln Lys Phe
    50                  55                  60

Gln Gly Lys Val Thr Ile Thr Ala Asp Thr Ser Thr Ser Thr Val Tyr
65                  70                  75                  80

Met Lys Leu Ser Ser Leu Arg Ser Gly Asp Thr Ala Ile Tyr Tyr Cys
                85                  90                  95

Ala Arg Glu Trp Gly Gly Tyr Tyr Ser Ser Glu Ser Ser Gly Ala Leu
            100                 105                 110

Gln Tyr Trp Gly Arg Gly Thr Leu Val Thr Val Ser Ser Gly Gly Gly
        115                 120                 125

Gly Ser Gly Gly Gly Gly Ser Gly Gly Gly Gly Ser Ala Gln Ala Val
    130                 135                 140

Leu Thr Gln Pro Ser Ser Val Ser Gly Ala Pro Gly Gln Arg Val Thr
145                 150                 155                 160

Ile Ser Cys Thr Gly Ser Arg Ser Asn Ile Gly Ala Asp Tyr Asp Val
                165                 170                 175

Gln Trp Tyr Gln Gln Leu Pro Gly Thr Ala Pro Lys Leu Leu Ile Tyr
            180                 185                 190

Gly Asn Asn Asn Arg Pro Ser Gly Val Pro Asp Arg Phe Ser Gly Ser
        195                 200                 205

Lys Ser Asp Arg Ser Ala Ser Leu Ala Ile Thr Gly Leu Arg Ala Glu
    210                 215                 220

Asp Glu Ser Asp Tyr Tyr Cys Gln Ser Tyr Asp Ser Ser Leu Ser Val
225                 230                 235                 240

Trp Val Phe Gly Gly Gly Thr Lys Leu Thr Val Leu Gly
                245                 250

<210> SEQ ID NO 26
<211> LENGTH: 248
<212> TYPE: PRT
<213> ORGANISM: Artificial sequence
<220> FEATURE:
<223> OTHER INFORMATION: F003F01 scFv

<400> SEQUENCE: 26

Glu Val Gln Leu Val Gln Ser Gly Ala Glu Val Arg Lys Pro Ala Ser
1               5                   10                  15

Ser Val Lys Val Ser Cys Lys Thr Ser Gly Gly Ser Phe Asn Asp Tyr
            20                  25                  30
```

```
Ser Phe Asn Trp Val Arg Gln Ala Pro Gly Gln Gly Leu Glu Trp Met
        35                  40                  45

Gly Ser Ile Ile Pro Val Phe Asp Met Ala Asp Tyr Gly Gln Asn Phe
 50                  55                  60

Gln Gly Arg Leu Thr Ile Thr Ala Asp Glu Ser Thr Thr Thr Ala Tyr
65                  70                  75                  80

Met Glu Leu Ser Asp Leu Thr Pro Met Asp Thr Ala Ile Tyr Tyr Cys
                85                  90                  95

Ala Arg Val Ala Met Val Gly Ala Thr His Phe Asp Ile Trp Gly Gln
            100                 105                 110

Gly Thr Leu Val Thr Val Ser Gly Gly Gly Ser Gly Gly Gly
            115                 120                 125

Gly Ser Gly Gly Gly Ser Ala Gln Ser Val Leu Thr Gln Pro Pro
            130                 135                 140

Ser Ala Ser Gly Thr Pro Gly Gln Arg Val Thr Ile Ser Cys Ser Gly
145                 150                 155                 160

Gly Ser Ser Asn Ile Gly Ser Asn Pro Val Asn Trp Tyr Gln Gln Val
                165                 170                 175

Pro Gly Thr Ala Pro Lys Leu Leu Ile Tyr Leu Ser Asp Gln Arg Pro
            180                 185                 190

Ala Gly Val Pro Asp Arg Phe Ser Gly Ser Lys Ser Gly Thr Ser Ala
            195                 200                 205

Ser Leu Ala Ile Ser Gly Leu Gln Ser Glu Asp Glu Ala Asp Tyr Tyr
    210                 215                 220

Cys Ser Thr Trp Asp Asp Ser Leu Asn Asp Pro Val Val Phe Gly Gly
225                 230                 235                 240

Gly Thr Lys Val Thr Val Leu Gly
                245

<210> SEQ ID NO 27
<211> LENGTH: 248
<212> TYPE: PRT
<213> ORGANISM: Artificial sequence
<220> FEATURE:
<223> OTHER INFORMATION: F002G03 scFv

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Ala Thr Pro Ile Tyr Ser Gln Lys Phe
 50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Asp Tyr Tyr Asp Thr Asp Gly Tyr Gln Ser Pro
            100                 105                 110

Asp Ser Trp Gly Lys Gly Thr Leu Val Thr Val Ser Ser Gly Gly Gly
            115                 120                 125

Gly Pro Gly Gly Gly Ser Gly Gly Gly Ser Asp Ile Gln Met
130                 135                 140
```

```
Thr Gln Ser Pro Ser Thr Leu Ser Ala Ser Ile Gly Asp Arg Val Thr
145                 150                 155                 160

Ile Thr Cys Arg Ala Ser Gln Gly Ile Asn Asn Tyr Leu Ala Trp Tyr
                165                 170                 175

Gln Gln Lys Pro Gly Arg Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Leu Gln Asp Ser Asp Tyr Pro Leu Thr Phe Gly Gly
225                 230                 235                 240

Gly Thr Lys Leu Glu Ile Lys Arg
                245

<210> SEQ ID NO 28
<211> LENGTH: 249
<212> TYPE: PRT
<213> ORGANISM: Artificial sequence
<220> FEATURE:
<223> OTHER INFORMATION: F003E11 scFv

<400> SEQUENCE: 28

Gln Val Gln Leu Gln Gln Ser Gly Ala Glu Val Lys Lys Ala Gly Ser
1               5                   10                  15

Ser Val Lys Val Ser Cys Lys Ala Ser Gly Asp Thr Phe Ser Asn Phe
                20                  25                  30

Ala Ile Ser Trp Val Arg Gln Ala Pro Gly His Gly Leu Glu Trp Val
            35                  40                  45

Gly Gly Ile Ile Pro Val Phe Asn Thr Ala Asp Tyr Ala Gln Asn Phe
        50                  55                  60

Thr Asp Arg Val Thr Ile Ser Ala Asp Lys Ala Thr Lys Thr Val Tyr
65                  70                  75                  80

Met Glu Leu His Ser Leu Arg Ser Asp Thr Ala Val Tyr Phe Cys
                85                  90                  95

Ala Arg Thr Lys Ile Glu Leu Asp Asn Asp Ala Phe Asp Ile Trp Gly
                100                 105                 110

Arg Gly Thr Leu Val Thr Val Ser Ser Gly Gly Gly Ser Gly Gly
            115                 120                 125

Gly Gly Ser Gly Gly Gly Ser Ala Gln Ser Val Leu Thr Gln Pro
        130                 135                 140

Pro Ser Ala Ser Gly Thr Pro Gly Gln Arg Val Thr Ile Ser Cys Ser
145                 150                 155                 160

Gly Ser Ser Ser Asn Ile Gly Ser Asn Thr Val Asn Trp Tyr Gln Gln
                165                 170                 175

Leu Pro Gly Thr Ala Pro Lys Leu Leu Ile Tyr Ser Asn Asn Gln Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Gln Ser Glu Asp Glu Ala Asp Tyr
    210                 215                 220

Tyr Cys Ala Ala Trp Asp Asp Ser Leu Asn Gly Pro Val Val Phe Gly
225                 230                 235                 240

Gly Gly Thr Lys Leu Thr Val Leu Gly
                245
```

```
<210> SEQ ID NO 29
<211> LENGTH: 250
<212> TYPE: PRT
<213> ORGANISM: Artificial sequence
<220> FEATURE:
<223> OTHER INFORMATION: F003F09 scFv

<400> SEQUENCE: 29

Glu Val Gln Leu Val Gln Ser Gly Ala Glu Val Arg Lys Pro Gly Ser
1               5                   10                  15

Ser Val Lys Val Ser Cys Lys Ala Ser Gly Asp Thr Phe Asn Asn Phe
            20                  25                  30

Ala Ile Ser Trp Val Arg Gln Ala Pro Gly His Gly Leu Glu Trp Val
        35                  40                  45

Gly Gly Ile Ile Pro Val Phe Asn Thr Ala Asp Tyr Ala Gln Asn Phe
    50                  55                  60

Thr Gly Arg Val Thr Ile Ser Ala Asp Lys Ala Thr Lys Thr Val Tyr
65                  70                  75                  80

Met Glu Leu Arg Ser Leu Arg Tyr Asp Asp Thr Ala Val Tyr Phe Cys
                85                  90                  95

Ala Arg Thr Lys Ile Glu Leu Asp Asn Asp Ala Phe Asp Ile Trp Gly
            100                 105                 110

Arg Gly Thr Thr Val Thr Val Ser Ser Gly Gly Gly Gly Ser Gly
        115                 120                 125

Gly Gly Gly Ser Gly Gly Gly Ser Ala Leu Pro Val Leu Thr Gln
    130                 135                 140

Pro Pro Ser Ala Ser Gly Thr Pro Gly Gln Arg Val Thr Ile Ser Cys
145                 150                 155                 160

Ser Gly Ser Thr Ser Asn Ile Gly Ser Asn Ala Val Val Trp Tyr Gln
                165                 170                 175

Gln Leu Pro Gly Ala Ala Pro Lys Leu Leu Ile Tyr Ser Asn Asp Gln
            180                 185                 190

Arg Pro Ser Gly Val Pro Asp Arg Phe Ser Gly Ser Arg Ser Gly Thr
        195                 200                 205

Ser Ala Ser Leu Ala Ile Ser Gly Leu Gln Ser Glu Asp Glu Ala Asp
    210                 215                 220

Tyr Tyr Cys Ala Ala Trp Asp Asp Ser Arg Asp Gly Pro Trp Val Phe
225                 230                 235                 240

Gly Gly Gly Thr Lys Val Thr Val Leu Gly
                245                 250

<210> SEQ ID NO 30
<211> LENGTH: 247
<212> TYPE: PRT
<213> ORGANISM: Artificial sequence
<220> FEATURE:
<223> OTHER INFORMATION: F003G02 scFv

<400> SEQUENCE: 30

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Thr Phe Gly Ile Ala Asp Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Thr Gly Leu Arg Ser Glu Asp Thr Ala Met Tyr Tyr Cys
                 85                  90                  95

Ala Arg Gly Gln Leu Glu Arg Leu Gly Tyr Asp Tyr Trp Gly Arg
            100                 105                 110

Gly Thr Met Val Thr Val Ser Gly Gly Gly Ser Gly Gly Gly
            115                 120                 125

Gly Ser Gly Gly Gly Ser Ala Gln Ser Val Leu Thr Gln Pro Pro
        130                 135                 140

Ser Ala Ser Gly Thr Pro Gly Gln Arg Val Thr Ile Ser Cys Ser Gly
145                 150                 155                 160

Ser Ser Ser Asn Ile Glu Ile Asn Thr Val Asn Trp Tyr Lys Gln Leu
                165                 170                 175

Pro Gly Thr Ala Pro Lys Leu Leu Ile Tyr Ser Asp Tyr Gln Arg Pro
            180                 185                 190

Ser Gly Val Pro Asp Arg Phe Ser Ala Ser Lys Ser Gly Thr Ser Ala
            195                 200                 205

Ser Leu Ala Ile Ser Gly Leu Gln Ser Glu Asp Glu Ala Asp Tyr Tyr
    210                 215                 220

Cys Ala Thr Trp Asp Asp Ser Leu Asn Gly Pro Val Phe Gly Gly Gly
225                 230                 235                 240

Thr Lys Val Thr Val Leu Gly
                245

<210> SEQ ID NO 31
<211> LENGTH: 246
<212> TYPE: PRT
<213> ORGANISM: Artificial sequence
<220> FEATURE:
<223> OTHER INFORMATION: F002C08 scFv

<400> SEQUENCE: 31

Glu Val Gln Leu Val Glu Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Gly Ser Glu Asp Thr Ala Val Tyr Tyr Cys
                 85                  90                  95

Ala Arg Glu Ser Leu Thr Gly Asp Ser Glu Leu Asp Leu Trp Gly Lys
            100                 105                 110

Gly Thr Leu Val Thr Val Ser Ser Gly Gly Gly Ser Gly Gly Gly
            115                 120                 125

Gly Ser Gly Gly Gly Gly Ser Gln Ser Val Leu Thr Gln Pro Pro Ser
        130                 135                 140

Val Ser Ala Ala Pro Gly Gln Lys Val Thr Ile Ser Cys Ser Gly Ser
145                 150                 155                 160

Thr Ser Asn Ile Gly Asn Asn Tyr Val Ser Trp Tyr Gln Gln His Pro
                165                 170                 175
```

-continued

Gly Lys Ala Pro Lys Leu Met Ile Tyr Asp Val Ser Lys Arg Pro Ser
            180                 185                 190

Gly Val Pro Asp Arg Phe Ser Gly Ser Lys Ser Gly Asn Ser Ala Ser
            195                 200                 205

Leu Asp Ile Ser Gly Leu Gln Ser Glu Asp Glu Ala Asp Tyr Tyr Cys
            210                 215                 220

Ala Ala Trp Asp Asp Ser Leu Ser Glu Phe Leu Phe Gly Thr Gly Thr
225                 230                 235                 240

Lys Leu Thr Val Leu Gly
                245

<210> SEQ ID NO 32
<211> LENGTH: 247
<212> TYPE: PRT
<213> ORGANISM: Artificial sequence
<220> FEATURE:
<223> OTHER INFORMATION: F002E03 scFv

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Met Phe Gly Ala Gly Asn Tyr Ala Pro Lys Phe
        50                  55                  60

Gln Asp Arg Val Thr Leu Thr Ala Asp Glu Ser Thr Ser Thr Ala Tyr
65                  70                  75                  80

Met Glu Leu Ser Ser Leu Thr Ser Glu Asp Thr Ala Val Tyr Phe Cys
                85                  90                  95

Ala Arg Asp Ser Thr Asp Phe Ser Asp Ser Gly Leu Gly Met Asp
            100                 105                 110

Val Trp Gly Arg Gly Thr Met Val Thr Val Ser Ser Gly Gly Gly Gly
        115                 120                 125

Pro Gly Gly Gly Ser Gly Gly Gly Ser Asp Ile Gln Met Thr
    130                 135                 140

Gln Ser Pro Ser Phe Leu Ser Ala Ser Val Gly Asp Arg Val Thr Ile
145                 150                 155                 160

Thr Cys Arg Ala Ser Gln Gly Ile Asn Asn Tyr Leu Ala Trp Tyr Gln
                165                 170                 175

Gln Lys Pro Gly Arg Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
            210                 215                 220

Tyr Tyr Cys Leu Gln Asp Ser Asp Tyr Pro Leu Thr Phe Gly Gly Gly
225                 230                 235                 240

Thr Lys Leu Glu Ile Lys Arg
                245

<210> SEQ ID NO 33
<211> LENGTH: 247
<212> TYPE: PRT
<213> ORGANISM: Artificial sequence

```
<220> FEATURE:
<223> OTHER INFORMATION: F002D02 scFv

<400> SEQUENCE: 33

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Ile Val Gly Ala Val Asp Gly Phe Asp Ile Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Val Ser Ala Ala Pro Gly Gln Lys Val Thr Ile Ser Cys Ser Gly
145                 150                 155                 160

Ser Thr Ser Asn Ile Gly Asn Asn Tyr Val Ser Trp Tyr Gln Gln His
                165                 170                 175

Pro Gly Lys Ala Pro Lys Leu Met Ile Tyr Asp Val Ser Lys Arg Pro
            180                 185                 190

Ser Gly Val Pro Asp Arg Phe Ser Gly Ser Lys Ser Gly Asn Ser Ala
        195                 200                 205

Ser Leu Asp Ile Ser Gly Leu Gln Ser Glu Asp Glu Ala Asp Tyr Tyr
    210                 215                 220

Cys Ala Ala Trp Asp Asp Ser Leu Ser Glu Phe Leu Phe Gly Thr Gly
225                 230                 235                 240

Thr Lys Leu Thr Val Leu Gly
                245

<210> SEQ ID NO 34
<211> LENGTH: 249
<212> TYPE: PRT
<213> ORGANISM: Artificial sequence
<220> FEATURE:
<223> OTHER INFORMATION: F076D02 scFv

<400> SEQUENCE: 34

Gln Val Gln Leu Val Gln Ser Gly Ala Glu Val Arg Lys Pro Gly Ser
1               5                   10                  15

Ser Val Lys Val Ser Cys Lys Ala Ser Gly Asp Thr Phe Asn Asn Phe
            20                  25                  30

Ala Ile Ser Trp Val Arg Gln Ala Pro Gly His Gly Leu Glu Trp Val
        35                  40                  45

Gly Gly Ile Ile Pro Val Phe Asn Thr Ala Asp Tyr Ala Gln Asn Phe
    50                  55                  60

Thr Gly Arg Val Thr Ile Ser Ala Asp Lys Ala Thr Lys Thr Val Tyr
65                  70                  75                  80

Met Glu Leu Arg Ser Leu Arg Tyr Asp Asp Thr Ala Val Tyr Phe Cys
```

```
                85                  90                  95
Ala Arg Thr Lys Ile Glu Leu Asp Asn Asp Ala Phe Asp Ile Trp Gly
            100                 105                 110
Gln Gly Thr Met Val Thr Val Ser Ser Gly Gly Gly Ser Gly Gly
            115                 120                 125
Gly Gly Ser Gly Gly Gly Ser Ala Gln Ser Val Leu Thr Gln Pro
            130                 135                 140
Pro Ser Ala Ser Gly Thr Pro Gly Gln Arg Val Thr Ile Ser Cys Ser
145                 150                 155                 160
Gly Thr Thr Ser Asn Ile Gly Ser Asn Ser Val Ser Trp Tyr Gln Lys
                165                 170                 175
Leu Pro Gly Thr Ala Pro Lys Leu Leu Ile His Ser Asn Asn Leu Arg
            180                 185                 190
Pro Ser Gly Val Pro Asp Arg Phe Ser Gly Ser Lys Ser Gly Thr Ser
            195                 200                 205
Ala Ser Leu Ala Ile Ser Gly Leu Arg Ser Glu Asp Glu Ala Asp Tyr
            210                 215                 220
Tyr Cys Ala Ala Trp Asp Asp Ser Leu Ser Gly Pro Val Val Phe Gly
225                 230                 235                 240
Gly Gly Thr Lys Val Thr Val Leu Gly
                245

<210> SEQ ID NO 35
<211> LENGTH: 252
<212> TYPE: PRT
<213> ORGANISM: Artificial sequence
<220> FEATURE:
<223> OTHER INFORMATION: F075G06 scFv

<400> SEQUENCE: 35

Glu Val Gln Leu Val Gln Ser Gly Pro Glu Val Lys Lys Pro Gly Ser
1               5                   10                  15
Ser Val Lys Val Ser Cys Arg Ala Ser Gly Gly Thr Phe Ser Thr Tyr
            20                  25                  30
Ala Phe Ser Trp Val Arg Gln Ala Pro Gly Gln Gly Leu Glu Trp Met
            35                  40                  45
Gly Gly Ile Ile Pro Val Phe Glu Thr Pro Ile Tyr Ala Gln Lys Leu
        50                  55                  60
Gln Gly Arg Leu Thr Ile Thr Ala Asp Thr Ser Thr Asp Thr Ala Tyr
65                  70                  75                  80
Met Glu Leu Ser Asn Leu Arg Ser Gly Asp Thr Ala Val Tyr Tyr Cys
                85                  90                  95
Ala Arg Glu Trp Gly Asp Tyr Tyr Ser Ser Val Ser Ser Gly Ala Leu
            100                 105                 110
His Tyr Trp Gly Gln Gly Thr Leu Val Thr Val Ser Ser Gly Gly Gly
            115                 120                 125
Gly Ser Gly Gly Gly Gly Ser Gly Gly Gly Gly Ser Ala Gln Ser Val
        130                 135                 140
Val Thr Gln Pro Pro Ser Ala Ser Gly Thr Pro Gly Gln Arg Val Thr
145                 150                 155                 160
Ile Ser Cys Ser Gly Ser Arg Ser Asn Ile Gly Ser Asn Ile Val Asn
                165                 170                 175
Trp Tyr Gln Gln Leu Val Gly Thr Ala Pro Lys Leu Leu Ile Tyr Ser
            180                 185                 190
Asp Asn Gln Arg Pro Ser Gly Val Pro Asp Arg Phe Ser Gly Ser Lys
```

```
                195                 200                 205
Ser Gly Thr Ser Ala Ser Leu Ala Ile Ser Gly Leu Gln Ser Glu Asp
    210                 215                 220

Glu Ala Asp Tyr Tyr Cys Ala Ala Trp Asp Asp Ser Leu Asn Arg Tyr
225                 230                 235                 240

Val Phe Gly Thr Gly Thr Lys Val Thr Val Leu Gly
                245                 250

<210> SEQ ID NO 36
<211> LENGTH: 249
<212> TYPE: PRT
<213> ORGANISM: Artificial sequence
<220> FEATURE:
<223> OTHER INFORMATION: F076G06 scFv

<400> SEQUENCE: 36

Gln Met Gln Leu Val Gln Ser Gly Ala Glu Val Arg Lys Pro Gly Ser
1               5                   10                  15

Ser Val Lys Val Ser Cys Lys Ala Ser Gly Asp Thr Phe Asn Asn Phe
                20                  25                  30

Ala Ile Ser Trp Val Arg Gln Ala Pro Gly His Gly Leu Glu Trp Val
            35                  40                  45

Gly Gly Ile Ile Pro Val Phe Asn Thr Ala Asp Tyr Ala Gln Asn Phe
        50                  55                  60

Thr Gly Arg Val Thr Ile Ser Ala Asp Lys Ala Thr Lys Thr Val Tyr
65                  70                  75                  80

Met Glu Leu Arg Ser Leu Arg Tyr Asp Asp Thr Ala Val Tyr Phe Cys
                85                  90                  95

Ala Arg Thr Lys Ile Glu Leu Asp Asn Asp Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Ala Gln Ser Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Ser Asn Ile Gly Ser Asn Thr Val Asn Trp Tyr Gln His
                165                 170                 175

Leu Pro Gly Thr Ala Pro Lys Leu Leu Ile Tyr Ser Asn Asn Gln Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Gln Ser Glu Asp Glu Ala Asp Tyr
    210                 215                 220

Tyr Cys Ala Ala Trp Asp Asp Ser Leu Asn Gly Pro Tyr Val Phe Gly
225                 230                 235                 240

Thr Gly Thr Lys Leu Thr Val Leu Gly
                245

<210> SEQ ID NO 37
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 37
```
caggtgcagc tggtgcagtc tgg                                          23

<210> SEQ ID NO 38
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 38
caggtcaact taagggagtc tgg                                          23

<210> SEQ ID NO 39
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 39
gaggtgcagc tggtggagtc tgg                                          23

<210> SEQ ID NO 40
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 40
caggtgcagc tgcaggagtc ggg                                          23

<210> SEQ ID NO 41
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 41
gaggtgcagc tgttgcagtc tgc                                          23

<210> SEQ ID NO 42
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 42
caggtacagc tgcagcagtc agg                                          23

<210> SEQ ID NO 43
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 43

```
tgaggagacg gtgaccaggg tgcc                                              24
```

<210> SEQ ID NO 44
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 44

```
tgaagagacg gtgaccattg tccc                                              24
```

<210> SEQ ID NO 45
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 45

```
tgaggagacg gtgaccaggg ttcc                                              24
```

<210> SEQ ID NO 46
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 46

```
tgaggagacg gtgaccgtgg tccc                                              24
```

<210> SEQ ID NO 47
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 47

```
gacatccaga tgacccagtc tcc                                               23
```

<210> SEQ ID NO 48
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 48

```
gatgttgtga tgactcagtc tcc                                               23
```

<210> SEQ ID NO 49
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 49

```
gatattgtga tgactcagtc tcc                                               23
```

<210> SEQ ID NO 50
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 50
gaaattgtgt tgacgcagtc tcc                                          23

<210> SEQ ID NO 51
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 51
gacatcgtga tgacccagtc tcc                                          23

<210> SEQ ID NO 52
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 52
gaaacgacac tcacgcagtc tcc                                          23

<210> SEQ ID NO 53
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 53
gaaattgtgc tgactcagtc tcc                                          23

<210> SEQ ID NO 54
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 54
cagtctgtgt tgacgcagcc gcc                                          23

<210> SEQ ID NO 55
<211> LENGTH: 23
<212> TYPE: DNA
<213> ORGANISM: Artificial sequence
<220> FEATURE:
<223> OTHER INFORMATION: PCR primer useful for amplifying VH and VL
domains

<400> SEQUENCE: 55
cagtctgccc tgactcagcc tgc                                          23

<210> SEQ ID NO 56
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 56
tcctatgtgc tgactcagcc acc                                              23

<210> SEQ ID NO 57
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 57
tcttctgagc tgactcagga ccc                                              23

<210> SEQ ID NO 58
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 58
cacgttatac tgactcaacc gcc                                              23

<210> SEQ ID NO 59
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 59
caggctgtgc tcactcagcc gtc                                              23

<210> SEQ ID NO 60
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 60
aattttatgc tgactcagcc cca                                              23

<210> SEQ ID NO 61
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 61
acgtttgatt tccaccttgg tccc                                             24

```
<210> SEQ ID NO 62
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 62
acgtttgatc tccagcttgg tccc                                          24

<210> SEQ ID NO 63
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 63
acgtttgata tccactttgg tccc                                          24

<210> SEQ ID NO 64
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 64
acgtttgatc tccaccttgg tccc                                          24

<210> SEQ ID NO 65
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 65
acgtttaatc tccagtcgtg tccc                                          24

<210> SEQ ID NO 66
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 66
cagtctgtgt tgacgcagcc gcc                                           23

<210> SEQ ID NO 67
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 67
cagtctgccc tgactcagcc tgc                                           23

<210> SEQ ID NO 68
```

```
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 68
tcctatgtgc tgactcagcc acc                                              23

<210> SEQ ID NO 69
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 69
tcttctgagc tgactcagga ccc                                              23

<210> SEQ ID NO 70
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 70
cacgttatac tgactcaacc gcc                                              23

<210> SEQ ID NO 71
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 71
caggctgtgc tcactcagcc gtc                                              23

<210> SEQ ID NO 72
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 72
aattttatgc tgactcagcc cca                                              23
```